(12) United States Patent
Imbach et al.

(10) Patent No.: US 6,767,906 B2
(45) Date of Patent: Jul. 27, 2004

(54) 2-AMINO-6-ANILINO-PURINES AND THEIR USE AS MEDICAMENTS

(75) Inventors: Patricia Imbach, Kaiseraugst (CH); Hans-Georg Capraro, Rheinfelden (CH); Jürg Zimmermann, Therwil (CH); Giorgio Caravatti, Bottmingen (CH); Pascal Furet, Thann (FR); Wolfgang Karl-Diether Brill, Cestate (IT)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 09/927,322

(22) Filed: Aug. 10, 2001

(65) Prior Publication Data

US 2002/0016329 A1 Feb. 7, 2002

Related U.S. Application Data

(63) Continuation of application No. PCT/EP00/01271, filed on Feb. 16, 2000.

(30) Foreign Application Priority Data

Feb. 18, 1999 (GB) .............................. 9903762

(51) Int. Cl.$^7$ .................. C07D 473/16; C07D 473/40; A61K 31/52; A61P 35/00; A61P 19/10
(52) U.S. Cl. ............................ 514/234.2; 514/263.4; 514/263.21; 514/263.2; 514/263.22; 514/263.23; 544/61; 544/118; 544/277
(58) Field of Search .................... 544/277, 61, 118; 514/234.2, 261, 266, 263.4, 263.21, 263.2, 263.22, 263.23

(56) References Cited

U.S. PATENT DOCUMENTS

| | | | |
|---|---|---|---|
| 4,853,386 A | 8/1989 | Friebe et al. ............ 514/266 |
| 5,066,655 A | 11/1991 | Olsson | |
| 5,565,566 A | 10/1996 | Olsson ................. 544/277 |
| 5,753,635 A | 5/1998 | Buckman et al. ........... 514/81 |
| 5,866,702 A | 2/1999 | Mackman et al. | |
| 6,255,485 B1 * | 7/2001 | Gray et al. ............. 544/277 |
| 6,479,487 B1 * | 11/2002 | Dumont et al. .......... 544/277 |

FOREIGN PATENT DOCUMENTS

| | | |
|---|---|---|
| DE | 0 212 535 | 8/1986 |
| EP | 0 773 023 | 5/1997 |
| WO | WO 88/08303 | 11/1988 |
| WO | WO 90/09178 | 8/1990 |
| WO | WO 97/16452 | 5/1997 |
| WO | WO 97/20842 | 6/1997 |
| WO | WO 97/35539 | 10/1997 |
| WO | WO 98/05335 | 2/1998 |
| WO | WO 98/07725 | 2/1998 |
| WO | WO 98/16528 | 4/1998 |
| WO | WO 99/07705 | 2/1999 |
| WO | WO 99/12927 | 3/1999 |

OTHER PUBLICATIONS

Merriam Webster's Collegiate® Dictionary, 10th Edition, entry for hydrocarbon.*
The Wordsmyth English Dictionary–Thesaurus, entry for hydrocarbon.*
The American Heritage® Dictionary of the English Language: Fourth Edition. 2000, entry for hydrocarbon.*
Hawley's Condensed Chemical Dictionary, 13$^{th}$ edition (Van Nostrand Reinhold) p. 587.*

(List continued on next page.)

*Primary Examiner*—Mark L. Berch
(74) *Attorney, Agent, or Firm*—George R. Dohmann; Lydia T. McNally

(57) ABSTRACT

This application discloses 2-amino-6-anilino-purine derivatives of the formula I

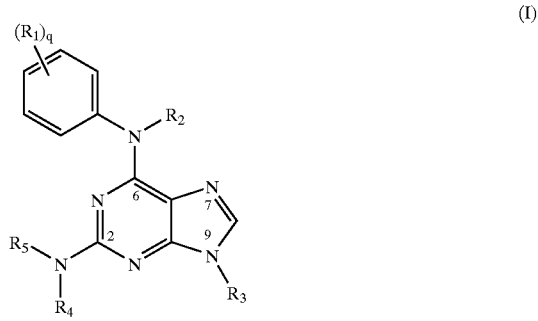

in which
q is 1–5, and
$R_1$ is
  α) —S(=O)$_k$—NR$_6$R$_7$, in which
    k is 1 or 2,
    wherein under the proviso that $R_6$ and $R_7$ cannot be simultaneously hydrogen
    α1) $R_6$, $R_7$ can be identical or different from one another and represent an aliphatic, carbocyclic, heterocyclic, carbocyclic-aliphatic or heterocyclic-aliphatic radical; hydrogen or lower aliphatic acyl; or
    α2) $R_6$ and $R_7$ together are an alkylene or alkenylene radical having from 3 up to and including 9 C atoms, in which 1–3 C atoms can be replaced by oxygen, sulfur or nitrogen,
  β) N-(aryl lower alkyl)carbamoyl, or
  γ) a radical of the formula —NH—S(=O)$_i$—R$_8$, in which
    i is 1 or 2,
    $R_8$ is an aliphatic, carbocyclic or heterocyclic radical; or
  δ) a radical of the formula —NH—C(=O)—R$_9$,
  and the other variable substituents are as defined herein. The inventive compounds inhibit p34$^{cdc2}$/cyclin B$^{cdc13}$ kinase and protein tyrosine kinase pp60$^{c-src}$ and can be used for treatment of hyperproliferative diseases, for example tumour diseases, and diseases which respond to inhibition of the activity of protein tyrosine kinase pp60$^{c-src}$, in particular osteoporosis.

15 Claims, No Drawings

OTHER PUBLICATIONS

Gray et al., "Exploiting Chemical Libraries, Structure, and Genomics in the Search for Kinase Inhibitors", Science, vol. 281, pp. 533–538 (1998).

Rosana et al., "A Cyclin–Dependent Kinase Inhibitor Inducing Cancer Cell Differentiation: Biochemical Identification Using Xenopus Egg Extracts", Proc. Natl. Acad. Sci. USA, vol. 96, pp. 4797–4802 (1999).

Schow et al., "Synthesis and Activity of 2,6,9–Trisubstituted Purines", Bioorganic & Med. Chem. Letters, vol. 7, No. 21, pp. 2697–2702 (1997).

Proc. Natl. Acad. Sci. USA—vol. 96, pp. 4797–4802—Apr. 1999—Biochemistry Rosania et al.

* cited by examiner

2-AMINO-6-ANILINO-PURINES AND THEIR USE AS MEDICAMENTS

This application is a continuation of PCT Patent Application No. PCT/EP00/011271, filed Feb. 16, 2000, which in its entirety is herein incorporated by reference.

The invention relates to 2-amino-6-anilino-purine derivatives and to processes and novel intermediates for their preparation, pharmaceutical formulations which comprise such derivatives, and the use of these derivatives as medicaments.

The invention relates to 2-amino-6-anilino-purine derivatives of the formula I in which q is 1–5,
$R_1$ is
α) —S(=O)$_k$—NR$_6$R$_7$, in which
  k is 1 or 2,
  wherein under the proviso that $R_6$ and $R_7$ cannot be simultaneously hydrogen
  α1) $R_6$, $R_7$ can be identical or different from one another and represent an aliphatic, carbocyclic, heterocyclic, carbocyclic-aliphatic or heterocyclic-aliphatic radical; hydrogen or lower aliphatic acyl; or
  α2) $R_6$ and $R_7$ together are a substituted or unsubstituted alkylene or alkenylene radical, in which 1–3 C atoms can be replaced by oxygen, sulfur or nitrogen;
β) N-(aryl lower alkyl)carbamoyl;
γ) a radical of the formula —NH—S(=O)$_i$—R$_8$, in which
  i is 1 or 2,
  $R_8$ is an aliphatic, carbocyclic or heterocyclic radical; or
δ) a radical of the formula —NH—C(=O)—R$_9$, in which
  $R_9$ is alkoxy, aryloxy, alkenyl, alkynyl, heterocyclyl alkynyl, aryl alkynyl, heteroaryl alkynyl, alkynyloxy or aryl alkynyloxy, which in each case is unsubstituted or substituted;
  where, if more than one radical $R_1$ is present in the molecule, these can be identical or different from one another,
$R_2$ is hydrogen, carbamoyl or N-lower alkyl-carbamoyl,
$R_3$ is a lower aliphatic radical, which is unsubstituted or substituted by hydroxy, lower alkoxy, amino, lower alkylamino or N,N-di-lower alkylamino and
  a) $R_4$ is hydrogen, amino, phenylamino, lower alkylamino, hydroxyl, phenoxy, lower alkoxy, acyl having 1–30 C atoms, a substituted aliphatic hydrocarbon radical having not more than 29 C atoms, a substituted carbocyclic or carbocyclic-aliphatic radical having not more than 29 C atoms or a heterocyclic or heterocyclic-aliphatic radical having not more than 20 C atoms and not more than 9 heteroatoms and
    $R_5$, independently of $R_4$, is as defined above for $R_4$, with the exception of hydrogen, or
  b) $R_4$ and $R_5$ together are a substituted or unsubstituted alkylene or alkenylene radical having in each case not more than 15 C atoms, in which 1–3 C atoms can be replaced by oxygen, sulfur or nitrogen, and their salts.

Unless stated otherwise, in the present disclosure organic radicals designated "lower" contain not more than 7, preferably not more than 4, carbon atoms.

q is preferably 1–3, as a rule 1 or 2, preferably 1. Only if it is possible for steric reasons, can q also be 4 or 5. If q is 1, $R_1$ is, for example, in the 3 position or, preferably, in the 4 position.

If $R_1$ represents —S(=O)$_k$—NR$_6$R$_7$, k can be 1 or 2. Preferably k is 2.

Halogen is, for example, fluorine, chlorine, bromine or iodine. Preferably it is fluorine or chlorine.

An aliphatic radical $R_6$ or $R_7$ is an unsubstituted or substituted alkyl or in each case mono- or polyunsaturated alkenyl or alkynyl radical having in each case not more than 20 C atoms, i.e. an unsubstituted or substituted $C_1$–$C_{20}$alkyl, $C_2$–$C_{20}$alkenyl or $C_2$–$C_{20}$alkynyl radical. As a rule, these radicals, including their substituents, have not more than 16, in particular not more than 12, and especially not more than 8, C atoms. Preferably, the aliphatic radical is methyl, ethyl, n-propyl, iso-propyl, n-butyl, iso-butyl, tert-butyl, 3-methylbutyl, n-pentyl, 4-methyl-n-pentyl, n-hexyl, 5-methyl-n-hexyl, n-heptyl, 6-methyl-n-heptyl, n-octyl, 7-methyl-n-octyl, n-nonyl, 8-methyl-n-nonyl, n-decyl or 9-methyl-n-decyl. Most preferably, the aliphatic radical is methyl, ethyl, n-propyl, iso-propyl, n-butyl, iso-butyl, 3-methylbutyl, n-heptyl or n-octyl. The alkenyl radical is, for example, allyl, propenyl, isopropenyl, 2- or 3-methallyl and 2- or 3-butenyl. The alkynyl radical is, for example, propargyl or butynyl. In corresponding unsaturated radicals, the double bond is located, in particular, in a position higher than the α position to the free valency.

Unsaturated radicals are those which contain one or more, in particular conjugated and/or isolated, multiple bonds (double bonds and/or triple bonds). The term cyclic radicals also encompasses aromatic radicals, for example those in which at least one 6-membered carbocyclic or one 5- to 8-membered heterocyclic ring contains the maximum number of non-cumulative double bonds. Carbocyclic radicals in which at least one ring is present as a 6-membered aromatic ring (i.e. benzene ring) are called aryl radicals.

The substituted aliphatic radical $R_6$ or $R_7$ can carry one or more identical or different radicals. Depending on the nature of the substituents, these can be attached via a single or multiple bond or linked in spiro form. Substituents are, for example, halogen, such as chlorine, fluorine, bromine or iodine, amino, lower alkylamino, di-lower alkylamino, ω-amino-lower alkylamino, lower alkanoylamino, aroylamino, such as, benzoylamino, hydroxylamino, hydroxylamino, lower alkoxy-amino, aryloxyamino, such as, phenyloxyamino, amino-cyclohexyl-amino-, amino-phenyl-amino-, carbamoyl-amino (ureido, —NH—C(=O)—NH$_2$), (N-lower alkyl-carbamoyl)-amino (—NH—C(=O)—NH-lower alkyl), (N-[ω-amino-lower alkyl]-carbamoyl)-amino (—NH—C(=O)—NH-lower alkyl-NH$_2$), (N-phenyl-carbamoyl)-amino (—NH—C(=O)—NH-phenyl), thio, lower alkylthio, such as methylthio, thiocarbamoyl (—C(=S)—NH$_2$), thioureido (—NH—C (=S)—NH$_2$), N-lower alkyl-thioureido (—NH—C(=S)—NH-lower alkyl), N-phenyl-thioureido (—NH—C(=S)—NH-phenyl), guanidino, N-lower alkyl-guanidino, carboxyl, lower alkoxycarbonyl, aryloxycarbonyl, such as, phenyloxycarbonyl, benzyloxycarbonyl, hydroxylaminocarbonyl, aminoacyl-amino, carbamoyl, amidino (—C[=NH]—NH$_2$), cyano, hydroxy, lower alkoxy, aryloxy, such as, phenyloxy, aminocarbonyl-oxy (—O—C[=O]—NH$_2$), oxo, aminosulfonyl and lower alkylsulfonyl-amino. One preferred substituent is hydroxy. Another preferred substituent is lower alkoxy.

A carbocyclic radical $R_6$ or $R_7$ is, in particular, a mono-, bi- or polycyclic cycloalkyl, cycloalkenyl or cycloalkadienyl radical, or a corresponding aryl radical. Preferred radicals are those having not more than 14, in particular 10, ring carbon atoms and 3- to 8-, preferably 3- to 7-, especially 3 and 6-membered rings, it also being possible for them to carry one or more, for example two, acyclic radicals, for example those mentioned above, and in particular the lower alkyl radicals, or further carbocyclic or heterocyclic radicals.

Cycloalkyl radicals contain, in particular, from 3 up to and including 10 C atoms, preferably from 3 up to and including 6 C atoms, and are independently from each other, for example, cyclopropyl, cyclobutyl, cyclopentyl, cyclohexyl, cycloheptyl and cyclooctyl, as well as bicyclo[2.2.2]octyl, 2-bicyclo[2.2.1]heptyl and adamantyl, which can also be substituted by 1, 2 or more, for example, lower alkyl radicals, in particular methyl radicals. Preferably cycloalkyl is cyclopropyl, cyclobutyl, cyclopentyl or cyclohexyl. Cycloalkenyl is, for example, one of the monocyclic cycloalkyl radicals already mentioned which carries a double bond in the 1, 2 or 3 position.

An aryl radical is, in particular, a phenyl, or furthermore a naphthyl, such as 1- or 2-naphthyl, a tetrahydronaphthyl, a biphenylyl, such as, in particular, 4-biphenylyl, and moreover also an anthryl, fluorenyl and azulenyl, as well as their aromatic analogues having one or more saturated rings. Aryl radicals which carry acyclic radicals, such as lower alkyl, are, in particular, o-, m- and p-tolyl und xylyl radicals with methyl radicals in various sites.

Unless stated otherwise, carbocyclic and heterocyclic radicals above and below can be substituted once or more than once, for example twice or three times, in particular by halogen, lower alkyl, lower alkoxy, aryloxy, lower alkoxycarbonyl, trifluoromethyl, hydroxy, nitro, imidazolyl, morpholinyl, pyrrolyl, pyrrolidinyl, pyrazolyl, pyridinyl, pyrazinyl, pyrimidinyl, pyridazinyl, indolyl, piperidinyl, piperazinyl, oxazolyl, thiazolyl, amino, lower alkylamino, di-lower alkylamino, carbamoyl, lower alkylcarbamoyl, carboxyl, methylenedioxy, cyano or lower alkyl which is substituted by halogen.

Aryl radicals $R_6$, $R_7$ are preferably substituted by halogen, lower alkyl, lower alkoxy, phenoxy, lower alkoxycarbonyl, trifluoromethyl, imidazolyl, morpholinyl, pyrrolyl, pyrrolidinyl, pyrazolyl, pyridinyl, pyrazinyl, pyrimidinyl, pyridazinyl, indolyl, piperidinyl, piperazinyl oxazolyl, thiazolyl, amino, lower alkylamino, di-lower alkylamino, carbamoyl or lower alkyl which is substituted by halogen. Most preferably aryl radicals $R_6$, $R_7$ are substituted by halogen, $C_1$–$C_4$ alkyl, $C_1$–$C_4$ alkoxy, phenoxy, $C_1$–$C_4$ alkoxycarbonyl, trifluoromethyl, imidazolyl or morpholinyl.

Preferably, cycloalkyl radicals are substituted by halogen, hydroxy, lower alkoxy, amino, lower alkylamino, di-lower alkylamino, carbamoyl or lower alkylcarbamoyl. Most preferably cycloalkyl radicals $R_6$, $R_7$ are substituted by hydroxy.

Carbocyclic-aliphatic radicals $R_6$ or $R_7$ are those in which an aliphatic radical, in particular one having not more than 5, preferably not more than 3, carbon atoms, such as, in particular, methyl, ethyl, propyl and vinyl, carries one or more carbocyclic radicals, which may or may not be aromatic, as defined above. Cycloalkyl-lower alkyl and aryl-lower alkyl radicals, and their analogues unsaturated in the ring and/or chain, which carry the ring on the terminal C atom of the chain are mentioned in particular.

Cycloalkyl-lower alkyl or -lower alkenyl is, for example, a methyl, 1- or 2-ethyl, 1- or 2-vinyl, 1-, 2- or 3-propyl or allyl which is substituted by one of the abovementioned cycloalkyl radicals, those substituted at the end of the linear chain being preferred.

Further preferred carbocyclic-aliphatic radicals $R_6$ or $R_7$ are ω-aryl lower alkyl and ω,ω-diaryl lower alkyl, wherein aryl is preferably phenyl, chlorophenyl and naphthyl and lower alkyl is preferably methyl, ethyl or propyl. Most preferred carbocyclic-aliphatic radicals $R_6$ or $R_7$ are benzyl, 3-phenyl-1-methylpropyl, 3,3-diphenylpropyl, chlorophenylmethyl and naphthylmethyl.

Heterocyclic radicals including heterocyclic-aliphatic radicals, are, in particular, monocyclic, but also bi- or polycyclic, aza-, thia-, oxa-, thiaza-, oxaza-, diaza-, triaza- or tetraaza radicals of aromatic character, and corresponding partly or, in particular, completely saturated heterocyclic radicals of this type, it being possible for such radicals to carry, where appropriate, for example as the abovementioned carbocyclic or aryl radicals, further aliphatic, carbocyclic or heterocyclic radicals and/or to be mono-, di- or polysubstituted by functional groups. These radicals are, in particular, monocyclic or bicyclic radicals with one nitrogen, oxygen or sulfur atom, and in particular aromatic radicals of this type, for example 2-pyrryl or 3-pyrryl, pyridyl, for example 2-, 3- or 4-pyridyl, and furthermore thienyl, for example 2- or 3-thienyl, or furyl, for example 2-furyl; analogous bicyclic radicals with one nitrogen, oxygen or sulfur atom are, for example, indolyl, such as 2- or 3-indolyl, quinolyl, such as 2- or 4-quinolyl, isoquinolyl, such as 3- or 5-isoquinolyl, benzofuranyl, such as 2-benzofuranyl, chromenyl, such as 3-chromenyl, or benzothienyl, such as 2- or 3-benzothienyl. Suitable monocyclic and bicyclic radicals with more than one heteroatom are, for example, imidazolyl, such as 2-imidazolyl, pyrimidinyl, such as 2- or 4-pyrimidinyl, oxazolyl, such as 2-oxazolyl, isoxazolyl, such as 3-isoxazolyl, or thiazolyl, such as 2-thiazolyl, or benzimidazolyl, such as 2-benzimidazolyl, benzoxazolyl, such as 2-benzoxazolyl, or quinazolyl, such as 2-quinazolinyl. Corresponding partly, or, in particular, completely saturated analogous radicals are also suitable, such as 2-tetrahydrofuryl, 4-tetrahydrofuryl, 2- or 3-pyrrolidyl, 2-, 3- or 4-piperidyl and also 2- or 3-morpholinyl, 2- or 3-thiomorpholinyl, 2-piperazinyl and N,N'-bis-lower alkyl-2-piperazinyl radicals. These radicals can also carry one or more aliphatic, carbocyclic or heterocyclic radicals, in particular those mentioned above. Heterocyclic-aliphatic radicals are derived, in particular, from aliphatic radicals having not more than 7, preferably not more than 4, carbon atoms, for example from those mentioned above, preferably methyl and ethyl, and can carry one, two or more heterocyclic radicals, for example those mentioned above, it also being possible for the ring to be bonded to the chain by one of its nitrogen atoms.

Preferred monocyclic and bicyclic heterocyclic radicals $R_6$ or $R_7$ with one heteroatom are pyridyl, thienyl and quinolyl, in particular 2-pyridyl, 3-quinolyl and 2-thienyl.

Lower aliphatic acyl $R_6$ or $R_7$ is an unsubstituted or substituted aliphatic acyl, which can in each case be mono- or polyunsaturated. As a rule, these radicals, including their substituents, have not more than 7, and especially not more than 4, C atoms. Preferably, aliphatic acyl $R_6$ or $R_7$ is formyl, acetyl, propionyl or butanoyl. A monounsaturated aliphatic acyl radical $R_6$ or $R_7$ can be, for example, acryloyl, methacryloyl or crotyloyl. These radicals can in each case be substituted once or more than once, for example twice or three times, in particular by halogen, hydroxy, lower alkoxy, lower alkoxycarbonyl, amino, lower alkylamino, di-lower alkylamino, carbamoyl, lower alkylcarbamoyl, carboxyl, methylenedioxy or cyano.

In case of $R_6$ and $R_7$ together are a substituted or unsubstituted alkylene or alkenylene radical, in which 1–3 C atoms can be replaced by oxygen, sulfur or nitrogen, as a rule the alkenylene or alkenylene radicals have from 3 up to and including 9, preferably 4 up to and including 7, and most preferably from 5 to 6, C atoms, whereby none or one C atom is replaced by nitrogen or oxygen and can be substituted by halogen, hydroxy, lower alkoxy, amino, lower alkylamino, di-lower alkylamino, carbamoyl, lower alkylcarbamoyl or a radical —$(CH_2)_y$—$R_{10}$, in which y is 0 to 3, preferably 0 to 2, and $R_{10}$ is hydrogen or phenyl, unsubstituted or substituted by halogen, halogen lower alkyl, lower alkoxy, hydroxy, lower alkoxycarbonyl, amino, lower alkylamino, di-lower alkylamino, carbamoyl, lower alkylcarbamoyl, carboxyl, methylenedioxy or cyano. Most preferably the alkylene or alkenylene radical is unsubstituted or substituted by a radical —$(CH_2)_y$—$R_{10}$, in which $R_{10}$ is preferably hydrogen or phenyl, which is unsubstituted or substituted with halogen, trifluoromethyl or lower alkoxy.

In a preferred embodiment of the invention $R_6$ and $R_7$ are together a radical of the formula (II),

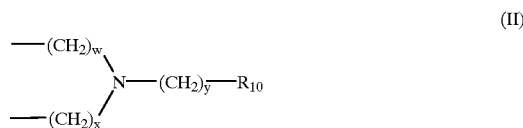

in which w is 0 to 4, preferably 1 to 3, x is 0 to 4, preferably 1 to 3, y is 0 to 2, and $R_{10}$ is hydrogen or phenyl, which is unsubstituted or substituted by halogen, halogen lower alkyl, lower alkoxy, hydroxy, lower alkoxycarbonyl, amino, lower alkylamino, di-lower alkylamino, carbamoyl, lower alkylcarbamoyl, carboxyl, methylenedioxy or cyano. Preferably $R_{10}$ is hydrogen or phenyl, which is unsubstituted or substituted with halogen, trifluoromethyl or lower alkoxy.

In yet another preferred embodiment of the invention $R_6$ and $R_7$ are together an unsubstituted alkylene radical having 5 C atoms, whereby one C atom is replaced by oxygen.

If $R_1$ is N-(aryl lower alkyl)carbamoyl, aryl is preferably phenyl, which is unsubstituted or substituted by halogen, lower alkoxy, lower alkyl, trifluoromethyl, hydroxy, nitro, amino, lower alkylamino, di-lower alkylamino, lower alkoxycarbonyl, carboxyl, carbamoyl, lower alkylcarbamoyl, methylenedioxy or cyano. Most preferably phenyl is unsubstituted or substituted by halogen, lower alkoxy, lower alkyl or trifluoromethyl; in the aliphatic moiety lower alkyl is preferably methyl, ethyl or propyl, whereby methyl is most preferred.

An aliphatic radical $R_8$ is an unsubstituted or substituted lower alkyl or in each case mono- or polyunsaturated lower alkenyl or lower alkynyl radical. As a rule, these radicals, including their substituents, have not more than 16, in particular not more than 12, and especially not more than 8, C atoms. Preferably, the aliphatic radical $R_8$ is methyl, ethyl, n-propyl, iso-propyl, n-butyl, iso-butyl, tert-butyl, n-pentyl, n-hexyl or n-heptyl. Most preferably, the aliphatic radical $R_8$ is methyl, ethyl, n-propyl, iso-propyl, n-butyl, iso-butyl or tert-butyl. The alkenyl radical $R_8$ is, for example, allyl, propenyl, isopropenyl, 2- or 3-methallyl and 2- or 3-butenyl. The alkynyl radical $R_8$ is, for example, propargyl or butynyl. These radicals can in each case be substituted once or more than once, for example twice or three times, in particular by halogen, hydroxy, lower alkoxy, lower alkoxycarbonyl, amino, lower alkylamino, di-lower alkylamino, carbamoyl, lower alkylcarbamoyl, carboxyl, methylenedioxy or cyano.

A carbocyclic radical $R_8$ is, in particular, a mono-, bi- or polycyclic cycloalkyl, cycloalkenyl or cycloalkadienyl radical, or a corresponding aryl radical. Preferred radicals $R_8$ are those having not more than 10, ring carbon atoms and 3- to 8-, preferably 5- to 7-, especially 6-membered rings, it also being possible for them to carry one or more, for example two, acyclic radicals, for example those mentioned above, and in particular the lower alkyl radicals, or further carbocyclic or heterocyclic radicals. Preferably the carbocyclic radical $R_8$ is aryl, which is unsubstituted or substituted by halogen, lower alkyl, lower alkoxy, phenoxy, lower alkoxycarbonyl, trifluoromethyl, imidazolyl, morpholinyl, pyrrolyl, pyrrolidinyl, pyrazolyl, pyridinyl, pyrazinyl, pyrimidinyl, pyridazinyl, indolyl, piperidinyl, piperazinyl oxazolyl, thiazolyl, amino, lower alkylamino, di-lower alkylamino, carbamoyl or lower alkyl which is substituted by halogen. More preferably the aryl radical $R_8$ is substituted by halogen, $C_1$–$C_4$alkyl, $C_1$–$C_4$alkoxy, phenoxy, $C_1$–$C_4$alkoxycarbonyl, trifluoromethyl, imidazolyl or morpholinyl. Most preferably it is substituted by $C_1$–$C_4$alkyl or $C_1$–$C_4$alkoxy. Heterocyclic radicals $R_8$ have the meaning as defined above for $R_6$ or $R_7$.

An alkoxy, aryloxy, alkenyl, alkynyl, heterocyclyl alkynyl, aryl alkynyl, heteroaryl alkynyl, alkynyloxy or aryl alkynyloxy radical $R_9$ is an unsubstituted or substituted radical having preferably not more than 20 C atoms. As a rule, these radicals, including their substituents, have not more than 12, in particular not more than 8, and especially not more than 4, C atoms. Preferably, the aliphatic moiety of the alkoxy radical $R_9$ is methyl, ethyl, n-propyl, iso-propyl, n-butyl, iso-butyl, tert-butyl, 3-methylbutyl, n-pentyl, 4-methyl-n-pentyl, n-hexyl, 5-methyl-n-hexyl, n-heptyl, 6-methyl-n-heptyl, n-octyl, 7-methyl-n-octyl, n-nonyl, 8-methyl-n-nonyl, n-decyl, 9-methyl-n-decyl, n-undecyl or dodecyl. More preferably, it is methyl, ethyl, n-propyl, iso-propyl, n-butyl, iso-butyl, 3-methylbutyl, n-heptyl or n-octyl and most preferably it is methyl, ethyl, n-propyl, iso-propyl, n-butyl or iso-butyl. The alkenyl radical $R_9$ is, for example, allyl, propenyl, isopropenyl, 2- or 3-methallyl and 2- or 3-butenyl. The alkynyl radical $R_9$ or the alkynyl moiety of the aryl alkynyl radical $R_9$ is, for example, ethinyl, 1-propargyl, 2-propargyl, 1-butynyl, 2-butynyl, 3-butynyl or 3,3-dimethyl-1-butynyl. In corresponding unsaturated radicals, the double bond is located, in particular, in a position higher than the a position to the free valency. These radicals $R_9$ can in each case be substituted once or more than once, for example twice or three times, in particular by halogen, hydroxy, phenyl, lower alkoxy, lower alkoxycarbonyl, amino, lower alkylamino, di-lower alkylamino, carbamoyl, lower alkylcarbamoyl, carboxyl, methylenedioxy, tri-lower alkyl silyl or cyano. Preferably these radicals are unsubstituted substituted by tri-lower alkyl silyl or phenyl. The heterocyclyl moiety of the heterocyclyl alkynyl $R_9$ comprises one or two heteroatoms selected from the group consisting of nitrogen, sulfur and oxygen, and is unsubstituted or substituted. Preferably the heterocyclyl moiety is unsubstituted or substituted by lower alkyl, like e.g. methyl or ethyl, and selected from the group consisting of piperidinyl, pyrrolidinyl, piperazinyl, lower alkyl piperazinyl, morpholinyl and thiamorpholinyl. Most preferably it is piperidinyl or lower alkyl piperazinyl. In heteroaryl alkynyl $R_9$ the heteroaryl moiety comprises one or two heteroatoms selected from the group consisting of nitrogen, sulfur and oxygen. Preferably, the heteroaryl moiety in heteroaryl alkynyl $R_9$ is selected from the group consisting of pyridyl, pyrimidyl and thienyl, and is preferably unsubstituted or substituted by lower alkyl.

$R_3$ is an aliphatic radical having in each case not more than 7 C atoms, i.e. an unsubstituted or substituted $C_1$–$C_7$alkyl, $C_2$–$C_7$alkenyl or $C_2$–$C_7$alkynyl radical, which is preferably unsubstituted. As a rule, these radicals, have not more than 4, in particular 2 or 3, C atoms. Preferably, the aliphatic radical is methyl, ethyl, n-propyl, iso-propyl, n-butyl, iso-butyl, tert-butyl. More preferably it is methyl, ethyl, n-propyl or iso-propyl. The $C_2$–$C_7$alkenyl radical $R_3$ is, for example, allyl, propenyl, isopropenyl, 2- or 3-methallyl and 2- or 3-butenyl. The $C_2$–$C_7$alkynyl radical $R_3$ is, for example, ethinyl, 1-propargyl, 2-propargyl, 1-butynyl, 2-butynyl or 3-butynyl.

Acyl $R_4$ or $R_5$ having 1–30 C atoms is derived from an unmodified or functionally modified carboxylic acid and is, in particular, one of the part formula Z—C(=W)—, in which W is oxygen, sulfur or imino and Z is hydrogen, hydrocarbyl $R_o$ having not more than 29 C atoms, hydrocarbyloxy $R_o$—O— or an amino group, in particular one of the formula $R_{11}(R_{12})N$—.

Hydrocarbyl (a hydrocarbon radical) $R_o$ is an acyclic (aliphatic), carbocyclic or carbocyclic-acyclic hydrocarbon radical having not more than 29 C atoms, in particular not more than 18, and preferably not more than 12, carbon atoms, and is saturated or unsaturated and unsubstituted or substituted. Instead of one, two or more carbon atoms, it can also contain identical or different heteroatoms, such as, in particular, oxygen, sulfur and nitrogen, in the acyclic and/or cyclic moiety; in the latter case, it is called a heterocyclic radical (heterocyclyl radical) or a heterocyclic-acyclic radical.

An acyclic unsubstituted hydrocarbon radical $R_o$ is, in particular, a straight-chain or branched lower alkyl, lower alkenyl, lower alkadienyl or lower alkynyl radical. Lower alkyl is, for example, methyl, ethyl, n-propyl, isopropyl, n-butyl, isobutyl, sec-butyl or tert-butyl, and furthermore also n-pentyl, isopentyl, n-hexyl, isohexyl and n-heptyl. Lower alkenyl is, for example, allyl, propenyl, isopropenyl, 2- or 3-methallyl and 2- or 3-butenyl. Lower alkadienyl is, for example, 1-penta-2,4-dienyl; lower alkynyl is, for example, propargyl or butynyl. In corresponding unsaturated radicals, the double bond is located, in particular, in a position higher than the α position to the free valency.

A carbocyclic hydrocarbon radical $R_o$ is, in particular, a mono-, bi- or polycyclic cycloalkyl, cycloalkenyl or cycloalkadienyl radical, or a corresponding aryl radical. Preferred radicals are those having not more than 14, in particular 12, ring carbon atoms and 3- to 8-, preferably 5- to 7-, especially 6-membered rings, it also being possible for them to carry one or more, for example two, acyclic radicals, for example those mentioned above, and in particular the lower alkyl radicals, or further carbocyclic radicals. Carbocyclic-acyclic radicals are those in which an acyclic radical, in particular one having not more than 7, preferably not more than 4, carbon atoms, such as, in particular, methyl, ethyl and vinyl, carries one or more carbocyclic radicals, which may or may not be aromatic, as defined above. Cycloalkyl-lower alkyl and aryl-lower alkyl radicals, and their analogues unsaturated in the ring and/or chain, which carry the ring on the terminal C atom of the chain are mentioned in particular.

An aryl radical $R_0$ is, in particular, a phenyl, or furthermore a naphthyl, such as 1- or 2-naphthyl, a biphenylyl, such as, in particular, 4-biphenylyl, and moreover also an anthryl, fluorenyl and azulenyl, as well as their aromatic analogues having one or more saturated rings. Preferred aryl-lower alkyl and -lower alkenyl radicals $R_0$ are, for example, phenyl-lower alkyl or phenyl-lower alkenyl with a terminal phenyl radical, for example benzyl, phenethyl, 1-, 2- or 3-phenylpropyl, diphenylmethyl (benzhydryl), trityl and cinnamyl, and furthermore also 1- or 2-naphthylmethyl. Aryl radicals $R_0$ which carry acyclic radicals, such as lower alkyl, are, in particular, o-, m- and p-tolyl und xylyl radicals with methyl radicals in various sites.

As has already been mentioned, a hydrocarbyl (including a heterocyclyl) can be substituted by one, two or more identical or different substituents (functional groups); the following substituents are particularly suitable: free, etherified and esterified hydroxyl groups; mercapto and lower alkylthio and unsubstituted or substituted phenylthio groups; halogen atoms, such as chlorine and fluorine, but also bromine and iodine; oxo groups, which are in the form of formyl (i.e. aldehydo) and keto groups, and also corresponding acetals or ketals; azido and nitro groups; primary, secondary and preferably tertiary amino groups, primary or secondary amino groups protected by conventional protective groups, acylamino groups and diacylamino groups, and unmodified or functionally modified sulfo groups, such as sulfamoyl groups or sulfo groups present in salt form. All these functional groups should not be on the C atom from which the free valency comes, and they are preferably separated from this by 2 or even more C atoms. The hydrocarbyl radical can also carry free and functionally modified carboxyl groups, such as carboxyl groups present in salt form or esterified carboxyl groups, carbamoyl, ureido or guanidino groups which may or may not carry one or two hydrocarbon radicals, and cyano groups.

An etherified hydroxyl group present as a substituent in hydrocarbyl is, for example, a lower alkoxy group, such as the methoxy, ethoxy, propoxy, isopropoxy, butoxy and tert-butoxy group, which can also be substituted. Thus, such a lower alkoxy group can be substituted by halogen atoms, for example once, twice or several times, in particular in the 2 position, as in the 2,2,2-trichloroethoxy-, 2-chloroethoxy or 2-iodoethoxy radical, or by hydroxyl or lower alkoxy radicals, in each case preferably once, in particular in the 2-position, as in the 2-methoxyethoxy radical. A particularly preferred embodiment of the etherified hydroxyl groups exists in oxaalkyl radicals in which one or more C atoms in an alkyl, preferably a linear alkyl, are replaced by oxygen atoms, which are preferably separated from one another by more than one (in particular 2) C atoms, so that they form a group (—O—$CH_2$—$CH_2$)$_n$—, which may or may not recur more than one, in which n is 1 to 14. Such etherified hydroxyl groups are furthermore also substituted or unsubstituted phenoxy radicals and phenyl-lower alkoxy radicals, such as, in particular, benzyloxy, benzhydryloxy and triphenylmethoxy (trityloxy), as well as heterocyclyloxy radicals, such as, in particular, 2-tetrahydropyranyloxy. A particular etherified hydroxyl group is the grouping methylenedioxy or ethylenedioxy, the former as a rule bridging 2 adjacent C atoms, in particular in aryl radicals, and the latter being bonded to one and the same C atom and being regarded as a protective group for oxo.

Etherified hydroxyl groups in this connection are also to be understood as meaning silylated hydroxyl groups, such as are present, for example, in tri-lower alkylsilyloxy, such as trimethylsilyloxy and dimethyl-tert-butylsilyloxy, or phenyl di-lower alkylsilyloxy or lower alkyl-diphenylsilyloxy.

An esterified hydroxyl group present as a substituent in hydrocarbyl is, for example, lower alkanoyloxy.

An esterified carboxyl group present as a substituent in hydrocarbyl is one in which the hydrogen atom is replaced by one of the hydrocarbon radicals characterized above, preferably a lower alkyl or phenyl-lower alkyl radical; an example of an esterified carboxyl group is, for example, lower alkoxycarbonyl or phenyl-lower alkoxycarbonyl which is unsubstituted or substituted in the phenyl moiety, in particular the methoxy-, ethoxy-, tert-butoxy- and benzyloxycarbonyl group, and also a lactonized carboxyl group.

A primary amino group —$NH_2$ as a substituent of hydrocarbyl can also be present in protected form. A secondary amino group carries, instead of one of the two hydrogen atoms, a hydrocarbyl radical, preferably an unsubstituted one, such as one of those mentioned above, in particular lower alkyl, and can also be present in a protected form.

A tertiary amino group occurring as a substituent in hydrocarbyl carries 2 different or, preferably, identical hydrocarbyl radicals (including the heterocyclic radicals) such as the unsubstituted hydrocarbyl radicals characterized above, in particular lower alkyl.

In a group of the formula $R_{11}(R_{12})N$—, $R_{11}$ and $R_{12}$ independently of one another are each hydrogen, lower alkylsulfonyl, acyclic $C_1$–$C_7$hydrocarbyl (such as, in particular, $C_1$–$C_4$alkyl or $C_2$–$C_4$alkenyl) which is unsubstituted or substituted, for example by amino, guanidino, phenyl, hydroxyphenyl, carboxyl, carbamoyl, imidazolyl, mercapto or methylthio, or monocyclic aryl, aralkyl or aralkenyl which has not more than 10 C atoms and is unsubstituted or substituted by $C_1$–$C_4$alkyl, $C_1$–$C_4$alkoxy, halogen and/or nitro, it being possible for the carbon-containing radicals $R_{11}$ and $R_{12}$ to be bonded to one another by a carbon-carbon bond or an oxygen atom, a sulfur atom or a nitrogen atom which is unsubstituted or substituted by hydrocarbyl. In such a case, together with the nitrogen atom of the amino group, they form a nitrogen-containing heterocyclic ring. Examples of particularly preferred groups of the formula $R_{11}(R_{12})N$— are the following: amino, lower alkylamino, such as methylamino, or ω-amino-lower alkylamino, such as 2-amino-ethylamino or 3-amino-propylamino; di-lower alkylamino, such as dimethylamino or diethylamino; pyrrolidino, 2-hydroxymethyl-pyrrolidino, piperidino, 4-(2-amino-ethyl)-piperidino, morpholino or thiomorpholino; piperazino, 4-methyl-piperazino, 4-(2-amino-ethyl)-piperazino, or phenylamino, diphenylamino or dibenzylamino which are unsubstituted or, in particular, substituted in the phenyl moiety, for example by lower alkyl, lower alkoxy, halogen and/or nitro; and among the protected groups, in particular lower alkoxycarbonylamino, such as tert-butoxycarbonylamino, phenyl-lower alkoxycarbonylamino, such as 4-methoxybenzyloxycarbonylamino, and 9-fluorenyl-methoxycarbonylamino. Preferred groups of the formula Z—C(=W)— in which Z is a group of the formula $R_{11}$($R_{12}$)N— are carbamoyl, N-methyl-carbamoyl, N-(ω-amino-lower alkyl)-carbamoyl, N-(α-amino-acyl)carbamoyl, N-phenylcarbamoyl, N-methylsulfonyl-carbamoyl and corresponding radicals in which W is not oxygen but sulfur or imino, such as amidino, N-methyl-amidino [$CH_3$—NH—C(=NH)—], N-methyl-thiocarbamoyl [$CH_3$—NH—C(=S)—] or N-(ω-amino-lower alkyl)-thiocarbamoyl. For example, a radical of the formula —N($R_4$)—$R_5$ in which $R_4$ is hydrogen and $R_5$ is amidino is guanidino [$H_2N$—C(=NH)—NH—].

Preferred compounds of the formula I according to the invention are, for example, those in which hydrocarbyl $R_o$ has the following preferred meanings of an acyclic hydrocarbyl: a $C_1$–$C_{20}$alkyl, a $C_2$–$C_{20}$hydroxyalkyl, the hydroxyl group of which is in any position other than the 1 position, preferably in the 2 position, a cyano-[$C_1$–$C_{20}$]-alkyl, the cyano group in which is preferably in the 1 or ω position, or a carboxy-[$C_1$–$C_{20}$]-alkyl, the carboxyl group of which is preferably in the 1 or ω position and can be present in the free form or also in salt form, or as a $C_1$–$C_4$alkylester ($C_1$–$C_4$alkoxycarbonyl) or benzylester (benzyloxycarbonyl), and a $C_3$–$C_{20}$alkenyl, the free valency of which is not on the same C atom as the double bond, all the radicals mentioned, excluding those having the $C_3$–$C_5$alkyl base structure, containing a linear (unbranched) alkyl chain; and furthermore also a linear (mono-, di- to hexa)-oxoalkyl having 4–20 chain members, in which one or more of the C atoms, from C-3 on, of a linear $C_4$–$C_{20}$alkyl is replaced by oxygen atoms, which are separated from one another by at least 2 C atoms and are preferably in positions 3, 6, 9, 12, 15 and 18.

Preferred compounds of the formula I according to the invention are also those in which hydrocarbyl $R_o$ has the following preferred meanings of a carbocyclic or heterocyclic and also carbocyclic-acyclic or heterocyclic-acyclic hydrocarbyl: a bicyclic or preferably monocyclic aryl, in particular phenyl, and furthermore naphthyl, which can carry one or more of the following substituents: halogen atoms, in particular fluorine, chlorine and bromine, $C_1$–$C_4$alkyl radicals, in particular methyl, $C_1$–$C_4$alkoxy groups, in particular methoxy, methylenedioxy, nitro groups and/or carboxyl groups, which can be free or present in a salt form or as $C_1$–$C_4$alkyl esters, in particular methoxycarbonyl or ethoxycarbonyl. Preferably, the aryl radicals carry not more than 2 substituents, in particular those of the same type, or only a single substituent; in particular, they are unsubstituted. Preferred heterocyclic hydrocarbyl (heterocyclyl) is, for example, that which is analogous to the aryl radicals preferred above and, instead of one or 2 C atoms, contains in each case a heteroatom, in particular nitrogen, such as a pyridyl or quinolyl or quinazolyl, where the free valency is located on a C atom, and can also be substituted accordingly. Preferred carbocyclic-acyclic and heterocyclic-acyclic hydrocarbyl radicals are those in which two or three, but preferably only one, of the cyclic radicals defined above, preferably the unsubstituted radical, is carried by a $C_1$–$C_3$alkyl, all preferably being located on one C atom, preferably the terminal C atom; unsubstituted benzyl is most preferred.

Particularly preferred compounds of the formula I are those in which $R_o$ is $C_1$–$C_7$alkyl, in particular $C_1$–$C_4$alkyl, hydroxy-$C_2$–$C_{18}$alkyl, in particular hydroxy-$C_2$–$C_{14}$alkyl, cyano-$C_1$–$C_7$alkyl, in particular cyano-$C_1$–$C_4$alkyl, carboxy-$C_1$–$C_7$alkyl, in particular carboxy-$C_1$–$C_4$alkyl $C_1$–$C_7$alkoxy-carbonyl-$C_1$–$C_7$alkyl, in particular $C_1$–$C_4$alkoxy-carbonyl-$C_1$–$C_4$alkyl, benzyloxy-carbonyl-$C_1$–$C_7$alkyl, in particular benzyloxycarbonyl-$C_1$–$C_4$alkyl, $C_3$–$C_7$alkenyl, phenyl, naphthyl, pyridyl, quinolyl, or quinazolyl, or phenyl-$C_1$–$C_7$alkyl, in particular phenyl-$C_1$–$C_3$alkyl, it also being possible for the particular aromatic radicals furthermore to be substituted by $C_1$–$C_7$alkyl, in particular $C_1$–$C_4$alkyl, $C_1$–$C_7$alkoxy, in particular $C_1$–$C_4$alkoxy, halogen, nitro, trifluoromethyl or furthermore carboxyl, $C_1$–$C_4$alkoxy-carbonyl, methylenedioxy and/or cyano, the hydroxyl group in the correspondingly substituted alkyl radical being located, in particular, in the 2 position and the cyano, carboxyl, alkoxycarbonyl, benzyloxy-carbonyl or phenyl group in the correspondingly substituted alkyl radical being located, in particular, in the 1 or ω position.

Particularly preferred compounds of the formula I are those in which $R_o$ is $C_1$–$C_4$alkyl, such as methyl or ethyl, hydroxy-$C_2$–$C_{14}$alkyl, such as 2-hydroxy-propyl, -hexyl, -decyl or -tetra-decyl, cyano-$C_1$–$C_4$alkyl, such as 2-cyano-ethyl, carboxy-$C_1$–$C_4$alkyl, such as carboxymethyl, $C_1$–$C_4$alkoxycarbonyl-$C_1$–$C_4$alkyl, such as methoxycarbonyl-methyl or -ethyl, $C_3$–$C_7$-alkenyl, such as allyl, or phenyl, the hydroxyl group in the correspondingly substituted alkyl preferably being located in the 2 position and the cyano, carboxyl or alkoxycarbonyl group being located, in particular, in the 1 or ω position.

Aminoacyl as part of the abovementioned aminoacyl-amino substituent of an aliphatic hydrocarbon radical $R_4$ or $R_5$ is, in particular, the C-terminal radical of an amino acid, such as an α-amino acid, for example one of the naturally occurring α-amino acids, in particular one of the 20 essential α-amino acids which regularly occur in proteins, i.e. glycine, alanine, phenylalanine, proline, valine, leucine, isoleucine, serine, threonine, cysteine, methionine, tyrosine, tryptophan, arginine, histidine, lysine, glutamic acid, glutamine, aspartic acid and asparagine, and in addition phenylglycine. Aminoacyl is preferably amino-lower alkanoyl, which is unsubstituted or substituted by amino, phenyl, hydroxyphenyl, hydroxyl, mercapto, methylthio, indol-3-yl, carbamoyl, carboxyl, guanidino or imidazolyl.

Preferred substituted aliphatic hydrocarbon radicals $R_4$ or $R_5$ without cyclic substituents are, for example, 2-carbamoyl-1-carboxy-eth-1-yl, 3-amino-2-hydroxy-prop-1-yl, 3-amino-prop-1-yl, 3-amino-prop-1-yl, 3-amino-2,2-dimethyl-prop-1-yl, 3-amino-2-oxo-prop-1-yl, 3-amino-1-carboxy-prop-1-yl, 3-amino-3-carboxy-prop-1-yl, 1,1-dicarbamoyl-methyl, 2-carbamoyl-eth-1-yl, 3-amino-1,3-dihydroxylimino-prop-1-yl, 2-carbamoyl-1-hydroxylimino-eth-1-yl, 1-hydroxylimino-2-thiocarbamoyl-eth-1-yl, 3-amino-3-hydroxylimino-1-thio-prop-1-yl, 3-amino-pent-1-yl, 1-amino-pent-3-yl, 1-amidino-1-carbamoyl-methyl, 4-amino-1,1,1,3,5,5,5-heptafluoro-pent-2-yl, 3-amino-1,3-dicarboxy-prop-1-yl, 2-carbamoyl-1-ethoxycarbonyl-eth-1-yl, 2-amino-1,2-dithio-eth-1-yl, 2-amino-1,2-dioxo-eth-1-yl, 2-amino-2-methyl-prop-1-yl, 1-amino-2-methyl-prop-2-yl, 2-amino-prop-1-yl, 1-amino-prop-2-yl, 2-amino-eth-1-yl, 2-amino-2-carboxy-eth-1-yl, 2-amino-1-carboxy-eth-1-yl, carbamoyl-methyl, 1-carbamoyl-3-methyl-but-1-yl, 2-amino-1,2-dicarboxy-eth-1-yl, 1-carbamoyl-3-methylthio-prop-1-yl, 1-carbamoyl-2-methyl-prop-1-yl, 1-carbamoyl-eth-1-yl, 1-carbamoyl-1-cyano-methyl, 1-carbamoyl-3-carboxy-3-fluoro-prop-1-yl, 1-carbamoyl-2-carboxy-eth-1-yl, 2-amino-4-carboxy-but-1-yl, 1-amino-4-carboxy-but-2-yl, 1-carbamoyl-4-guanidino-but-1-yl, 1carbamoyl-5-amino-pent-1-yl, 1-carbamoyl-2-hydroxy-prop-1-yl, 1-carbamoyl-2-methyl-but-1-yl, 1-carbamoyl-2-hydroxy-eth-1-yl, 1,3-dicarbamoyl-prop-1-yl, 2-amino-but-1-yl, 1-amino-but-2-yl, 1-carbamoyl-pent-1-yl, 1-carbamoyl-but-1-yl, 2-hydroxy-ethyl, 3-hydroxy-prop-1-yl, 2-hydroxy-prop-1-yl, 2-hydroxymethyl-prop-2-yl, 1-hydroxy-but-2-yl, 1,3-dihydroxy-prop-2-yl, 2-cyano-ethyl, 2-mercapto-ethyl, 3-amino-2-hydroxy-prop-1-yl, 2-(N-methyl-amino)-ethyl, 2-(2-amino-ethyl-amino)-ethyl, 2-guanidino-ethyl and 2-acetylamino-ethyl.

A carbocyclic-aliphatic radical $R_4$ or $R_5$ can be substituted both in the carbocyclic and in the aliphatic moiety and is, for example, a cycloaliphatic-aliphatic radical, for example cycloalkyl-lower alkyl or -lower alkenyl, for example a methyl, 1- or 2-ethyl, 1- or 2-vinyl, 1-, 2- or 3-propyl or allyl substituted by one of the cycloalkyl radicals mentioned above or below, those substituted at the end of the linear chain being preferred, or an aromatic-aliphatic radical. Preferred carbocyclic-aliphatic radicals $R_4$ or $R_5$ are, for example, benzyl, 2-phenyl-ethyl, 2-amino-benzyl, 3-aminomethyl-benzyl, (1-hydroxy-cyclohex-1-yl)-methyl) (2-amino-3,5,5-trimethyl-cyclopentyl)-methyl, 1-[N-(1-carboxy-2-phenyl-ethyl)-carbamoyl]-2-carbamoyl-eth-1-yl, 1-carbamoyl-1-phenyl-methyl, 1-carbamoyl-2-(4-hydroxy-phenyl)eth-1-yl, 1-carbamoyl-2-phenyl-eth-1-yl, 2-amino-1,2-diphenyl-eth-1-yl, 2-benzyloxycarbonyl-1-carbamoyl-eth-1-yl, 3-benzyloxycarbonyl-1-carbamoyl-prop-1-yl, 1-adamantyl-2-amino-prop-1-yl and 1-adamantyl-1-amino-prop-2-yl.

A heterocyclic-aliphatic radical $R_4$ or $R_5$ can be substituted both in the heterocyclic and in the aliphatic moiety. Preferred heterocyclic-aliphatic radicals $R_4$ or $R_5$ are, for example, (2-furyl)-methyl, (2-tetrahydrofuryl)-methyl, 2-pyrid-2-yl-ethyl, 2-piperidino-ethyl, 2-(morpholin-4-yl)-ethyl, 2-(3-indolyl)ethyl, 2-(4-imidazolyl)-ethyl, 1-carbamoyl-2-(β-indolyl)-eth-1-yl, 1-carbamoyl-2-imidazol-4-yl-eth-1-yl, 1-carbamoyl-2-indol-3-yl-eth-1-yl, 3-aminomethyl-oxetan-3-yl-methyl and 1-(acetoxy-imino)-1-(4-amino-2-oxa-1,3-diazol-5-yl)-methyl.

A carbocyclic radical $R_4$ or $R_5$ having not more than 29 C atoms is such an unsubstituted or substituted hydrocarbon radical, i.e. such a cycloaliphatic or aromatic radical. A carbocyclic hydrocarbon radical is, in particular, a mono-, bi- or polycyclic cycloalkyl, cycloalkenyl or cycloalkadienyl radical, or a corresponding aryl radical. Radicals having not more than 14, in particular 12, ring carbon atoms and 3- to 8-, preferably 5- to 7-, in particular 6-membered rings are preferred, it also being possible for them to carry one or more, for example two, acyclic radicals, for example those mentioned above, and in particular the lower alkyl radicals, or further carbocyclic radicals.

Cycloalkyl represented by the radicals $R_4$ or $R_5$ contains, in particular, 3 not more than and including 10 C atoms and is, for example, cyclopropyl, cyclobutyl, cyclopentyl, cyclohexyl, cycloheptyl and cyclooctyl, as well as bicyclo [2.2.2]octyl, 2-bicyclo[2.2.1]heptyl and adamantyl, which can also be substituted by 1, 2 or more, for example lower, alkyl radicals, in particular methyl radicals; cycloalkenyl is, for example, one of the monocyclic cycloalkyl radicals already mentioned which carries a double bond in the 1, 2 or 3 position. Preferably is C4–C8 cycloalkyl, which is substituted by carboxy, thiocarboxy, lower alkoxycarbonyl, hydrazinocarbonyl, hydroxaminocarbonyl, amidino, sulfamoyl, sulfanyl, halogen, cyano, formyl, amino, hydroxy, lower alkoxy, lower aliphatic acyl, lower alkylamino, di-lower alkylamino, carbamoyl, lower alkylcarbamoyl, aminocarbonyloxy or ureido; most preferably in these cases cycloalkyl is cyclopentyl or cyclohexyl.

An aryl radical represented by the radicals $R_4$ or $R_5$ is, in particular, a phenyl, furthermore a naphthyl, such as 1- or 2-naphthyl, a biphenylyl, such as, in particular, 4-biphenylyl, and moreover also an anthryl, fluorenyl or azulenyl radical, and their aromatic analogues with one or more saturated rings. Preferred aryl-lower alkyl and -lower alkenyl radicals are, for example, phenyl-lower alkyl or phenyl-lower alkenyl with a terminal phenyl radical, such as, for example, benzyl, phenethyl, 1-, 2- or 3-phenyl-propyl, diphenylmethyl (benzhydryl), trityl and cinnamyl, and furthermore also 1- or 2-naphthylmethyl. Aryl radicals which carry acyclic radicals, such as lower alkyl, are, in particular, o-, and m- and p-tolyl and xylyl radicals with methyl radicals in various sites.

Carbocyclic radicals $R_4$ or $R_5$ are, for example, amino-phenyl, such as 2-amino-phenyl, 3-amino-phenyl and 4-amino-phenyl, cyclohexyl, 4-methyl-cyclohexyl, amino-cyclohexyl, such as 2-amino-cyclohex-1-yl, 3-amino-cyclohex-1-yl and 4-amino-cyclohex-1-yl, hydroxy-cyclohexyl, for example 2-hydroxy-cyclohexyl, 3-hydroxy-cyclohexyl and 4-hydroxy-cyclohexyl, 1-(hydroxymethyl)-cyclopent-1-yl, 2-aminomethyl-3,3,5-trimethyl-cyclopent-1-yl, adamant-1-yl, 3-amino-adamantan-1-yl, 2-carbamoyl-bicyclo[2.2.1]hept-5-en-3-yl, 2-carbamoyl-cyclohex-1-yl, 3-carbamoyl-cyclohex-1-yl, 4-carbamoyl-cyclohex-1-yl and 9-amino-spiro[4,4]non-1-yl.

Heterocyclic radicals $R_4$ or $R_5$ having not more than 20 C atoms and not more than 9 heteroatoms are preferably bonded via one of their ring carbon atoms and are, in particular, monocyclic, but also bi- or polycyclic, aza-, thia-, oxa-, thiaza-, oxaza-, diaza-, triaza- or tetrazacyclic radicals of aromatic character, and corresponding partly or, in particular, completely saturated heterocyclic radicals of this type, it being possible for such radicals, where appropriate, for example like the abovementioned carbocyclic or aryl radicals, to carry further acyclic, carbocyclic or heterocyclic radicals and/or to be mono-, di- or polysubstituted by functional groups. In particular, they are unsubstituted or substituted monocyclic radicals with one nitrogen, oxygen or sulfur atom, such as 2-aziridinyl, and in particular aromatic radicals of this type, such as pyrryl, for example 2-pyrryl or 3-pyrryl, pyridyl, for example 2-, 3- or 4-pyridyl, and furthermore thienyl, for example 2- or 3-thienyl, or furyl, for example 2-furyl; analogous bicyclic radicals with one nitrogen, oxygen or sulfur atom are, for example, indolyl, such as 2- or 3-indolyl, quinolyl, such as 2- or 4-quinolyl, isoquinolyl, such as 3- or 5-isoquinolyl, benzofuranyl, such as 2benzofuranyl, chromenyl, such as 3-chromenyl, or benzothienyl, such as 2- or 3-benzothienyl; preferred monocyclic and bicyclic radicals with more than one heteroatom are, for example, imidazolyl, such as 2-imidazolyl, pyrimidinyl, such as 2- or 4-pyrimidinyl, oxazolyl, such as 2-oxazolyl, isoxazolyl, such as 3-isoxazolyl, or thiazolyl, such as 2-thiazolyl, or benzimidazolyl, such as 2-benzimidazolyl, benzoxazolyl, such as 2-benzoxazolyl, or quinazolyl, such as 2-quinazolinyl. Also suitable are corresponding partly or, in particular, completely saturated analogous radicals, such as 2-tetrahydrofuryl, 4-tetrahydrofuryl, 2- or 3-pyrrolidyl, 2-, 3-, or 4-piperidyl, and also 2- or 3-morpholinyl, 2- or 3-thiomorpholinyl, 2-piperazinyl and N,N'-bis-lower alkyl-2-piperazinyl radicals. These radicals can also carry one or more acyclic, carbocyclic or heterocyclic radicals, in particular those mentioned above.

A heterocyclic radical $R_4$ or $R_5$ can be substituted by one, two or more identical or different substituents (functional groups); the following substituents are particularly suitable: free, etherified and esterified hydroxyl groups; mercapto and lower alkylthio and substituted and unsubstituted phenylthio groups; halogen atoms, such as chlorine and fluorine, but also bromine and iodine; oxo groups, which are in the form of formyl (i.e. aldehydo) and keto groups, and also corresponding acetals or ketals; azido and nitro groups; primary, secondary and, preferably, tertiary amino groups, primary or secondary amino groups, acylamino groups and diacylamino groups protected by conventional protective groups, and unmodified or functionally modified sulfo groups, such as sulfamoyl groups or sulfo groups present in salt form. All these functional groups should not be on the C atom from which the free valency comes, and they are preferably separated from it by 2 or even more C atoms. The hetero-cyclic radical can also carry free and functionally modified carboxyl groups, such as carboxyl groups present in salt form or esterified carboxyl groups, carbamoyl, ureido or guanidino groups, which may or may not carry one or two hydrocarbon radicals, and cyano groups.

Preferred heterocyclic radicals $R_4$ or $R_5$ are, for example, 5-amino-2-oxa-1,3-diazol-4-yl, 4-amino-thien-3-yl, 3-carbamoyl-5-(3-[2,4-dichloro-phenyl]-1-oxo-prop-2-en-1-yl)-1,2-thiazol-4-yl, 3-carbamoyl-5-(3-[4-trifluoro-phenyl]-1-oxo-prop-2-en-1-yl)-1,2-thiazol-4-yl, 4-amino-2-(4-carboxy-butyl)-tetrahydrothiophen-3-yl, 3-amino-2-(4-carboxy-butyl)-tetrahydrothiophen-4-yl, [1,2,5]oxadiazolo[3,4-b](6-amino-pyrazin-5-yl), 2,5'-diacetyl-3-amino-thieno[2,3-b]thio-phen-4'-yl and 3-amino-2,5'-dipivaloyl-thieno[2,3-b]thiophen-4'-yl.

A substituted or unsubstituted alkylene or alkenylene radical having in each case not more than 15 C atoms, in which 1–3 C atoms can be replaced by oxygen, sulfur or nitrogen, which is represented by $R_4$ and $R_5$ together, is branched or unbranched and preferably has not more than 10 C atoms, not including the C atoms present in any substituents. Substituents are, for example, those mentioned above for substituted aliphatic hydrocarbon radicals $R_5$. The substituents can be either on a C atom or on oxygen, sulfur or, in particular, nitrogen. Preferred radicals are, for example, 1,2-ethylene, propane-1,3-diyl, butane-1,4-diyl, pentane-1,5-diyl, 3-(3-amino-propionyl)-3-aza-pentane-1,5-diyl, 2-amino-butane-1,4-diyl, 1-aminomethyl-butane-1,4-diyl, 1-hydroxymethyl-butane-1,4-diyl, 3-hydroxy-pentane-1,5-diyl, 1-hydroxy-hexane-1,5-diyl, 3-(2-amino-ethyl)-pentane-1,5-diyl, 3-aza-pentane-1,5-diyl (—CH$_2$—CH$_2$—NH—CH$_2$—CH$_2$—), 3-aza-2,4-dimethyl-pentane-1,5-diyl (—CH$_2$—CH[CH$_3$]—NH—CH[CH$_3$]—CH$_2$—), 3-amino-3-aza-pentane-1,5-diyl (—CH$_2$—CH$_2$—N[NH$_2$]—CH$_2$—CH$_2$—), 1-aza-pentane-1,5-diyl, 1-aza-1-toluylaminocarbonyl-pentane-1,5-diyl, 1-aza-1-(methylamino-thiocarbonyl)-pentane-1,5-diyl, 1-aza-1-(tert-butylamino-carbonyl)-pentane-1,5-diyl, 1-aza-1-(cyclohexylamino-carbonyl)-pentane-1,5-diyl, 3-aza-1-hydroxy-heptane-3,7-diyl, 3-aza-1-cyano-heptane-3,7-diyl, 1-amino-3-aza-heptane-3,7-diyl, 3-(2-amino-ethyl)-3-aza-pentane-1,5-diyl (—CH$_2$—CH$_2$—N[—CH$_2$—CH$_2$—NH$_2$]—CH$_2$—CH$_2$—), 1-carbamoyl-butane-1,4-diyl, 2-formylamino-pentane-1,4-diyl, 2-aza-butadiene-1,4-diyl (—CH=CH—N=CH—), 2-aza-3-hydroxymethyl-butadiene-1,4-diyl (—CH=C[CH$_2$OH]—N=CH—), 2-Aza-1-hydroxy-1-(4-methoxy-phenyl-amino)-heptane-2,7-diyl {—(CH$_2$)$_4$—N[—CH(OH)—NH—C$_6$H$_4$—OCH$_3$]—} or a radical of the formula

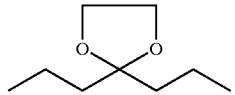

in which the two terminal bonds of the alkylene chain are free valencies.

Salts of compounds of formula I are, in particular, acid addition salts with organic or inorganic acids, in particular the pharmaceutically acceptable, non-toxic salts. Suitable inorganic acids are, for example, carbonic acid (preferably in the form of carbonates or bicarbonates); hydrohalic acids, such as hydrochloric acid; sulfuric acid; or phosphoric acid. Suitable organic acids are, for example, carboxylic, phosphonic, sulfonic or sulfonamic acids, for example acetic acid, propionic acid, octanoic acid, decanoic acid, dodecanoic acid, glycolic acid, lactic acid, 2-hydroxybutyric acid, gluconic acid, glucose monocarboxylic acid, fumaric acid, succinic acid, adipic acid, pimelic acid, suberic acid, azelaic acid, malic acid, tartaric acid, citric acid, glucaric acid, galactaric acid; amino adds, such as glutamic acid, aspartic acid, N-methylglycine, acetylaminoacetic acid, N-acetylasparagine or N-acetyl-cysteine, pyruvic acid, acetoacetic acid, phosphoserine, 2- or 3-glycerophosphoric acid, glucose-6-phosphoric acid, glucose-1-phosphoric acid, fructose-1,6-bisphosphoric acid, maleic acid, hydroxymaleic acid, methylmaleic acid, cyclohexanecarboxylic acid, adamantanecarboxylic acid, benzoic acid, salicylic acid, 1- or 3-hydroxynaphthyl-2-carboxylic acid, 3,4,5-trimethoxybenzoic acid, 2-phenoxybenzoic acid, 2-acetoxybenzoic acid, 4-aminosalicylic acid, phthalic acid, phenylacetic acid, mandelic acid, cinnamic acid, nicotinic acid, isonicotinic acid, glucuronic acid, galacturonic acid, methane- or ethanesulfonic acid, 2-hydroxyethanesulfonic acid, ethane-1,2-disulfonic acid, benzenesulfonic acid, 2-naphthalenesulfonic acid, 1,5-naphthalenedisulfonic acid, 2-, 3- or 4-methylbenzene-sulfonic acid, methylsulfuric acid, ethylsulfuric acid, dodecylsulfuric acid, N-cyclohexyl-sulfamic acid, N-methyl-, N-ethyl- or N-propylsulfamic acid, or other organic protonic acids, such as ascorbic acid.

Compounds of the formula I which carry at least one free carboxyl group can form inner salts or metal or ammonium salts, such as alkali metal or alkaline earth metal salts, for example sodium, potassium, magnesium or calcium salts or ammonium salts with ammonia or suitable organic amines, such as tertiary monoamines, for example triethylamine or tri(2-hydroxyethyl)-amine, or heterocyclic bases, for example N-ethyl-piperidine or N,N'-dimethyl-piperazine.

Pharmaceutically unsuitable salts, for example picrates or perchlorates, can also be used for isolation or purification. Only the non-toxic salts which are pharmaceutically acceptable (at the appropriate doses) are used therapeutically, and are therefore preferred.

As a result of the close relationship between the novel compounds in free form and in the form of their salts, including also those salts which can be used as intermediates, for example during purification of the novel compounds or for their identification, where appropriate the free compounds above and below are to be understood appropriately and expediently as also meaning the corresponding salts.

The compounds of the formula I have valuable pharmacologically useful properties. In particular, they display specific inhibiting actions which are of pharmacological interest.

The compounds of the formula I and their pharmaceutically acceptable salts inhibit the enzyme $p34^{cdc2}$/cyclin $B^{cdc13}$ kinase. In addition to other cdc2-related kinases, this kinase controls certain phases during cell division, in particular the transition from the $G_1$ phase into the S phase, and in particular the transition from the $G_2$ phase into the M phase.

The cycle of a eukaryotic cell comprises, in chronological sequence, the interphase and the M phase. The interphase is accompanied by an enlargement of the cell. It in turn comprises, in chronological sequence, the $G_1$ phase, the S phase and the $G_2$ phase. In the $G_1$ phase (G="gap", i.e. interspace), biosynthetic processes proceed in the cell. In the S phase (synthesis phase), the DNA replicates. The cell then enters the $G_2$ phase, which ends with the start of mitosis.

The M phase in turn comprises, in chronological sequence, division of the cell nucleus (mitosis) and division of the cytoplasm (cytokinesis).

The above-mentioned inhibition of the enzyme $p34^{cdc2}$/cyclin $B^{cdc13}$ kinase can be demonstrated by the following experiment:

Starfish oocytes are induced into the M phase with 10 μM 1-methyl-adenine, frozen in liquid nitrogen and stored at −80° C. The ooctyes are homogenized and centrifuged, as described in D. Arion et al., Cell 55, 371–378 (1988) and V. Rialet und L. Meijer, Anticancer Res. 11, 1581–1590 (1991), as required. For purification of the $p34^{cdc2}$/cyclin $B^{cdc13}$ kinase, the supernatant of the oocytes is introduced onto $p_o^{CKShs}$ Sepharose grains produced from recombinant human protein $p9^{CKShs}$, as described in L. Azzi et al., Eur. J. Biochem. 203, 353–360 (1992). After 30 minutes at 4° C. under constant rotation, the grains are washed thoroughly and the active $p34^{cdc2}$/cyclin $B^{cdc13}$ kinase is eluted with free protein $p9^{CKShs}$ (3 mg/ml). The kinase eluted is tested as described in L. Meijer et al., EMBO J. 8, 2275–2282 (1989) and EMBO J. 10, 1545–1554 (1991), using histone H1 as the substrate. In this test, the compounds of the formula I and their pharmaceutically acceptable salts have an inhibiting concentration $IC_{50}$ [μmol/liter] of 0.0005 to 4, usually of 0.001 to 3.

On the basis of this finding, it can be expected that the compounds of the formula I and their pharmaceutically acceptable salts can be used for treatment of hyperproliferative diseases, such as tumours and psoriasis.

As can already be expected on the basis of the inhibiting action on the enzyme $p34^{ckc2}$/cyclin $B^{cdc13}$ kinase described above, the compounds of the formula I and their pharmaceutically acceptable salts have antiproliferative properties which can be demonstrated directly in another test as follows: here, the inhibiting action of the compounds of the formula I on the growth of human T24 bladder carcinoma cells is determined. These cells are incubated in "Eagle's minimal essential medium", to which 5% (v/v) of foetal calf serum is added, in a humidified incubator at 37° C. and 5 percent by volume $CO_2$ in air. The carcinoma cells (1000–1500) are seeded into 96-well microliter plates and incubated overnight under the abovementioned conditions. The test substance is added in serial dilutions on day 1. The plates are incubated under the abovementioned conditions for 5 days. During this period of time, the control cultures pass through at least 4 cell divisions. After the incubation, the cells are fixed with 3.3% (W/V) aqueous glutaraldehyde solution, washed with water and stained with 0.05% (weight/volume) aqueous methylene blue solution. After washing, the dye is eluted with 3% (W/V) aqueous hydrochloric acid. Thereafter, the optical density (OD) per well, which is directly proportional to the cell count, is measured with a photometer (Titertek multiskan) at 665 nm. The $IC_{50}$ values are calculated with a computer system using the formula $$\frac{OD_{665}(\text{Test}) \text{minus} OD_{665}(\text{Initial})}{OD_{665}(\text{Control}) \text{minus} OD_{665}(\text{Initial})} \times 100.$$

The $IC_{50}$ values are defined as that concentration of active compound at which the number of cells per well at the end of the incubation period is only 50% of the cell count in the control cultures. The $IC_{50}$ values determined in this way are about 0.05 to 20 μmol/liter for the compounds of the formula I and their pharmaceutically acceptable salts.

The antitumoural action of the compounds of the formula I can also be demonstrated in vivo: to determine the antitumoural action, female Balb/c naked mice with subcutaneously transplanted human bladder tumours T24 are used. On day 0, about 25 mg of a solid tumour is pushed under the skin on the left flank of the animals under peroral Forene anaesthesia and the small incision wound is closed by means of wound clamps. On day 6 after the transplant, the mice are divided randomly into groups of 6 animals and treatment is started. The treatment is carried out for 15 days with a single daily peroral or intraperitoneal administration of a compound of the formula I in dimethyl sulfoxide/Tween 80/sodium chloride solution in the various doses. Twice a week, the tumours are measured with a slide gauge and the tumour volume is calculated. In this test, peroral or intraperitoneal administration of a compound of the formula I or of a pharmaceutically acceptable salt thereof causes a significant reduction in the average tumour volume compared with the untreated control animals.

The compounds of the formula I inhibit the activity of the protein tyrosine kinase pp60$^{c-src}$ in concentrations between about 0.001 and about 10 $\mu$M [test description: K. Farley et al., Anal. Biochem. 203 (1992) 151–157; purified enzyme—as described in N. B. Lydon et al., Biochem. J. 287 (1992) 985–993—is used here].

It is known that both a specific change in the c-src gene, which leads to the elimination of c-src, and inhibition of the activity of the protein tyrosine kinase pp60$^{c-src}$ affects the bone resorption capability of osteoclasts [elimination of c-src by genetic manipulation; see, for example, P. Soriano et al., Cell 64 (1991) 693–702; inhibition of the activity of the protein tyrosine kinase pp60$^{c-src}$: see, for example, B. F. Boyce et al., J. Clin. Invest. 90 (1992) 1622–1627; T. Yoneda et al., J. Clin. Invest. 91 (1993) 2791–2795].

The compounds of the formula I are therefore very highly suitable for the treatment of diseases which respond to inhibition of the activity of the protein tyrosine kinase pp60$^{c-src}$. Osteoporosis, in particular, can be mentioned here, and also other diseases in whose course bone resorption by osteoclasts play a part, e.g. tumor-induced hypercalcaemia, Paget's Disease or the treatment of bone metastases, and also inflammatory processes in joints and bones and degeneratives processes in cartilaginous tissue. Moreover, the compounds of formula I are useful for the treatment of benign or malignant tumours which respond to inhibition of the protein tyrosine kinase pp$_{60}$$^{c-src}$, e.g breast cancer (mammary carcinoma) or bowel cancer (carcinoma of the colon). They are able to cause tumour regression and to prevent tumour metastasization and the growth of micrometastases.

Preferably, the compounds of the formula I have a structure, wherein q is 1–5, $R_1$ is α) —S(=O)$_k$—NR$_6$R$_7$, in which k is 1 or 2, wherein under the proviso that $R_6$ and $R_7$ cannot be simultaneously hydrogen α1) $R_6$, $R_7$ can be identical or different from one another and represent an aliphatic, carbocyclic, heterocyclic, carbocyclic-aliphatic or heterocyclic-aliphatic radical; hydrogen or lower aliphatic acyl; or α2) $R_6$ and $R_7$ together are a substituted or unsubstituted alkylene or alkenylene radical, in which 1–3 C atoms can be replaced by oxygen, sulfur or nitrogen,;

β) N-(aryl lower alkyl)carbamoyl;

γ) a radical of the formula —NH—S(=O)$_i$—R$_8$, in which i is 1 or 2, $R_8$ is an aliphatic, carbocyclic or heterocyclic radical; or δ) a radical of the formula —NH—C(=O)—R$_9$, in which $R_9$ is alkoxy, aryloxy, alkenyl, alkynyl, aryl alkynyl, alkynyloxy or aryl alkynyloxy, which in each case is unsubstituted or substituted;

where, if more than one radical $R_1$ is present in the molecule, these can be identical or different from one another, $R_2$ is hydrogen, carbamoyl or N-lower alkyl-carbamoyl, $R_3$ is a lower aliphatic radical, which is unsubstituted or substituted by hydroxy, lower alkoxy, amino, lower alkylamino or N,N-di-lower alkylamino and a) $R_4$ is hydrogen, amino, phenylamino, lower alkylamino, hydroxyl, phenoxy, lower alkoxy, acyl having 1–30 C atoms, a substituted aliphatic hydrocarbon radical having not more than 29 C atoms, a substituted carbocyclic or carbocyclic-aliphatic radical having not more than 29 C atoms or a heterocyclic or heterocyclic-aliphatic radical having not more than 20 C atoms and not more than 9 heteroatoms and $R_5$, independently of $R_4$, is as defined above for $R_4$, with the exception of hydrogen, or b) $R_4$ and $R_5$ together are a substituted or unsubstituted alkylene or alkenylene radical having in each case not more than 15 C atoms, in which 1–3 C atoms can be replaced by oxygen, sulfur or nitrogen.

The invention relates in particular to compounds of the formula I, in which q is 1–5, $R_1$ is α) —S(=O)$_k$—NR$_6$R$_7$, in which k is 1 or 2, wherein under the proviso that $R_6$ and $R_7$ cannot be simultaneously hydrogen α1) $R_6$, $R_7$ can be identical or different from one another and represent an aliphatic, carbocyclic, heterocyclic, carbocyclic-aliphatic or heterocyclic-aliphatic radical; hydrogen or lower aliphatic acyl; or α2) $R_6$ and $R_7$ together are a substituted or unsubstituted alkylene or alkenylene radical, in which 1–3 C atoms can be replaced by oxygen, sulfur or nitrogen;

β) N-(aryl lower alkyl)carbamoyl, or

γ) a radical of the formula —NH—S(=O)$_i$—R$_8$, in which i is 1 or 2, $R_8$ is an aliphatic, carbocyclic or heterocyclic radical; or δ) a radical of the formula —NH—C(=O)—R$_9$, in which $R_9$ is alkoxy, aryloxy, alkenyl, alkynyl, heterocyclyl alkynyl, aryl alkynyl, heteroaryl alkynyl, alkynyloxy or aryl alkynyloxy, which in each case is unsubstituted or substituted; where, if more than one radical $R_1$ is present in the molecule, these can be identical or different from one another, a) $R_4$ is hydrogen, amino, phenylamino, lower alkylamino, hydroxyl, phenoxy, lower alkoxy, acyl having 1–30 C atoms, a substituted aliphatic hydrocarbon radical having not more than 29 C atoms, a substituted carbocyclic or carbocyclic-aliphatic radical having not more than 29 C atoms or a heterocyclic or heterocyclic-aliphatic radical having not more than 20 C atoms and not more than 9 heteroatoms in case of α as defined above and $R_4$ is hydrogen, amino, phenylamino, lower alkylamino, hydroxyl, phenoxy, lower alkoxy, acyl having 1–30 C atoms, a substituted aliphatic hydrocarbon radical having not more than 29 C atoms, a substituted cycloaliphatic or carbocyclic-aliphatic radical having not more than 29 C atoms or a heterocyclic or heterocyclic-aliphatic radical having not more than 20 C atoms and not more than 9 heteroatoms in cases of β, γ and δ as defined above; and $R_5$ is, with the exception of hydrogen and independently of $R_4$, in case of α as defined above for $R_4$ in case of α and in cases of β, γ and δ as defined above for $R_4$ in cases of β, γ and δ, or b) $R_4$ and $R_5$ together are a substituted or unsubstituted alkylene or alkenylene radical having in each case not more than 15 C atoms, in which 1–3 C atoms can be replaced by oxygen, sulfur or nitrogen; or $R_2$ is hydrogen, carbamoyl or N-lower alkyl-carbamoyl, and $R_3$ is a lower aliphatic radical, which is unsubstituted or substituted by hydroxy, lower alkoxy, amino, lower alkylamino or N,N-di-lower alkylamino, and their salts.

Compounds of the formula I which are preferred are those in which q is 1–3, $R_1$ is α) —S(=O)$_k$—NR$_6$R$_7$, in which k is 2, wherein under the proviso that $R_6$ and $R_7$ cannot be simultaneously hydrogen α1) $R_6$, $R_7$ can be identical or different from one another and represent an aliphatic, carbocyclic, heterocyclic, carbocyclic-aliphatic or heterocyclic-aliphatic radical; or hydrogen; or α2) $R_6$ and $R_7$ together are a substituted or unsubstituted alkylene or alkenylene radical, in which 1–3 C atoms can be replaced by oxygen, sulfur or nitrogen, having in each case including the substituents not more than 20 C atoms, or β) N-(aryl lower alkyl)carbamoyl, or γ) a radical of the formula —NH—S(=O)$_i$—R$_8$, in which i is 2, and $R_8$ is an aliphatic, carbocyclic or heterocyclic radical; or δ) a radical of the formula —NH—C(=O)$_i$—R$_9$, in which $R_9$ is alkoxy, aryloxy, alkynyl, heterocyclyl alkynyl, aryl alkynyl, heteroaryl alkynyl, alkynyloxy or aryl alkynyloxy, which in each case is unsubstituted or substituted;

where, if more than one radical $R_1$ is present in the molecule, these can be identical or different from one another, $R_2$ is hydrogen, $R_3$ is a lower alkyl, $R_4$ is hydrogen, amino, phenylamino, lower alkylamino, hydroxyl, phenoxy or lower alkoxy;

an acyl radical of the part formula Z—C(=W)—, in which W is oxygen, sulfur or imino and Z is hydrogen, hydrocarbyl R°, hydrocarbyloxy R°—O— or an amino group of the formula R$_{11}$(R$_{12}$)N—, in which R° in each case is C$_1$–C$_4$alkyl, hydroxy-C$_1$–C$_{14}$alkyl, cyano-C$_1$–C$_4$alkyl, carboxy-C$_1$–C$_4$alkyl, C$_1$–C$_4$alkoxycarbonyl-C$_1$–C$_4$alkyl, C$_3$–C$_7$alkenyl or phenyl and R$_{11}$ and R$_{12}$ independently of one another are each hydrogen, lower alkyl, ω-amino-lower alkyl, lower alkylsulfonyl or phenyl;

an aliphatic hydrocarbon radical having not more than 29 C atoms, which is substituted by halogen, amino, lower alkylamino, ω-amino-lower alkylamino, lower alkanoylamino, benzoylamino, hydroxylamino, hydroxylimino, lower alkoxy-amino, phenyloxyamino, amino-cyclohexyl-amino-, amino-phenyl-amino-, carbamoyl-amino, (N-lower alkyl-carbamoyl)-amino, (N-[ω-amino-lower alkyl]-carbamoyl)-amino, (N-phenyl-carbamoyl)-amino, thio, lower alkylthio, thiocarbamoyl, thioureido, N-lower alkyl-thioureido, N-phenyl-thioureido, guanidino, N-lower alkyl-guanidino, carboxyl, lower alkoxycarbonyl, phenyloxycarbonyl, benzyloxycarbonyl, hydroxylaminocarbonyl, carbamoyl, amidino, cyano, hydroxyl, lower alkoxy, phenyloxy, aminocarbonyl-oxy, oxo, aminosulfonyl, lower alkylsulfonyl-amino, glycylamino, alanylamino, phenylalanylamino, prolylamino, valylamino, leucylamino, isoleucylamino, serylamino, threonylamino, cysteinylamino, methionylamino, tyrosylamino, tryptophanylamino, arginylamino, histidylamino, lysylamino, glutamylamino, glutaminylamino, asparagylamino, asparaginylamino or phenylglycylamino;

benzyl, 2-phenyl-ethyl, 3-aminomethyl-benzyl, (1-hydroxy-cyclohex-1-yl)-methyl, (2-amino-3,5,5-trimethyl-cyclopentyl)-methyl, 1-[N-(1-carboxy-2-phenyl-ethyl)-carbamoyl]-2-carbamoyl-eth-1-yl, 1-carbamoyl-1-phenyl-methyl, 1-carbamoyl-2-(4-hydroxy-phenyl)-eth-1-yl, 1-carbamoyl-2-phenyl-eth-1-yl, 2-amino-1,2-diphenyl-eth-1-yl, 2-benzyloxycarbonyl-1-carbamoyl-eth-1-yl, 3-benzyloxycarbonyl-1-carbamoyl-prop-1-yl, 1-adamantyl-2-amino-prop-1-yl, 1-adamantyl-1-amino-prop-2-yl, (2-furyl)-methyl, (2-tetrahydrofuryl)-methyl, 2-pyrid-2-yl-ethyl, 2-piperidino-ethyl, 2-(morpholin-4-yl)-ethyl, 2-(3-indolyl)-ethyl, 2-(4-imidazolyl)-ethyl, 1-carbamoyl-2-(β-indolyl)-eth-1-yl, 1-carbamoyl-2-imidazol-4-yl-eth-1-yl, 1-carbamoyl-2-indol-3-yl-eth-1-yl, 3-amino-methyl-oxetan-3-yl-methyl, 1-(acetoxy-imino)-1-(4-amino-2-oxa-1,3-diazol-5-yl)-methyl, C4–C8 cycloalkyl, which is substituted by carboxy, thiocarboxy, lower alkoxycarbonyl, hydrazinocarbonyl, hydroxaminocarbonyl, amidino, sulfamoyl, sulfanyl, halogen, cyano, formyl, amino, hydroxy, lower alkoxy, lower aliphatic acyl, lower alkylamino, di-lower alkylamino, carbamoyl, lower alkylcarbamoyl, aminocarbonyloxy or ureido;

2-aminomethyl-3,3,5-trimethyl-cyclopent-1-yl, 3-amino-adamantan-1-yl, 2-carbamoyl-bicyclo[2.2.1]hept-5-en-3-yl, 9-amino-spiro[4.4]non-1-yl, 5-amino-2-oxa-1,3-diazol-4-yl, 4-amino-thien-3-yl, 3-carbamoyl-5-(3-[2,4-dichloro-phenyl]-1-oxo-prop-2-en-1-yl)-1,2-thiazol-4-yl, 3-carbamoyl-5-(3-[4-trifluoro-phenyl]-1-oxo-prop-2-en-1-yl)-1,2-thiazol-4-yl, 4-amino-2-(4-carboxy-butyl)-tetrahydrothiophen-3-yl, 3-amino-2-(4carboxy-butyl)-tetrahydrothiophen-4-yl, [1,2,5]oxadiazolo[3,4-b](6-amino-pyrazin-5-yl), 2,5'-diacetyl-3-amino-thieno[2,3-b]thiophen-4'-yl or 3-amino-2,5'-dipivaloyl-thieno[2,3-b]thiophen-4'yl, and $R_5$, independently of $R_4$, is as defined above for $R_4$, with the exception of hydrogen, or $R_4$ and $R_5$ together are 1,2-ethylene, propane-1,3-diyl, butane-1,4-diyl, pentane-1,5-diyl, 3-(3-amino-propionyl)-3-aza-pentane-1,5-diyl, 1-aminomethyl-butane-1,4-diyl, 1-hydroxy-methyl-butane-1,4-diyl, 3-(2-amino-ethyl)-pentane-1,5-diyl, 3-aza-pentane-1,5-diyl or 3-(2-aminoethyl)-3-aza-pentane-1,5-diyl, and their salts.

The invention relates in particular to a compound of the formula I, wherein q is 1–3, $R_1$ is α) —S(=O)$_k$—NR$_6$R$_7$, in which k is 2, wherein under the proviso that $R_6$ and $R_7$ cannot be simultaneously hydrogen α1) $R_6$, $R_7$ can be identical or different from one another and represent an aliphatic, carbocyclic, heterocyclic, carbocyclic-aliphatic or heterocyclic-aliphatic radical; or hydrogen; or α2) $R_6$ and $R_7$ together are a substituted or unsubstituted alkylene or alkenylene radical, in which 1–3 C atoms can be replaced by oxygen, sulfur or nitrogen, having in each case including the substituents not more than 20 C atoms, or β) N-(aryl lower alkyl)carbamoyl, or γ) a radical of the formula —NH—S(=O)$_i$—R$_8$, in which i is 2, $R_8$ is an aliphatic, carbocyclic or heterocyclic radical; or δ) a radical of the formula —NH—C(=O)—R$_9$, in which $R_9$ is alkoxy, phenoxy, alkynyl or aryl alkynyl which in each case is unsubstituted or substituted;

where, if more than one radical $R_1$ is present in the molecule, these can be identical or different from one another, $R_2$ is hydrogen,
$R_3$ is lower alkyl,
$R_4$ is hydrogen or $C_5$–$C_7$ cycloalkyl, which is substituted by amino, hydroxy, lower alkoxy, lower alkylamino, di-lower alkylamino, carbamoyl, lower alkylcarbamoyl, aminocarbonyloxy or ureido; and
$R_5$, independently of $R_4$, is as defined above for $R_4$, with the exception of hydrogen.

Compounds of the formula I which are preferred are those in which
q is 1–2,
$R_1$ is —S(=O)$_k$—NR$_6$R$_7$, in which k is 2,
wherein under the proviso that $R_6$ and $R_7$ cannot be simultaneously hydrogen,
$R_6$, $R_7$ can be identical or different from one another and represent hydrogen;
$C_1$–$C_{12}$ alkyl which is unsubstituted or substituted by hydroxy, lower alkoxy, halogen, amino, lower alkylamino, di-lower alkylamino, unsubstituted heteroaryl having not more than 10 C atoms and not more than 3 heteroatoms or aryl having not more than 14 C atoms which is unsubstituted or substituted by halogen, lower alkyl, lower alkoxy, phenoxy, lower alkoxycarbonyl, imidazolyl, morpholinyl, pyrrolidinyl, piperidinyl, piperazinyl, amino, lower alkylamino, di-lower alkylamino, carbamoyl or lower alkyl which is substituted by halogen;
$C_3$–$C_{10}$ cycloalkyl which is unsubstituted or substituted by hydroxy, amino, lower alkylamino, di-lower alkylamino, carbamoyl or lower alkylcarbamoyl;
unsubstituted heteroaryl having not more than 20 C atoms and not more than 3 heteroatoms;
aryl having not more than 20 C atoms unsubstituted or substituted by halogen, lower alkyl, lower alkoxy, phenoxy, lower alkoxycarbonyl, imidazolyl, morpholinyl, pyrrolidinyl, piperidinyl, piperazinyl, amino, lower alkylamino, di-lower alkylamino, carbamoyl or lower alkyl which is substituted by halogen; or
$R_6$ and $R_7$ together are a substituted or unsubstituted alkylene or alkenylene radical, in which 1–3 C atoms can be replaced by oxygen or nitrogen, having in each case including the substituents not more than 20 C atoms;
where, if more than one radical $R_1$ is present in the molecule, these can be identical or different from one another,
$R_2$ is hydrogen,
$R_3$ is lower alkyl,
$R_4$ is hydrogen or $C_5$–$C_7$ cycloalkyl, which is substituted by amino, hydroxy, lower alkoxy, lower alkylamino, di-lower alkylamino, carbamoyl, lower alkylcarbamoyl, aminocarbonyloxy or ureido; and
$R_5$, independently of $R_4$, is as defined above for $R_4$, with the exception of hydrogen.

Furthermore, compounds of the formula I which are preferred are those in which $R_1$ is N-(phenyl lower alkyl) carbamoyl, wherein phenyl is unsubstituted or substituted by halogen, lower alkyl, hydroxy, lower alkoxy, phenoxy, amino, lower alkylamino, di-lower alkylamino or lower alkyl which is substituted by halogen; or
$R_1$ is a radical of the formula —NH—S(=O)$_i$—R$_8$, in which i is 2,
$R_8$ is lower alkyl, lower alkyl which is substituted by halogen; $C_3$–$C_8$ cycloalkyl, which is unsubstituted or substituted by halogen, hydroxy, lower alkoxy, amino, lower alkylamino, di-lower alkylamino or carbamoyl; unsubstituted heteroaryl having not more than 20 C atoms and not more than 3 heteroatoms; phenyl which is unsubstituted or substituted by halogen, lower alkyl, hydroxy, lower alkoxy, amino, lower alkylamino, di-lower alkylamino or lower alkyl which is substituted by halogen; or
$R_1$ is a radical of the formula —NH—C(=O)—R$_9$, in which $R_9$ is alkoxy, phenoxy, alkynyl, which is unsubstituted or substituted by tri(lower alkyl)silyl; heteroaryl alkynyl, wherein the heteroaryl moiety comprises one or two heteroatoms selected from the group consisting of nitrogen, sulfur and oxygen, and which radical is unsubstituted or substituted by halogen, hydroxy, lower alkyl, lower alkoxy, phenyl, amino, lower alkylamino, di-lower alkylamino or lower alkyl which is substituted by halogen; heterocyclyl alkynyl, wherein the heterocyclyl moiety comprises one or two heteroatoms selected from the group consisting of nitrogen, sulfur and oxygen, and which radical is unsubstituted or substituted by halogen, hydroxy, lower alkyl, lower alkoxy, phenyl, amino, lower alkylamino, di-lower alkylamino or lower alkyl which is substituted by halogen; or phenyl alkynyl, which is unsubstituted or substituted by halogen, hydroxy, lower alkyl, lower alkoxy, phenyl, amino, lower alkylamino, di-lower alkylamino or lower alkyl which is substituted by halogen;
where, if more than one radical $R_1$ is present in the molecule, these can be identical or different from one another,
$R_2$ is hydrogen,
$R_3$ is lower alkyl,
$R_4$ is hydrogen or $C_5$–$C_7$ cycloalkyl, which is substituted by amino, hydroxy, lower alkoxy, lower alkylamino, di-lower alkylamino, carbamoyl, lower alkylcarbamoyl, aminocarbonyloxy or ureido; and
$R_5$, independently of $R_4$, is as defined above for $R_4$, with the exception of hydrogen.

Compounds of the formula I which are especially preferred are those in which
q is 1,
$R_1$ is
α) —S(=O)$_k$—NR$_6$R$_7$, in which
k is 2,
wherein under the proviso that $R_6$ and $R_7$ cannot be simultaneously hydrogen
α1) $R_6$, $R_7$ can be identical or different from one another and represent hydrogen, $C_1$–$C_8$ alkyl, hydroxy lower alkyl, phenyl unsubstituted or substituted by phenoxy, lower alkoxy, imidazolyl, lower alkyl, halogen, halogen lower alkyl, lower alkyloxycarbonyl, morpholinyl; lower alkyl substituted by phenyl, halogenphenyl, naphthyl, furanyl or pyridyl; $C_3$–$C_6$ cycloalkyl unsubstituted or substituted by hydroxy; tetrahydronaphthyl or chinolinyl; or
α1) $R_6$ and $R_7$ together are an alkylene radical
α1.1) having from 4 up to and including 6 C atoms, in which 1 C atom can be replaced by oxygen; or
α1.2) a radical of the formula (II),

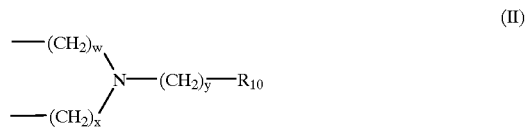

(II)

in which w is 2, x is 2, y is 0 or 1 and $R_{10}$ is hydrogen or phenyl, which is unsubstituted or substituted by halogen, trifluoromethyl or lower alkoxy,
β) unsubstituted or substituted phenyl lower alkylcarbamoyl, in which case phenyl can be substituted by halogen, lower alkyl, lower alkoxy or trifluoromethyl; or
γ) a radical of the formula —NH—S(=O)$_i$—R$_8$,
in which i is 2, and $R_8$ is lower alkyl or phenyl substituted by lower alkyl or lower alkoxy; or δ) a radical of the formula —NH—C(=O)—$R_9$, in which $R_9$ is lower alkoxy, phenoxy, phenyl lower alkynyl, in which phenyl is unsubstituted or substituted by halogen, lower alkyl or lower alkoxy; lower alkynyl or tri(lower alkyl) silyl lower alkynyl, where, if more than one radical $R_1$ is present in the molecule, these can be identical or different from one another, $R_2$ is hydrogen, $R_3$ is lower alkyl, $R_4$ is hydrogen, and $R_5$ is cyclohexyl, which is substituted by amino, hydroxy or carbamoyl.

The invention relates in particular to a compound of the formula I, wherein q is 1, $R_1$ is —S(=O)$_k$—NR$_6$R$_7$, in which k is 2, wherein under the proviso that $R_6$ and $R_7$ cannot be simultaneously hydrogen, $R_6$, $R_7$ can be identical or different from one another and represent hydrogen, $C_1$–$C_8$ alkyl, hydroxy lower alkyl, phenyl unsubstituted or substituted by phenoxy, lower alkoxy, imidazolyl, lower alkyl, halogen, halogen lower alkyl, lower alkyloxycarbonyl, morpholinyl; lower alkyl substituted by phenyl, halogenphenyl, naphthyl, furanyl or pyridyl; $C_3$–$C_6$ cycloalkyl unsubstituted or substituted by hydroxy; tetrahydronaphthyl or chinolinyl; or $R_6$ and $R_7$ together are an alkylene radical having from 4 up to and including 6 C atoms, in which 1 C atom can be replaced by oxygen; or a radical of the formula (II),

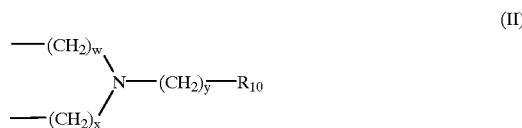

in which w is 2, x is 2, y is 0 or 1 and $R_{10}$ is hydrogen or phenyl, which is unsubstituted or substituted by halogen, trifluoromethyl or lower alkoxy; or unsubstituted or substituted phenyl lower alkylcarbamoyl, in which case phenyl can be substituted by halogen, lower alkyl, lower alkoxy or trifluoromethyl; or a radical of the formula —NH—S(=O)$_i$—$R_8$, in which i is 2, and $R_8$ is lower alkyl or phenyl substituted by lower alkyl or lower alkoxy, or a radical of the formula —NH—C(=O)—$R_9$, in which $R_9$ is lower alkoxy, phenoxy, phenyl lower alkynyl, in which phenyl is unsubstituted or substituted by halogen, lower alkyl or lower alkoxy; lower alkynyl or tri(lower alkyl) silyl lower alkynyl, where, if more than one radical $R_1$ is present in the molecule, these can be identical or different from one another, $R_2$ is hydrogen, $R_3$ is a lower alkyl, $R_4$ is hydrogen, and $R_5$ is cyclohexyl, which is substituted by amino, hydroxy or carbamoyl.

In one embodiment of the invention a compound of the formula I is preferred, wherein q is 1–3, $R_1$ is a radical of the formula —NH—C(=O)—$R_9$, in which $R_9$ is alkoxy, phenoxy, alkynyl, which is unsubstituted or substituted by tri(lower alkyl)silyl; heteroaryl alkynyl, wherein the heteroaryl moiety is selected from the group consisting of pyridyl, pyrimidyl, thienyl, furyl, oxazolyl and thiazolyl and which radical is unsubstituted or substituted by halogen, hydroxy, lower alkyl, lower alkoxy, phenyl, amino, lower alkylamino, di-lower alkylamino or lower alkyl which is substituted by halogen; heterocyclyl alkynyl, wherein the heterocyclyl moiety is selected from the group consisting of piperidinyl, pyrrolidinyl, piperazinyl, lower alkyl piperazinyl, morpholinyl and thiamorpholinyl, and which radical is unsubstituted or substituted by halogen, hydroxy, lower alkyl, lower alkoxy, phenyl, amino, lower alkylamino, di-lower alkylamino or lower alkyl which is substituted by halogen; or phenyl alkynyl, which is unsubstituted or substituted by halogen, hydroxy, lower alkyl, lower alkoxy, phenyl, amino, lower alkylamino, di-lower alkylamino or lower alkyl which is substituted by halogen;

where, if more than one radical $R_1$ is present in the molecule, these can be identical or different from one another, $R_2$ is hydrogen, $R_3$ is lower alkyl, $R_4$ is hydrogen or $C_5$–$C_7$ cycloalkyl, which is substituted by amino, hydroxy, lower alkoxy, lower alkylamino, di-lower alkylamino, carbamoyl, lower alkylcarbamoyl, aminocarbonyloxy or ureido;

$R_5$, independently of $R_4$, is as defined above for $R_4$, with the exception of hydrogen.

More preferably, in this embodiment the compound has a structure of the formula I, wherein q is 1–2, $R_1$ is a radical of the formula —NH—C(=O)—$R_9$, in which $R_9$ is alkoxy, phenoxy, alkynyl, which is unsubstituted or substituted by tri(lower alkyl)silyl; heteroaryl alkynyl, wherein the heteroaryl moiety is selected from the group consisting of pyridyl, pyrimidyl and thienyl, and which radical is unsubstituted or substituted by lower alkyl; heterocyclyl alkynyl, wherein the heterocyclyl moiety is selected from the group consisting of piperidinyl and piperazinyl, and which radical is unsubstituted or substituted by lower alkyl; or phenyl alkynyl, which is unsubstituted or substituted by halogen, hydroxy, lower alkyl, lower alkoxy, phenyl, amino, lower alkylamino, di-lower alkylamino or lower alkyl which is substituted by halogen;

where, if more than one radical $R_1$ is present in the molecule, these can be identical or different from one another, $R_2$ is hydrogen, $R_3$ is lower alkyl, $R_4$ is hydrogen or $C_5$–$C_7$ cycloalkyl, which is substituted by amino, hydroxy, lower alkoxy, lower alkylamino, di-lower alkylamino, carbamoyl, lower alkylcarbamoyl, aminocarbonyloxy or ureido;

$R_5$, independently of $R_4$, is as defined above for $R_4$, with the exception of hydrogen.

The compounds of the formula I and their pharmaceutically acceptable salts are prepared by processes known per se, for example a) for the manufacture of a compound of formula I, wherein $R_1$ is —SO$_k$NR$_6$R$_7$, by reacting a compound of the formula III

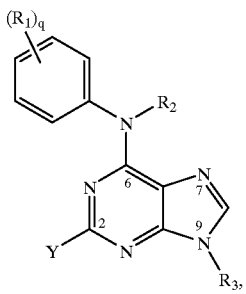

(III)

in which Y is a suitable leaving group, $R_1$ is —$SO_kNR_6R_7$ and the other substituents and symbols are as defined above for compounds of the formula I, free functional groups present in this compound, if necessary, being protected by easily detachable protective groups, with an amine of the formula IV

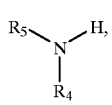

(IV)

in which the substituents are as defined above for compounds of the formula I, free functional groups present in this compound, if necessary, being protected by easily detachable protective groups or, in accordance with the principle of latent functionality, being in a form which can be converted into the functional groups, and detaching the protective groups present and, if necessary, converting functional groups into the final form according to formula I, or b) for the manufacture of a compound of formula I, wherein $R_1$ is N-(aryl lower alkyl) carbamoyl, by reacting a compound of the formula V

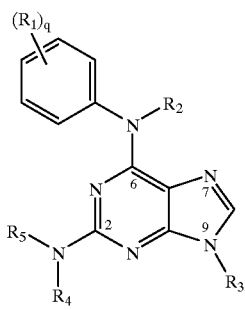

(V)

in which $R_1$ is —$CO_2H$ and the other substituents and symbols are as defined above for compounds of the formula I, free functional groups present in this compound, if necessary, being protected by easily detachable protective groups, with an aryl lower alkyl amine optionally in the presence of a tertiary amine, 1-hydroxybenzotriazole and/or a carbodiimide, such as N-(3-dimethylaminopropyl)-N'-diethylcarbodiimide hydrochloride, free functional groups present in the aryl moiety, if necessary, being protected by easily detachable protective groups, and detaching the protective groups present, or c) for the manufacture of a compound of formula I, wherein $R_1$ is a radical of the formula —NH—S(=O)$_i$—$R_8$ or of the formula —NH—C(=O)—$R_9$, by reacting a compound of the formula V in which $R_1$ is —$NH_2$ and the other substituents and symbols are as defined above for compounds of the formula I, free functional groups present in this compound, if necessary, being protected by easily detachable protective groups, with a compound of the formula VI or VII,

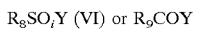

$R_8SO_iY$ (VI) or $R_9COY$ (VII), in which Y is a suitable leaving group and $R_8$ and $R_9$ are as defined above for compounds of the formula I, free functional groups present in $R_8$ or $R_9$, if necessary, being protected by easily detachable protective groups, and detaching the protective groups present, and, after carrying out process a), b) or c), if necessary for the preparation of a salt, converting a resulting free compound of the formula I into a salt or, if necessary for preparation of a free compound, converting a resulting salt of a compound of the formula I into the free compound.

The above processes are described in more detail below:

A suitable leaving group Y in a starting material of the formula III is preferably halogen, such as bromine, iodine or, in particular, chlorine.

The end substances of the formula I can contain substituents which can also be used as protective groups in starting substances for the preparation of other end substances of the formula I. Unless otherwise evident from the context, "protective groups" in this text, are therefore only those easily detachable groups which are not a constituent of the particular desired end substance of the formula I.

Protective groups, their introduction and their detachment are described, for example, in "Protective Groups in Organic Chemistry", Plenum Press, London, New York 1973, and in "Methoden der organischen Chemie" [Methods of Organic Chemistry], Houben-Weyl, 4th Edition, Volume 15/1, Georg-Thieme-Verlag, Stuttgart 1974 and in T. W. Greene, "Protective Groups in Organic Synthesis", John Wiley & Sons, New York 1981. It is characteristic of protective groups that they can be detached easily, i.e. without undesirable side reactions taking place, for example by solvolysis, reduction, photolysis or also under physiological conditions.

Protection of free functional groups in the starting material of the formula III is as a rule not necessary. If desired, free carboxyl or amino groups in the radical $R_1$ or free amino groups in the radical $R_3$ can be protected.

In a starting material of the formula IV, if desired, for example, free amino groups, with the exception of the amino group participating in the reaction, or free carboxyl groups, can be present in protective form. Protection of some functional groups, for example a second amino group in the amine of the formula IV, for example in the case of ethylenediamine, can be avoided by employing the amine of the formula IV in a large excess. Functional groups, such as, in particular, leaving groups, for example halogen or toluenesulfonate, however, can also be present, in accordance with the principle of latent functionality, in a form which can be converted into one of the functional groups according to formula I. Thus, a protected amino group can first be set free by detaching the amino-protective group and the free amino group can then be converted into toluenesulfonate or halogen via an azide in a manner known per se.

A protected amino group can be, for example, in the form of an easily detachable acylamino, arylmethylamino, etherified mercaptoamino or 2-acyl-lower alk-1-en-yl-amino group.

In a corresponding acylamino group, acyl is, for example, the acyl radical of an organic carboxylic acid having, for example, not more than 18 C atoms, in particular an alkanecarboxylic acid which is unsubstituted or substituted, for example by halogen or aryl, or of a benzoic acid which is unsubstituted or substituted, for example by halogen, lower alkoxy or nitro, or of a carbonic acid half-ester. Such acyl groups are, for example, lower alkanoyl, such as formyl, acetyl or propionyl, halo-lower alkanoyl, such as 2-haloacetyl, in particular 2-chloro-, 2-bromo-, 2-iodo-, 2,2,2-trifluoro- or 2,2,2-trichloroacetyl, benzoyl which is unsubstituted or substituted, for example by halogen, lower alkoxy or nitro, for example benzoyl, 4-chlorobenzoyl, 4-methoxybenzoyl or 4-nitrobenzoyl, or lower alkoxycarbonyl which is branched in the 1 position of the lower alkyl radical or suitably substituted in the 1 or 2 position, in particular tert-lower alkoxycarbonyl, for example tert-butyloxycarbonyl, arylmethoxycarbonyl with one or two aryl radicals, which are preferably phenyl which is unsubstituted or mono- or polysubstituted, for example by lower alkyl, in particular tert-lower alkyl, such as tert-butyl, lower alkoxy, such as methoxy, hydroxyl, halogen, for example chlorine, and/or nitro, such as unsubstituted or substituted benzyloxycarbonyl, for example 4-nitro-benzyloxycarbonyl, or unsubstituted or substituted diphenylmethoxycarbonyl, for example benzhydryloxycarbonyl or di-(4-methoxyphenyl)-methoxycarbonyl, aroylmethoxycarbonyl, in which the aroyl group is preferably benzoyl which is unsubstituted or substituted, for example by halogen, such as bromine, for example phenacyloxycarbonyl, 2-halo-lower alkoxycarbonyl, for example 2,2,2-trichloroethoxycarbonyl, 2-bromoethoxycarbonyl or 2-iodoethoxycarbonyl, or 2-(trisubstituted silylethoxycarbonyl, in which the substituents independently of one another are each an aliphatic, araliphatic, cycloaliphatic or aromatic hydrocarbon radical which has not more than 15 C atoms and is unsubstituted or substituted, for example substituted by lower alkyl, lower alkoxy, aryl, halogen or nitro, such as corresponding unsubstituted or substituted lower alkyl, phenyl-lower alkyl, cycloalkyl or phenyl, for example 2-tri-lower alkylsilylethoxycarbonyl, such as 2-trimethylsilylethoxycarbonyl or 2-(di-n-butyl-methyl-silyl)-ethoxycarbonyl, or 2-triarylsilylethoxycarbonyl, such as 2-triphenylsilylethoxycarbonyl.

In an arylmethylamino group which is a mono-, di- or, in particular, triarylmethylamino group, the aryl radicals are, in particular, substituted or unsubstituted phenyl radicals. Such groups are, for example, benzyl-, diphenylmethyl- and, in particular, tritylamino.

An etherified mercapto group in an amino group protected with such a radical is, in particular, arylthio or aryl-lower alkylthio, in which aryl is, in particular, phenyl which is unsubstituted or substituted, for example by lower alkyl, such as methyl or tert-butyl, lower alkoxy, such as methoxy, halogen, such as chlorine, and/or nitro. A corresponding amino-protective group is, for example, 4-nitrophenylthio.

In a 2-acyl-lower alk-1-en-1-yl radical which can be used as an amino-protective group, acyl is, for example, the corresponding radical of a lower alkanecarboxylic acid, of a benzoic acid which is unsubstituted or substituted, for example by lower alkyl, such as methyl or tert-butyl, lower alkoxy, such as methoxy, halogen, such as chlorine, and/or nitro, or, in particular, of a carbonic acid half-ester, such as a carbonic acid lower alkyl half-ester. Corresponding protective groups are, in particular, 1-lower alkanoyl-prop-1-en-2-yl, for example 1-acetyl-prop-1-en-2-yl, or 1-lower alkoxycarbonyl-prop-1-en-2-yl, for example 1-ethoxycarbonhl-prop-1-en-2-yl.

Preferred amino-protective groups are acyl radicals of carbonic acid half-esters, in particular tert-butyloxycarbonyl, benzyloxycarbonyl which is unsubstituted or substituted, for example as defined, for example 4-nitro-benzyloxycarbonyl, or diphenylmethoxycarbonyl, or 2-halo-lower alkoxycarbonyl, such as 2,2,2-trichlorethoxycarbonyl, and furthermore trityl or formyl.

Preferred protected carboxyl groups are, for example, tert-butoxycarbonyl, benzyloxycarbonyl or diphenylmethoxycarbonyl which are unsubstituted or substituted, or 2-trimethylsilyl-ethoxycarbonyl.

The reaction between the derivative of the formula III and the amine derivative of the formula IV can be carried out in suitable inert solvents. If possible, on the basis of the physical nature of the amine of the formula IV, however, the reaction Is carried out without a foreign solvent, and the amine of the formula IV is employed in a large excess, for example a hundred times the equivalent amount, both as the reagent and as the solvent. Depending on the nature of the specific reactants, such as, in particular, the precise nature of the leaving group Y and the reactivity of the specific amine of the formula IV, the reaction is carried out at between 20° C. and 200° C., preferably between +50° C. and +180° C., for example under reflux. If Y is chlorine and the amine of the formula IV is a cycloaliphatic amine, such as 2-amino-4-cyclohexane carboxamide, the reaction is preferably carried out between +80° C. and +170° C., for example at a bath temperature of +160° C. Optionally it is carried out in a high pressure tube.

The protective groups which are not a constituent of the desired end product of the formula I are detached in a manner known per se, for example by means of solvolysis, in particular hydrolysis, alcoholysis or acidolysis, or by means of reduction, in particular hydrogenolysis or chemical reduction, if necessary in stages or simultaneously.

A protected amino group is set free in a manner known per se and, depending on the nature of the protective groups, in diverse manners, preferably by means of solvolysis or reduction. 2-Halo-lower alkoxycarbonylamino (if appropriate after conversion of a 2-bromo-lower alkoxycarbonylamino group into a 2-iodo-lower alkoxycarbonylamino group), aroylmethoxycarbonylamino or 4-nitrobenzyloxycarbonylamino can be split, for example, by treatment with a suitable chemical reducing agent, such as zinc in the presence of a suitable carboxylic acid, such as aqueous acetic acid. Aroylmethoxycarbonylamino can also be split by treatment with a nucleophilic, preferably salt-forming reagent, such as sodium thiophenolate, and 4-nitrobenzyloxycarbonylamino can also be split by treatment with an alkali metal dithionite, for example sodium dithionite. Substituted or unsubstituted diphenylmethoxycarbonylamino, tert-lower alkoxycarbonylamino or 2-trisubstituted silylethoxycarbonylamino can be split by treatment with a suitable acid, for example formic or trifluoroacetic acid, substituted or unsubstituted benzyloxycarbonylamino can be split, for example, by means of hydrogenolysis, i.e. by treatment with hydrogen in the presence of a suitable hydrogenation catalyst, such as a palladium catalyst, and triarylmethylamino or formylamino can be split, for example, by treatment with an acid, such as a mineral acid, for example hydrochloric acid, or an organic acid, for example formic, acetic or trifluoroacetic acid, if appropriate in the presence of water, and an amino group protected by an organic silyl group can be set free, for example, by means of hydrolysis or alcoholysis. An amino group protected by 2-haloacetyl, for example 2-chloroacetyl, can be set free by treatment with thiourea in the presence of a base or with a thiolate salt, such as an alkali metal thiolate, of urea and subsequent solvolysis, such as alcoholysis or hydrolysis, of the condensation product formed. An amino group protected by 2-substituted silylethoxycarbonyl can also be converted into the free amino group by treatment with a hydrofluoric acid salt which supplies fluoride anions.

The starting material of the formula III in which Y is chlorine is obtained in two stages as follows:

In the first stage, 2,6-dichloro-purine, which is commercially obtainable (for example from Lancaster, Aldrich or Fluka) and is in the form of a mixture of the tautomeric forms 2,6-dichloro-9H-purine and 2,6-dichloro-7H-purine, is reacted with an amine of the formula VIII

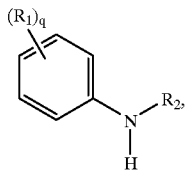

(VIII)

in which q and $R_2$ are as defined above and $R_1$ is hydrogen, —$CO_2Me$ or —$NO_2$, to give a compound of the formula IX

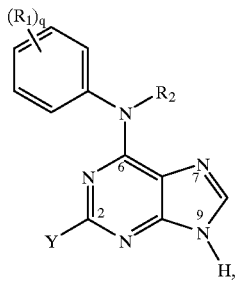

(IX)

in which Y is chlorine, $R_1$ is hydrogen, —$CO_2Me$ or —$NO_2$ and the other substituents and symbols are as defined for formula I. This reaction is carried out in an inert organic solvent, such as, in particular, an alkanol, for example pentanol, preferably at a temperature between room temperature and +150° C., for example at a bath temperature of 100° C., an excess, for example 3–4 times the equivalent amount, of the amine of the formula VIII preferably being employed.

In the second stage, the compound of the formula IX is reacted with a compound of the formula X, $R_3$—Y (X), to give a compound of the formula III in which Y is chlorine.

A suitable leaving group Y in a starting material of the formula X is preferably halogen, such as chlorine, bromine or, in particular, iodine.

The starting material of the formula III in which Y is another leaving group, i.e. different from chlorine, is obtained in an analogous manner.

In case of $R_1$ is hydrogen in formula III, VIII and IX the compound of formula III is then first reacted with $ClHSO_3$ to give a compound III with $R_1$ is —$SO_2Cl$ and thereafter with an amine $HNR_6R_7$ to give a compound of formula III in which $R_1$ is —$SO_2NR_6R_7$.

In case of $R_1$ is —$NO_2$ in formula III, VIII and IX the compound of formula III is reacted with hydrazine monohydrate in the presence of a hydrogenation catalyst, such as Raney Nickel, to give a compound of formula III in which $R_1$ is amino.

In case of $R_1$ is —$CO_2Me$ in formula III, VIII and IX the compound of formula III is hydrolysed in the presence of an alkaline earth metal or alkali metal hydroxide, such as lithium hydroxid, in alkanolic solution to give a compound of formula III in which $R_1$ is —$CO_2H$.

General Process Conditions:

Free compounds of the formula I which are obtainable by the process and have salt-forming properties can be converted into their salts in a manner known per se, for example by treatment with acids or suitable derivatives thereof, for example by addition of the acid in question to the compound of the formula I dissolved in a suitable solvent, for example an ether, such as a cyclic ether, in particular dioxane, and especially tetrahydrofuran. Compounds of the formula I with acid groups, for example free carboxyl groups, are treated, for example, with a suitable base, for example a hydroxide, carbonate or bicarbonate, for salt formation.

Isomer mixtures obtainable according to the invention can be separated into the individual isomers in a manner known per se, for example racemates can be separated by formation of salts with optically pure salt-forming reagents and preparation of the diastereomer mixture thus obtained, for example by means of fractional crystallization.

The abovementioned reactions can be carried out under reaction conditions known per se, in the absence or, usually, presence of solvents or diluents, preferably those which are inert towards the reagents used and dissolve these, in the absence or presence of catalysts, condensation agents (for example phosphorus pentoxide) or neutralizing agents, for example bases, in particular nitrogen bases, such as triethylamine hydrochloride, depending on the nature of the reaction and/or of the reaction participants, at a reduced, normal or elevated temperature, for example in the temperature range from about –80° C. to about 200° C., preferably from about –20° C. to about 150° C., for example at the boiling point of the solvent used, under atmospheric pressure or in a closed vessel, if appropriate under pressure, and/or in an inert atmosphere, for example under a nitrogen atmosphere.

The reaction conditions stated specifically in each case are preferred.

Solvents and diluents are, for example, water, alcohols, for example lower alkylhydroxides, such as methanol, ethanol, propanol or, in particular, butanol, diols, such as ethylene glycol, triols, such as glycerol, or aryl alcohols, such as phenol, acid amides, for example carboxylic acid amides, such as dimethylformamide, dimethylacetamide or 1,3-dimethyl-3,4,5,6-tetrahydro-2(1H)-pyrimidinone (DMPU), carboxylic acids, in particular formic acid or acetic acid, amides of inorganic acids, such as hexamethylphosphoric acid triamide, ethers, for example cyclicethers, such as tetrahydrofuran or dioxane, or acyclic ethers, such as diethyl ether or ethylene glycol dimethyl ether, halogenated hydrocarbons, such as halo-lower alkanes, for example methylene chloride or chloroform, ketones, such as acetone, nitrites, such as acetonitrile, acid anhydrides, such as acetic anhydride, esters, such as ethyl acetate, bisalkanesulfines, such as dimethyl sulfoxide, nitrogen-containing heterocyclic compounds, such as pyridine, hydrocarbons, for example lower alkanes, such as heptane, or aromatics, such as benzene, toluene or xylene(s), or mixtures of these solvents, it being possible for the suitable solvents to be chosen in each case for the abovementioned reactions.

The customary processes are used for working up the compounds of the formula I which can be obtained or their salts, for example solvolysis of excess reagents; recrystallization; chromatography, for example partition, ion or gel chromatography; partition between an inorganic and organic solvent phase; one or several extractions, in particular after acidification or increasing the basicity or the salt content; drying over hygroscopic salts; digestion; filtration; washing; dissolving; evaporation (if necessary in vacuo or under a high vacuum); distillation; crystallization, for example of the resulting compounds in the form of an oil or from the mother liquor, it also being possible for the product to be seeded with a crystal of the end product; or a combination of two or more of the working up steps mentioned, which can also be employed repeatedly.

Starting materials and intermediates can be used in the pure form for example after working up, as mentioned last, in partly purified form or else, for example, directly as a crude product.

As a result of the close relationship between the compounds of the formula I in the free form and in the form of salts, the free compounds and their salts above and below are to be understood appropriately and expediently, where appropriate, as also meaning the corresponding salts or free compounds if the compounds contain salt-forming groups.

The compounds, including their salts, can also be obtained in the form of hydrates, or their crystals can include, for example, the solvent used for the crystallization.

Those starting substances which lead to the novel compounds of the formula I described above as particularly valuable are preferably employed in the process of the present invention.

The invention also relates to those embodiment forms of the process in which a compound obtainable as an intermediate at any process stage is used as the starting substance and the missing process steps are carried out, or in which a starting substance is formed under the reaction conditions or is used in the form of a derivative, for example a salt thereof.

The invention also relates to the compounds of the formula III

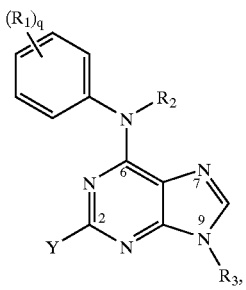

(III)

in which Y is a suitable leaving group, $R_1$ is $—SO_2NR_6R_7$ and the other substituents and symbols are as defined above for compounds of the formula I, free functional groups therein being protected, if necessary, by easily detachable protective groups, which can be used as starting material for the preparation of the compounds of the formula I.

The invention also relates to the compounds of the formula V

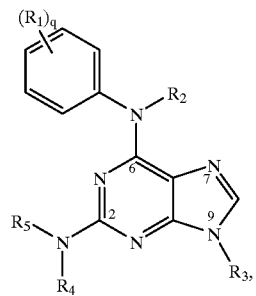

(V)

in which $R_1$ is $CO_2H$ and the other substituents and symbols are as defined above for compounds of the formula I, free functional groups present therein being protected, if necessary, by easily detachable protective groups, as starting material for the preparation of the compounds of the formula I.

The invention also relates to pharmaceutical compositions for use in a method for therapeutic treatment of the human or animal body, a process for the preparation thereof (in particular as compositions for tumour treatment) and a method for treatment of tumour diseases, in particular those mentioned above, and osteoporosis.

The invention relates in particular to a method of treating warm-blooded animals suffering from a proliferative disease, especially a tumor disease and in particular such a disease which responds to inhibition of $p34^{cdc2}$/cyclin $B^{cdc13}$, which method comprises administering, to warm-blooded animals requiring such treatment, an amount that is effective in inhibiting tumors of a compound of formula I or of a pharmaceutically acceptable salt thereof, or the use of a compound of the formula I for such treatment. The invention relates also to the use of a compound of formula I or of a pharmaceutically acceptable salt thereof in the inhibition of protein kinase C in warm-blooded animals or in the preparation of pharmaceutical compositions for use in the therapeutic treatment of the human or animal body. Depending on the species, age, individual condition, mode of administration and the particular clinical picture, effective doses, for example daily doses of approximately 0.1 to about 5 g, preferably about 0.5 to about 2 g, of a compound of the present invention are administered to a warm-blooded animal of approximately 70 kg body weight.

The invention relates also to pharmaceutical compositions comprising an effective amount, especially an amount effective in the prophylaxis or treatment of one of the above-mentioned disorders, of the active ingredient together with pharmaceutically acceptable carriers that are suitable for topical, enteral, for example oral or rectal, or parenteral administration and that may be inorganic or organic, solid or liquid. There are used for oral administration especially tablets or gelatin capsules that comprise the active ingredient together with diluents, for example lactose, dextrose, sucrose, mannitol, sorbitol, cellulose and/or glycerol, and/or lubricants, for example silica, talc, stearic acid or salts thereof, such as magnesium or calcium stearate, and/or polyethylene glycol. Tablets may also comprise binders, for example magnesium aluminum silicate, starches, such as corn, wheat or rice starch, gelatin, methylcellulose, sodium carboxymethylcellulose and/or polyvinylpyrrolidone, and, if desired, disintegrators, for example starches, agar, alginic acid or a salt thereof, such as sodium alginate, and/or effervescent mixtures, or adsorbents, dyes, flavorings and sweeteners. It is also possible to use the pharmacologically active compounds of the present invention in the form of parenterally administrable compositions or in the form of infusion solutions. Such solutions are preferably isotonic aqueous solutions or suspensions which, for example in the case of lyophilized compositions that comprise the active ingredient alone or together with a carrier, for example mannitol, can be made up prior to use. The pharmaceutical compositions may be sterilized and/or may comprise excipients, for example preservatives, stabilisers, wetting agents and/or emulsifiers, solubilisers, salts for regulating the osmotic pressure and/or buffers. The present pharmaceutical compositions, which may, if desired, comprise other pharmacologically active substances, such as antibiotics, are prepared in a manner known per se, for example by means of conventional mixing, granulating, confectioning, dissolving or lyophilising processes, and comprise approximately from 1% to 95%, especially from approximately 1% to approximately 20%, active ingredient(s).

The following Examples serve to illustrate the invention without limiting the scope thereof.

The short names and abbreviations used have the following meanings:
Abbreviations:

abs. absolute (anhydrous)

| | |
|---|---|
| APCI-MS: | "atmospheric pressure chemical ionization" mass spectrum |
| brine | saturated sodium chloride solution |
| decomp. | decomposition |
| diglyme | diethylene glycol dimethyl ether |
| DMF | dimethylformamide |
| DMSO | dimethyl sulfoxide |
| EDC | N-(3-dimethylaminopropyl)-N'-diethylcarbodiimide hydrochloride |
| ESI-MS | electrospray ionisation mass spectrum |
| EtOAc | ethyl acetate |
| h | hour(s) |
| HOBT | 1-hydroxybenzotriazole |
| HPLC | high pressure liquid chromatography |
| HV | high vacuum |
| min | minute(s) |
| m.p. | melting point |
| Me | methyl |
| MS | mass spectroscopy |
| RT | room temperature |
| soln. | solution |
| sat. | saturated |
| TLC-$R_f$ | $R_f$ value according to thin layer chromatography |
| $t_{ret}$ | retention time |
| Abbreviations for the NMR spectra data | |
| b | broad |
| d | doublet |
| J | coupling constant |
| m | multiplet |
| q | quartet |
| s | singlet |
| t | triplet |
| ppm | parts per million |
| TMS | tetramethylsilan |

EXAMPLE 1

0.7 mmoles of 6-(4-butyl-aminosulfonyl-phenyl-amino)-2chloro-9-ethyl-9H-purine are mixed with 1 ml of diglyme and 250 mg of cis-2-amino-cyclohexanecarboxamide (1.7 mmol) in a high-pressure tube. The flask is flushed with argon and kept at 160° C. under magnetic stirring during 18 h. After cooling to RT, the crude mixture is diluted with methanol and the solvents are removed under HV. The resulting solid is dissolved in $CH_2Cl_2$, washed with water (2×25 ml) and with 25 ml of a saturated NaCl soln. The aqueous layers are extracted with $CH_2Cl_2$ (2×100 ml). The combined organic layers are dried ($MgSO_4$), filtered and concentrated. After purification by chromatography (silica gel, $CH_2Cl_2$/MeOH: 95/5) the desired product cis-2-[6-(4-butyl-aminosulfonyl-phenylamino)-9-ethyl-9H-purin-2-yl-amino]-cyclohexanecarboxylic acid amide is obtained (32% yield) as a crystalline powder. $R_f$=0.43 ($CH_2Cl_2$/MeOH (9/1)+1% $NH_3$); m.p. 220° C.; ESI-MS: 515 (M+H)$^+$.

Stage 1.1:

To a solution of 2,6-dichloropurine (20 g, 106 mmol) in 400 ml of ethanol are added 36.5 ml of aniline (400 mmol) and the resulting solution is kept at 50° C. under magnetic stirring for 12 h. After cooling to RT, the mixture is filtered, washed with 2×50 ml of ethanol and dried at 50° C. under HV to give 2-chloro-6-(phenyl-amino)-purine as a yellow powder (25.5 g, 104 mmoles) in 98% yield. $R_f$=0.57 ($CH_2Cl_2$/MeOH (95/5); m.p. decomp. >290° C.; ESI-MS: 246 (M+H)$^+$; $^1$H—NMR ($d_6$-DMSO, 200 MHz, TMS): 7.1 ppm (t, 1H, J=8 Hz, $H_6$), 7.35 ppm (t, 2H, J=8 Hz, $H_5$), 7.8 ppm (d, 2H, J=8 Hz, $H_4$), 8.3 ppm (s, 1H, $H_2$), 10.1 ppm (s, 1H, $H_3$), Stage 1.2:

A one liter flask is charged with 25.5 g of 2chloro-6-(phenyl-amino)-purine (104 mmol), 16.7 g of $K_2CO_3$ (121 mmoles) and 500 ml of DMF. The mixture is stirred for one hour to solubilize $K_2CO_3$, followed by addition of ethyliodid (16.1 ml, 200 mmoles). The flask is stirred at RT for 2 hours under argon. Upon completion, the solvent is removed by evaporation under reduced pressure, and the remaining powder is extracted with 150 ml of ethyl acetate, washed with water (3×30 ml) and with 30 ml of a saturated NaCl soln. The aqueous layers are extracted with ethyl acetate (2×150 ml). The combined organic layers are dried ($MgSO_4$), filtered and concentrated. The crude product is stirred with 100 ml of diethyl ether to give a crude yellow powder, which is filtered and dried at 50° C. under HV. 23.08 g (84 mmol, 81% yield) of 2-chloro-9-ethyl-6-(phenyl-amino)-9H-purine are obtained as a white crystalline powder. $R_f$=0.65 ($CH_2Cl_2$/MeOH (95/5); m.p. 158° C.; ESI-MS: 274 (M+H)$^+$; $^1$H-NMR ($d_6$-DMSO, 200 MHz, TMS): 1.4 ppm (t, 3H, $J_1$=7 Hz, $H_1$), 4.2 ppm (q, 2H, $J_1$=7 Hz, $H_2$), 7.1 ppm (t, 1H, $J_2$=8 Hz, $H_7$), 7.4 ppm (t, 2H, $J_2$=8 Hz, $H_6$), 7.85 ppm (d, 2H, $J_2$=8 Hz, $H_5$), 8.3 ppm (s, 1H, $H_3$), 10.3 ppm (s, 1H, $H_4$).

Stage 1.3:

A three necked round bottomed flask of 250 ml equipped with a bubbler (NaOH) and a magnetic stirrer is charged with 32.2 ml of 98% chlorosulfonic acid (483 mmoles) and cooled to 0° C. 22 g of 2-chloro-9-ethyl-6-(phenyl-amino)-9H-purine (80 mmoles) are added slowly. The mixture is stirred at RT for 2 hours and at 60° C. for 1 hour. The crude mixture is then poured drop by drop into a water bath cooled to 0° C., filtered and dried at 50° C. under HV. 26.67 g (89% yield) of 2-chloro-6-(4-chlorosulfonyl-phenyl-amino)-9-ethyl-9H-purine are obtained as a white crystalline powder. $R_f$=0.52 ($CH_2Cl_2$/MeOH (95/5); m.p. decomp. 220° C.; ESI-MS: 372 (M+H)$^+$; $^1$H-NMR ($d_6$-DMSO, 200 MHz, TMS): 1.4 ppm (t, 3H, $J_1$=7 Hz, $H_1$), 4.2 ppm (q, 2H, $J_1$=7 Hz, $H_2$), 7.55 ppm (d, 2H, $J_2$=9 Hz, $H_5$), 7.75 ppm (d, 2H, $J_2$=9 Hz, $H_6$), 8.55 ppm (s, 1H, $H_3$), 10.5 ppm (s, 1H, $H_4$).

Stage 1.4:

To a solution of 2-chloro-6-(4-chlorosulfonyl-phenyl-amino)-9-ethyl-9H-purine (745 mg, 2 mmol) in 50 ml of $CH_2Cl_2$ are added 8 mmol of butylamine, and the resulting solution is kept at RT under magnetic stirring for 50 hours. Upon completion of the reaction, the crude mixture is washed with water (2×30 ml) and with 30 ml of a saturated NaCl soln. The aqueous layers are extracted with CH$_2$Cl$_2$ (2×50 ml). The combined organic layers are dried (MgSO$_4$), filtered, concentrated and dried at 50° C. under HV to give 6-(4-N-butylamino-sulfonyl-phenyl-amino)-2-chloro-9-ethyl-9H-purine (626 mg, 77% yield) as a crystalline powder. R$_f$=0.50; (CH$_2$Cl$_2$/MeOH (95/5); m.p. 218° C.; ESI-MS: 409 (M+H)$^+$.

EXAMPLES 2 TO 71

Analogously to Example 1 Examples 2 to 71 are obtained.

| Ex Nr. | compound | m.p. [° C.] | R$_f$ | HPLC t$_{Ret}$ (min) | APCI [M + 1]$^+$ |
|---|---|---|---|---|---|
| 1 | cis-2-[6-(4-Butyl-aminosulfonyl-phenylamino)-9-ethyl-9H-purin-2-yl amino]-cyclohexanecarboxylic acid amide | 220 | 0.43$^{a)}$ | 11.31$^{d)}$ | 515 |
| 2 | cis-2-{9-Ethyl-6-[4-(3-methylbutyl)-aminosulfonyl-phenylamino]-9H-purin-2-yl-amino}-cyclohexanecarboxylic acid amide | 239 | 0.31$^{b)}$ | 9.58$^{d)}$ | 529 |
| 3 | cis-2-[9-Ethyl-6-(4-isobutyl-amino sulfonyl-phenylamino)-9H-purin-2-yl amino]-cyclohexanecarboxylic acid amide | 258 | 0.40$^{b)}$ | 11.32$^{d)}$ | 515 |
| 4 | cis-2-{9-Ethyl-6-[4-(4-phenyl-piperazin-1-yl-sulfonyl)-phenylamino]-9H-purin-2-yl-amino}-cyclohexanecarboxylic acid amide | 192 | 0.40$^{b)}$ | | 604 |
| 5 | 4-[2-(trans-4-Amino-cyclohexylamino)-9-ethyl-9H-purin-6-yl-amino]-phenyl-N-(3 methyl-butyl)-sulfonamide | 150 | 0.30$^{a)}$ | 10.08$^{d)}$ | 501 |
| 6 | 4-[2-(trans-4-Amino-cyclohexylamino)-9-ethyl-9H-purin-6-yl-amino]-phenyl-N-butyl-sulfonamide | 116 | 0.18$^{a)}$ | 9.66$^{d)}$ | 487 |
| 7 | 4-[2-(trans-4-Amino-cyclohexylamino)-9-ethyl-9H-purin-6-yl-amino]-phenyl-N-isobutyl-sulfonamide | 132 | 0.25$^{b)}$ | 9.65$^{d)}$ | 487 |
| 8 | 4-[2-(trans-4-Amino-cyclohexylamino)-9-ethyl-9H-purin-6-yl-amino]-phenyl-N-cyclohexyl-sulfonamide | 173 | 0.07$^{c)}$ | 8.56$^{d)}$ | 513 |
| 9 | cis-2-[6-(4-Cyclohexyl-aminosulfonyl-phenylamino)-9-ethyl-9H-Purin-2-yl-amino]-cyclohexanecarboxylic acid amide | 270 | 0.20$^{c)}$ | 12.18$^{d)}$ | 541 |
| 10 | N-2-(trans-4-Amino-cyclohexyl)-9-ethyl N-6-[4-(piperidine-1-sulfonyl)-phenyl]-9H-purine-2,6-diamine | 138 | 0.05$^{c)}$ | 8.16$^{d)}$ | 499 |
| 11 | cis-2-{9-Ethyl-6-[4-(piperidine-1-sulfonyl)-phenyl amino]-9H-purin-2-yl-amino}-cyclohexanecarboxylic acid amide | | 0.38$^{b)}$ | 10.35$^{d)}$ | 527 |
| 12 | cis-2-{6-[4-(N-Butyl-N-methyl-amino-sulfonyl)-phenylamino]-9-ethyl-9H-purin-2-yl-amino}-cyclohexanecarboxylic acid amide | 124 | 0.20$^{c)}$ | 11.00$^{d)}$ | 529 |
| 13 | 4-[2-(trans-4-Amino-cyclohexylamino)-9-ethyl-9H-purin-6-yl-amino]-phenyl-N-butyl-N-methyl-sulfonamide | 154 | 0.06$^{c)}$ | 10.48$^{d)}$ | 501 |
| 14 | cis-2-{9-Ethyl-6-[4-(N-methyl-N-phenyl-aminosulfonyl)-phenylamino]-9H-purin-2-yl-amino)-cyclohexanecarboxylic acid amide | | 0.47$^{b)}$ | 10.74$^{d)}$ | 549 |
| 15 | 4-[2-(trans-4-Amino-cyclohexylamino)-9-ethyl-9H-purin-6-yl-amino]-phenyl-N-methyl-N-phenyl-sulfonamide | 144 | 0.44$^{c)}$ | 8.95$^{d)}$ | 521 |
| 16 | N-2-(trans-4-Amino-cyclohexyl)-9-ethyl-N-6-[4-(4-phenyl-piperazine-1-sulfonyl)-phenyl]-9H-purine-2,6-diamine | | 0.16$^{a)}$ | 7.98$^{d)}$ | 576 |
| 17 | 4-[9-Ethyl-2-(trans-4-hydroxy-cyclohexylamino)-9H-purin-6-yl-amino]-phenyl-N-isobutyl-N-methyl-sulfonamide | | | 5.78$^{e)}$ | 502 |
| 18 | trans-4-(9-Ethyl-6-{4-[4-(4-fluoro-phenyl)-piperazine-1-sulfonyl]-phenylamino}-9H-purin-2-yl-amino)-cyclohexanol | | | 4.98$^{e)}$ | 595 |
| 19 | trans-4-(9-Ethyl-6-{4-[4-(3-trifluoromethyl-phenyl)-piperazine-1-sulfonyl]-phenylamino}-9H-purin-2-yl-amino)-cyclohexanol | | | 5.69$^{e)}$ | 645 |

-continued

| Ex Nr. | compound | m.p. [° C.] | $R_f$ | HPLC $t_{Ret}$ (min) | APCI $[M + 1]^+$ |
|---|---|---|---|---|---|
| 20 | trans-4-(9-Ethyl-6-{4-[4-(2-methoxy-phenyl)-piperazine-1-sulfonyl]-phenylamino)-9H-purin-2-yl-amino)-cyclohexanol | | | 4.43[e] | 607 |
| 21 | N-Cyclohexyl-{4-[9-ethyl-2-(trans-4-hydroxy-cyclohexylamino)-9H-purin-6-yl-amino]-phenyl}-N-methyl-sulfonamide | | | 4.93[e] | 528 |
| 22 | trans-4-{9-Ethyl-6-[4-(pyrrolidine-1-sulfonyl)-phenylamino]-9H-purin-2-yl-amino}-cyclohexanol | | | 3.88[e] | 486 |
| 23 | trans-4-{6-[4-(Azepane-1-Sulfonyl)-phenylamino]-9-ethyl-9H-purin-2-yl-amino}-cyclohexanol | | | 4.60[e] | 514 |
| 24 | 4-[9-Ethyl-2-(trans-4-hydroxy-cyclohexyl-amino)-9H-purin-6-yl-amino]-phenyl-N-(4 methoxy-phenyl)-N-methyl-sulfonamide | | | 4.61[e] | 552 |
| 25 | 4-[9-Ethyl-2-(trans-4-hydroxy-cyclohexyl-amino)-9H-purin-6-yl-amino]-phenyl-N-(2-pyridin-2-yl-ethyl)-sulfonamide | | | 5.21[f] | 537 |
| 26 | trans-4-{6-[4-(4-Benzyl-piperazine-1-sulfonyl)-phenylamino]-9-ethyl-9H-purin-2-yl-amino}-cyclohexanol | | | 6.54[f] | 591 |
| 27 | 4-[9-Ethyl-2-(trans-4-hydroxy-cyclohexyl-amino)-9H-purin-6-yl-amino]-phenyl-N-(trans-4-hydroxy-cyclohexyl)-sulfonamide | | | 5.71[f] | 530 |
| 28 | 4-[9-Ethyl-2-(trans-4-hydroxy-cyclohexyl-amino)-9H-purin-6-yl-amino]-phenyl-N-naphthalen-1-yl-methyl-sulfonamide | | | 9.05[f] | 572 |
| 29 | 4-[9-Ethyl-2-(trans-4-hydroxy-cyclohexyl-amino)-9H-purin-6-yl-amino]-phenyl-N-heptyl-N-methyl-sulfonamide | | | 10.97[f] | 544 |
| 30 | N-(3,3-Diphenyl-propyl)-4-[9-ethyl-2-(trans-4-hydroxy-cyclohexylamino)-9H-purin-6-yl-amino]-phenyl-sulfonamide | | | 9.87[f] | 626 |
| 31 | 4-[9-Ethyl-2-(trans-4-hydroxy-cyclohexyl-amino)-9H-purin-6-yl-amino]-phenyl-N-(1-methyl-3-phenyl-propyl)-sulfonamide | | | 9.06[f] | 564 |
| 32 | 4-[9-Ethyl-2-(trans-4-hydroxy-cyclohexyl-amino)-9H-purin-6-yl-amino]-phenyl-N-(3-methyl-butyl)-sulfonamide | 200.0: 202.0 | 4.66 | | 502.2 |
| 33 | trans-4-{9-Ethyl-6-[4-(piperidine-1-sulfonyl)-phenylamino]-9H-purin-2-yl-amino}-cyclohexanol | 222.0: 223.0 | 4.35 | 8.27[f] | 500 |
| 34 | N-(3-Chloro-benzyl)-4-[9-ethyl-2(trans-4-hydroxy-cyclohexylamino)-9H-purin-6-yl-amino]-phenyl-sulfonamide | | | 8.60[f] | 556 |
| 35 | 4-[9-Ethyl-2-(trans-4-hydroxy-cyclohexyl-amino)-9H-purin-6-yl-amino]-phenyl-N-(3-imidazol-1-yl-phenyl)-sulfonamide | | | 5.80[f] | 574 |
| 36 | N-(3,4-Dimethoxy-phenyl)-4-[9-ethyl-2-(trans-4-hydroxy-cyclohexylamino)-9H-purin-6-yl-amino]-phenyl-sulfonamide | | | 7.22[f] | 568 |
| 37 | 4-[9-Ethyl-2-(trans-4-hydroxy-cyclohexyl-amino)-9H-purin-6-yl-amino]-phenyl-N-(5-fluoro-2-methyl-phenyl)-sulfonamide | | | 8.42[f] | 540 |
| 38 | N-(3,5-Dimethoxy-phenyl)-4-[9-ethyl-2-(trans-4-hydroxy-cyclohexylamino)-phenyl-9H-purin-6-yl-amino]-phenyl-sulfonamide | | | 8.03[f] | 568 |
| 39 | 4-9-Ethyl-2-(trans-4-hydroxy-cyclohexyl-amino)-9H-purin-6-yl-amino]-phenyl-N-methyl-N-phenyl-sulfonamide | 194.0: 195.0 | | 8.69[f] | 522 |
| 40 | 4-[9-Ethyl-2-(trans-4-hydroxy-cyclohexyl-amino)-9H-purin-6-yl-amino]-phenyl-N-(5,6,7,8-tetrahydro-1-naphthyl)-sulfonamide | | | 5.29[e] | 562 |
| 41 | N-Benzyl-4-[9-ethyl-2-(trans-4-hydroxy-cyclohexylamino)-9H-purin-6-yl-amino]-phenyl-N-phenyl-sulfonamide | | | 5.74[e] | 598 |
| 42 | 4-{4-(9-Ethyl-2-(trans-4-hydroxy-cyclohexylamino)-9H-purin-6-yl-amino]-phenyl-sulfonylamino}-benzoic acid propyl ester | | | 8.30[f] | 594 |

-continued

| Ex Nr. | compound | m.p. [° C.] | R$_f$ | HPLC t$_{Ret}$ (min) | APCI [M + 1]$^+$ |
|---|---|---|---|---|---|
| 43 | 4-[9-Ethyl-2-(trans-4-hydroxy-cyclohexyl-amino)-9H-purin-6-yl-amino]-phenyl-N-(4-morpholin-4-yl-phenyl)-sulfonamide | | | 6.55$^{f)}$ | 593 |
| 44 | 4-[9-Ethyl-2-(trans-4-hydroxy-cyclohexyl-amino)-9H-purin-6-yl-amino]-phenyl-N-quinolin-3-yl-sulfonamide | | | 6.94$^{f)}$ | 559 |
| 45 | 4-[9-Ethyl-2-(trans-4-hydroxy-cyclohexyl-amino)-9H-purin-6-yl-amino]-phenyl-N-(4-phenoxy-phenyl)-sulfonamide | | | 5.48$^{e)}$ | 600 |
| 46 | N-(2,4-Dimethyl-phenyl)-4-[9-ethyl-2-(trans-4-hydroxy-cyclohexylamino)-9H-purin-6-yl-amino]-phenyl-sulfonamide | | | 8.62$^{f)}$ | 536 |
| 47 | 4-[9-Ethyl-2-(trans-4-hydroxy-cyclohexyl-amino)-9H-purin-6-yl-amino]-phenyl-N-m-tolyl-sulfonamide | | | 8.23$^{f)}$ | 522 |
| 48 | 4-[9-Ethyl-2-(trans-4-hydroxy-cyclohexyl-amino)-9H-purin-6-yl-amino]-phenyl-N-o-tolyl-sulfonamide | | | 8.13$^{f)}$ | 522 |
| 49 | 4-[9-Ethyl-2-(trans-4-hydroxy-cyclohexyl-amino)-9H-purin-6-yl-amino]-phenyl-N-(3-trifluoromethyl-phenyl)-sulfonamide | | | 8.96$^{f)}$ | 576 |
| 50 | N-(3,4-Dichloro-phenyl)-4-[9-ethyl-2-(trans-4-hydroxy-cyclohexylamino)-9H-purin-6-yl-amino]-phenyl-sulfonamide | | | 5.41$^{e)}$ | 576 |
| 51 | N-(3-Chloro-phenyl)-4-[9-ethyl-2-(trans-4-hydroxy-cyclohexylamino)-9H-purin-6-yl-amino]-phenyl-sulfonamide | | | 4.95$^{e)}$ | 542 |
| 52 | 4-[9-Ethyl-2-(trans-4-hydroxy-cyclohexyl-amino)-9H-purin-6-yl-amino]-phenyl-N-phenyl-sulfonamide | | | 4.47$^{e)}$ | 508 |
| 53 | 4-[9-Ethyl-2-(trans-4-hydroxy-cyclohexyl-amino)-9H-purin-6-yl-amino]-phenyl-N-propyl-sulfonamide | | | 7.15$^{f)}$ | 474 |
| 54 | N-Butyl-4-[9-ethyl-2-(trans-4-hydroxy-cyclohexyl-amino)-9H-purin-6-yl-amino]-phenyl-N-methyl-sulfonamide | 234.0: 237.0 | | 8.89$^{e)}$ | 502 |
| 55 | trans-4-{9-Ethyl-6-[4-(4-phenyl-piperazine-1-sulfonyl)-phenylamino]-9H-purin-2-yl-amino}-cyclohexanol | 255.0: 256.0 | | 4.98$^{e)}$ | 577.2 |
| 56 | 4-[9-Ethyl-2-(trans-4-hydroxy-cyclohexyl-amino)-9H-purin-6-yl-amino]-phenyl-N-3-pyridylmethyl-sulfonamide | | | 5.13$^{f)}$ | 523 |
| 57 | 4-[9-Ethyl-2-(trans-4-hydroxy-cyclohexyl-amino)-9H-purin-6-yl-amino]-phenyl-N-2-furanylmethyl-sulfonamide | | | 7.24$^{f)}$ | 512 |
| 58 | N-Benzyl-N-ethyl-4-[9-ethyl-2-(trans-4-hydroxy-cyclohexylamino)-9H-purin-6-yl-amino]-phenyl-suifonamide | | | 9.42$^{f)}$ | 550 |
| 59 | N-Cyclohexyl-4-[9-ethyl-2-(trans-4-hydroxy-cyclohexylamino)-9H-purin-6-yl-amino]-phenyl-sulfonamide | 250.0: 251.0 | | 4.67$^{e)}$ | 514.2 |
| 60 | N-Cyclopropyl-4-[9-ethyl-2-(trans-4-hydroxy-cyclohexylamino)-9H-purin-6-yl-amino]-phenyl-sulfonamide | | | 6.72$^{f)}$ | 472 |
| 61 | 4-[9-Ethyl-2-(trans-4-hydroxy-cyclohexyl-amino)-9H-purin-6-yl-amino]-phenyl-N-(3-hydroxy-propyl)-sulfonamide | | | 5.43$^{f)}$ | 490 |
| 62 | 4-[9-Ethyl-2-(trans-4-hydroxy-cyclohexyl-amino)-9H-purin-6-yl-amino]-phenyl-N-isobutyl-sulfonamide | 200.0: 201.0 | | 4.39$^{e)}$ | 488.2 |
| 63 | N,N-Dibutyl-4-[9-ethyl-2-(trans-4-hydroxy-cyclohexylamino)-9H-purin-6-yl-amino]-phenyl-sulfonamide | | | 10.53$^{f)}$ | 544 |
| 64 | 4-[9-Ethyl-2-(trans-4-hydroxy-cyclohexyl-amino)-9H-purin-6-yl-amino]-phenyl-N-octyl-sulfonamide | | | 10.44$^{f)}$ | 544 |
| 65 | trans-4-{9-Ethyl-6-[4-(morpholine-4-sulfonyl)-phenyl-amino]-9H-purin-2-yl-amino}-cyclohexanol | 205: 207 | | 5.42$^{g)}$ | 502 |
| 66 | trans-4-{9-Ethyl-6-[4-(4-methyl-piperazine-1-sulfonyl)-phenyl-amino]-9H-purin-2-yl-amino}-cyclohexanol | 177: 180 | | 4.78$^{g)}$ | 515 |
| 67 | N-Butyl-4-[9-ethyl-2-(trans-4-hydroxy-cyclohexyl-amino)-9H-purin-6-yl-amino]-phenyl-sulfonamide | 190: 191 | | 4.42$^{e)}$ | 488 |

-continued

| Ex Nr. | compound | m.p. [° C.] | $R_f$ | HPLC $t_{Ret}$ (min) | APCI $[M + 1]^+$ |
|---|---|---|---|---|---|
| 68 | 4-[9-Ethyl-2-(trans-4-hydroxy-cyclohexyl-amino)-9H-purin-6-yl-amino]-phenyl-N-isopropyl-sulfonamide | 224: 226 | | 5.52[g)] | 474 |
| 69 | N-Benzyl-4-[9-ethyl-2-(trans-4-hydroxy-cyclohexyl-amino)-9H-purin-6-yl-amino]-phenyl-sulfonamide | 191: 193 | | 6.11[g)] | 522 |
| 70 | 4-[9-Ethyl-2-(trans-4-hydroxy-cyclohexyl-amino)-9H-purin-6-yl-amino]-phenyl-N-methyl-sulfonamide | 233: 235 | | 4.96[g)] | 446 |
| 71 | 4-[9-Ethyl-2-(trans-4-hydroxy-cyc)ohexyl-amino)-9H-purin-6-yl-amino]-phenyl-N,N-dimethyl-sulfonamide | 264: 266 | | 5.41[g)] | 460 |

Legend:

a) Eluent: ($CH_2Cl_2$/MeOH (9/1)+1% $NH_3$)
b) Eluent: ($CH_2Cl_2$/MeOH (95/5)+1% $NH_3$)
c) Eluent: ($CH_2Cl_2$/MeOH (9/1)
d) HPLC-System: Kontron 322 System, pressure: 130 bars (T=0 min), flow: 1 ml/min
  Eluents: B: acetonitrile (+0.1% trifluoroacetic acid)
    A: water (+0.1% trifluoroacetic acid)
  Gradient: 20–100% acetonitrile in 13 min+5 min 100% acetonitrile
e) HPLC-system: HP 1100, column: Nucleosil 100-3 C18HD (length 12.5 cm/diameter 4.6 mm), flow 1 ml/min., detection at 215 nm, oven temp. 30° C.
  gradient: acetonitrile-water (incl. 0.1% trifluoroacetic acid in both)
    20→100% acetonitrile in 7 min.+3 min. 100% acetonitrile
f) HPLC-system: HP 1100, column: Nucleosil 100-5 C18 (length 25 cm/diameter 4.6 mm), flow 1 ml/min., detection at 215 nm, oven temp. 30° C.
  gradient: acetonitrile-water (incl. 0.1% trifluoroacetic acid in both)
    20→100% acetonitrile in 13 min.+5 min. 100% acetonitrile
g) HPLC-system: Spectra Physics, column: Nucleosil 100-5 C18, detection at 214 nm, oven temp. RT
  gradient: acetonitrile-water (incl. 0.1% trifluoroacetic acid in both)
    2→100% acetonitrile in 13 min.+5 min. 100% acetonitrile

EXAMPLE 72

A 250 ml flask is charged with 5.4 g (13.6 mmol) of 3-[9-ethyl-2-(trans-4-hydroxy-cyclohexyl-amino)-9H-purin-6-yl-amino]-benzoic acid, 110 ml of DMF, 5.26 g (27.4 mmol) EDC, 3.71 g (27.4 mmol) HOBT and 9.54 ml (68.4 mmol) of triethylamine. After 40 min stirring at RT, 2.22 ml (20.34 mmol) of benzylamine is added, and the suspension is stirred for another 22 h at RT. After completion, the reaction mixture is distributed between water (800 ml) and ethyl acetate (300 ml). The aqueous layer is extracted with ethyl acetate (2 fold). The combined organic layers are washed with water, sat. $NaHCO_3$ soln. and brine, dried over $MgSO_4$, filtered and concentrated. After purification by chromatography (silica gel, $CH_2Cl_2$/MeOH: 95/5) the desired product N-benzyl-3-[9-ethyl-2-(trans-4-hydroxy-cyclohexylamino)-9H-purin-6-yl-amino]-benzamide is obtained (6.0 g; 91% yield) as a crystalline powder. $R_f$=0.43; ($CH_2Cl_2$/MeOH (9/1)); m.p. 215° C.; ESI-MS: 486.2 (M+H)$^+$.

Stage 1.1:

To a solution of 2,6-dichloropurine (17 g, 90 mmol) in 300 ml of 1-pentanol are added 37.8 g (250 mmol) of methyl-3-aminobenzoate and stirred for 8 hours at 75° C. After cooling to RT, 200 ml of isopropanol is added and the mixture is stirred for 1 h. After filtration, the precipitate is taken up into MeOH/$H_2O$ and treated with $NaHCO_3$ to pH >8. After filtration, the product ist washed with $H_2O$ and MeOH and dried to obtain 25.4 g (93% yield) of 3-(2-chloro-9H-purin-6-yl-amino)-benzoic acid methyl ester, $R_f$=0.5; ($CH_2Cl_2$/MeOH (9/1)); m.p. 242° C.; ESI-MS: 304 (M+H)$^+$.

Stage 1.2:

A 750 ml flask is charged with 25.4 g (83.5 mmol) of 3-(2-chloro-9H-purin-6-yl-amino)-benzoic acid methyl ester, 12.95 g (93.7 mmol) of $K_2CO_3$ and 360 ml of DMF. The mixture is stirred at RT for 30 min, then 35.8 ml (443 mmol) ethyliodide are added under slight cooling. After completion, the mixture is poured into water/EtOAc (1.2 l each). The aqueous layer is extracted with ethyl acetate (2 fold). The combined organic layers are washed with water and brine, dried ($Na_2SO_4$), filtered and concentrated. After purification by chromatography (silica gel, EtOAc) the desired product, 3-(2-chloro-9-ethyl-9H-purin-6-yl-amino) benzoic acid methyl ester, (19.1 g, 69% yield) is obtained; $R_f$=0.25; (EtOAc); m.p. 148° C.; ESI-MS: 332 (M+H)$^+$.

Stage 1.3:

18.9 g (57 mmol) of 3-(2-chloro-9-ethyl-9H-purin-6-yl-amino)-benzoic acid methyl ester and 32.8 g (280 mmol) of of trans-4-hydroxy-cyclohexylamine are suspended in 200 ml of diglyme and kept at 155° C. under magnetic stirring for 44 h. After cooling to RT, the mixture is poured into water/EtOAc (0.5/1.5 l each). The aqueous layer is extracted with ethyl acetate. The combined organic layers are washed with water and brine, dried ($Na_2SO_4$), filtered and concentrated. After purification by chromatography (silica gel, $CH_2Cl_2$/MeOH: 9/1) the desired product 3-[9-ethyl-2-(trans-4-hydroxy-cyclohexylamino)-9H-purin-6-yl-amino]-benzoic acid methyl ester is obtained; $R_f$=0.44; ($CH_2Cl_2$/MeOH: 9/1); m.p. 184° C.; ESI-MS: 411 (M+H)$^+$.

Stage 1.4:

15.8 g (38.5 mmol) of 3-[9-ethyl-2-(trans-4-hydroxy-cyclohexylamino)-9H-purin-6-yl-amino]-benzoic acid methyl ester is suspended in 400 ml of MeOH, 77 ml of $H_2O$ and 77 ml of LiOH solution (1M), and stirred for 75 min at 80° C. After completion, the MeOH is removed under reduced pressure and the aqueous layer is washed with EtOAc (2 fold). The aqueous layer is then slowly treated with 1N HCl solution to pH 4–4.5. The precipitate is filtered off and washed to neutral pH to obtain 13.2 g (87% yield) of 3-[9-ethyl-2-(trans-4-hydroxy-cyclohexylamino)-9H-purin-6-yl-amino]-benzoic acid; $R_f$=0.34; (CH$_3$Cl/MeOH/H$_2$O/CH$_3$COOH 85/13/1.5/0.5); m.p. 317° C.; ESI-MS: 397 (M+H)$^+$.

EXAMPLE 73

Analogously to example 72, 3-[9-ethyl-2-(trans-4-hydroxy-cyclohexylamino)-9H-purin-6-yl-amino]-N-(4-fluoro-benzyl)-benzamide is obtained as white crystals (69% yield) from 250 mg (0.63 mmol) of 3-[9-ethyl-2-(trans-4-hydroxy-cyclohexylamino)-9H-purin-6-yl-amino]-benzoic acid, 5 ml of DMF, 145 mg (0.75 mmol) EDC, 115 mg (0.75 mmol) HOBT and 87 mg (0.69 mmol) of 4-fluorobenzylamine at RT, followed by purification by chromatography; m.p. 165–167° C.; ESI-MS: 504.2 (M+H)$^+$; $t_{Ret}$ (HPLC) 4.31 min (method e).

EXAMPLE 74

Analogously to example 72, 3-[9-ethyl-2-(trans-4-hydroxy-cyclohexylamino)-9H-purin-6-yl-amino]-N-(4-methyl-benzyl)-benzamide is obtained as white crystals (70% yield) from 250 mg (0.63 mmol) of 3-[9-ethyl-2-(trans-4-hydroxy-cyclohexylamino)-9H-purin-6-yl-amino]-benzoic acid, 5 ml of DMF, 145 mg (0.75 mmol) EDC, 115 mg (0.75 mmol) HOBT and 84 mg (0.69 mmol) of 4-methylbenzylamine at RT, followed by purification by chromatography; m.p. 130–134° C.; ESI-MS: 500.3 (M+H)$^+$; $t_{Ret}$ (HPLC) 4.50 min (method e).

EXAMPLE 75

Analogously to example 72, 3-[9-ethyl-2-(trans-4-hydroxy-cyclohexylamino)-9H-purin-6-yl-amino]-N-(4-methoxy-benzyl)-benzamide is obtained as white crystals (43% yield) from 250 mg (0.63 mmol) of 3-[9-ethyl-2-(trans-4-hydroxy-cyclohexylamino)-9H-purin-6-yl-amino]-benzoic acid, 5 ml of DMF, 145 mg (0.75 mmol) EDC, 115 mg (0.75 mmol) HOBT and 95 mg (0.69 mmol) of 4-methoxybenzylamine at RT, followed by purification by chromatography; m.p. 157–158° C.; ESI-MS: 516.2 (M+H)$^+$; $t_{Ret}$ (HPLC) 4.18 min (method e).

EXAMPLE 76

Analogously to example 72, 3-[9-ethyl-2-(trans-4-hydroxy-cyclohexylamino)-9H-purin-6-yl-amino]-N-(4-trifluoromethyl-benzyl)-benzamide is obtained as white crystals (64% yield) from 250 mg (0.63 mmol) of 3-[9-ethyl-2-(trans 4-hydroxy-cyclohexylamino)-9H-purin-6-yl-amino]-benzoic acid, 5 ml of DMF, 145 mg (0.75 mmol) EDC, 115 mg (0.75 mmol) HOBT and 95 mg (0.69 mmol) of 4-trifluoromethylbenzylamine at RT, followed by purification by chromatography; m.p. 129–137° C.; ESI-MS: 554.2 (M+H)$^+$; $t_{Ret}$ (HPLC) 4.88 min (method e).

EXAMPLE 77 trans-4-[6-(4-amino-phenylamino)-9-ethyl-9H-purin-2-yl-amino]-cyclohexanol (100 mg, 0.272 mmol) is suspended in 1 ml dichloromethane and treated with 22 µl (0.272 mmol) methanesulfonyl chloride. The reaction mixture is stirred at RT for 48 h. The crude product is recovered by filtration and purified by chromatography on silica gel (CH$_2$Cl$_2$/MeOH 95:5). N-{4-[9-ethyl-2-(trans-4-hydroxy-cyclohexylamino)-9H-purin-6-yl-amino]-phenyl}-methane-sulfonamide is obtained as an amorphous material, 43 mg (36%); MS [M+H]$^+$444; HPLC (System h) $t_R$=4.63 min.

Stage 1.1:
Analogously to example 72, stage 1.3, trans-4-[9-ethyl-6-(4-nitro-phenylamino)-9H-purin-2yl-amino]-cyclohexanol (35% yield) is obtained from (2-chloro-9-ethyl-9H purin-6-yl)-(4-nitro-phenyl-amine; ESI-MS: 398 (M+H)$^+$; $t_{Ret}$ (HPLC) 7.77 min (method f).

Stage 1.2 :
A flask is charged with 12.15 g (30.57 mmol) of trans-4-[9-ethyl-6-(4-nitro-phenylamino)-9H-purin-2-yl-amino]-cyclohexanol in 1.15 l of methanol and kept under argon. At 40° C. Raney-Nickel is added slowly, followed by dropwise addition of 15.04 ml (50.06 mmol) of hydrazine monohydrate. After completion the reaction mixture is filtered, the filtrate concentrated and the crude product is purified by chromatography to obtain trans-4-[6-(4-amino-phenyl-amino)-9-ethyl-9H-purin-2-yl-amino]-cyclohexanol (74% yield); ESI-MS: 368 (M+H)$^+$; $t_{Ret}$ (HPLC) 7.48 min (method: same system as in method d, gradient 5®40% acetonitrile in 7,5 min.+12 min. 40% acetonitrile).

EXAMPLES 78 AND 79

Examples 78 and 79 are synthesized analogously to example 77.

EXAMPLE 80

Analogously to example 77 but starting from trans-4-[6-(3-amino-phenylamino)-9-ethyl-9H-purin-2-yl-amino] cyclohexanol N-{3-[9-ethyl-2-(trans-4-hydroxy-cyclohexylamino)-9H-purin-6-yl-amino]-phenyl}-methane-sulfonamide is obtained; m.p. 265–267° C.; MS (M+H)$^+$ 446; HPLC (System h) $t_R$=4.66 min.

Stage 1.1:
Analogously to example 72, stage 1.3, trans-4-[9-ethyl-6-(3-nitro-phenylamino)-9H-purin-2yl-amino]-cyclohexanol (35% yield) is obtained from (2-chloro-9-ethyl-9H-purin-6-yl)-(3-nitro-phenyl)-amine); m.p. 237–238° C.; $R_f$=0.29; (CH$_2$Cl$_2$/MeOH 95/5); ESI-MS: 398 (M+H)$^+$.

Stage 1.2 :
A flask is charged with 795 mg (2 mmol) of trans-4-[9-ethyl-6-(3-nitro-phenylamino)-9H-purin-2-yl-amino]-cyclohexanol in 75 ml of methanol and kept under argon. At 40° C. 40 mg of Raney-Nickel is added slowly, followed by addition of 1 ml (31 mmol) of hydrazine monohydrate. After completion the reaction mixture is filtered, the filtrate concentrated and the crude product is taken up into EtOAc (300 ml), extracted with water, dried and evaporated to obtain trans-4-[6-(3-amino-phenylamino)-9-ethyl-9H-purin-2-yl-amino]-cyclohexanol (94% yield); m.p. 149–151° C.; ESI-MS: 368 (M+H)$^+$.

EXAMPLES 81 AND 82

Examples 81 and 82 are synthesized analogously to example 80.

EXAMPLE 83 trans 4-[6-(4-amino-phenylamino)-9-ethyl-9H-purin-2-yl-amino]-cyclohexanol (example 77, stage 1.2, 100 mg, 0.272 mmol) is suspended in 1 ml dichloromethane and treated with 21 µl (0.272 mmol) methyl chloroformate. The reaction mixture is stirred at RT for 20 h after which another equivalent of methyl chloroformate (21 µl, 0.272 mmol) is added. After additional 23 h at RT the reaction mixture is evaporated and the product purified by chromatography on silica gel (CH$_2$Cl$_2$/MeOH 95:5). {4-[9-ethyl-2-(trans-4- hydroxy-cyclo-hexylamino)-9H-purin-6-yl-amino]-phenyl}-carbamic acid methyl ester is obtained as tan crystals, 93 mg (81%). m.p. 131–135° C.; MS [M+H]⁺426; HPLC (System h) t$_R$=4.84 min.

EXAMPLES 84 TO 91

Analogously to example 83 are synthesized examples 84 and 85. Analogously to example 83 but starting from trans-4-[6-(3-amino-phenylamino)-9-ethyl-9H-purin-2-yl-amino]-cyclohexanol (example 80, stage 1.2) are obtained examples 86 to 91.

EXAMPLE 92

To the solution of 190 mg (1 mmol) of (4-chlorophenyl)-propargylic acid in 20 ml of DMF at 0° C. is added 165 mg (1.1 mmol) of HOBT and 210 mg (1.1 mmol) of EDC. After 3 h at 0° C., 367 mg (1 mmol) of 4-[6-(3-Amino-phenylamino)-9-ethyl-9H-purin-2-ylamino]-cyclohexanol (example 77, stage 1.2) is added. After 1 h at 0° C. and 2.5 h at RT, the solvent was removed under reduced pressure. The crude product is purified by means of column chromatography on silica gel, trituration in diethyl ether and recrystallisation from ethanol to obtain 110 mg (0.21 mmol) of N-{3-[9-Ethyl-2-(trans-4-hydroxy-cyclohexylamino)-9H-purin-6yl-amino]-phenyl}-3-(4-chlorophenyl)-propargylic acid amide.

EXAMPLES 93 TO 106

Analogously to example 92 are synthesized examples 93 to 95.

| Example | Name | M.P. | Rf | HPLC* | MS, ES+ |
|---|---|---|---|---|---|
| 77 | N-{4-[9-Ethyl-2-(trans-4-hydroxy-cyclo-hexylamino)-9H-purin-6-yl-amino]-phenyl}-methanesulfonamide | — | — | 4.63 | 444 |
| 78 | N-{4-[9-Ethyl-2-(trans-4-hydroxy-cyclo-hexylamino)-9H-purin-6-yl-amino]-phenyl}-4-methyl-benzenesulfonamide | — | — | 6.01 | 520 |
| 79 | N-{4-[9-Ethyl-2-(trans-4-hydroxy-cyclo-hexylamino)-9H-purin-6-yl-amino]-phenyl}-4-methoxy-benzenesulfonamide | — | — | 9.65 | 538 |
| 80 | N-{3-[9-Ethyl-2-(trans-4-hydroxy-cyclo-hexylamino)-9H-purin-6-yl-amino]-phenyl} methanesulfonamide | 265–267 | — | 4.66 | 446 |
| 81 | N-{3-[9-Ethyl-2-trans-4-hydroxy-cyclo-hexylamino)-9H-purin-6-yl-amino]-phenyl)-4-methyl-benzenesulfonamide | 142–145 | — | 6.08 | 522 |
| 82 | N-{3-[9-Ethyl-2-(trans-4-hydroxy-cyclo-hexylamino)-9H-purin-6-yl-amino]-phenyl}-4-methoxy-benzenesulfonamide | 140–143 | — | 5.75 | 538 |
| 83 | {4-(9-Ethyl-2-(trans-4-hydroxy-cyclo-hexylamino)-9H-purin-6-yl-amino]-phenyl)-carbamic acid methyl ester | 131–135 | — | 4.84 | 426 |
| 84 | {4-[9-Ethyl-2-(trans-4-hydroxy-cyclo-hexylamino)-9H-purin-6-yl-amino]-phenyl}-carbamic acid isobutyl ester | 121–125 | — | 6.54 | 468 |
| 85 | {4-[9-Ethyl-2-(trans-4-hydroxy-cyclo-hexylamino)-9H-purin-6-yl-amino]-phenyl}-carbamic acid phenyl ester | 135–139 | — | 6.34 | 488 |
| 86 | {3-[9-Ethyl-2-(trans-4-hydroxy-cyclo-hexylamino)-9H-purin-6-yl-amino]-phenyl}-carbamic acid methyl ester | 214–217 | — | 4.88 | 426 |
| 87 | {3-[9-Ethyl-2-(trans-4-hydroxy-cyclo-hexylamino)-9H-purin-6-yl-amino]-phenyl}-carbamic acid isobutyl ester | 122–125 | — | 6.41 | 468 |
| 88 | {3-[9-Ethyl-2-(trans-4-hydroxy-cyclo-hexylamino)-9H-purin-6-yl-amino]-phenyl}-carbamic acid phenyl ester | 131–134 | — | 6.43 | 488 |
| 89 | N-{3-[9-Ethyl-2-(trans-4-hydroxy-cyclo-hexylamino)-9H-purin-6-yl-amino]-phenyl}-3-trimethylsilylpropargylic acid amide | | | | 492.4 |
| 90 | N-{3-[9-Ethyl-2-(trans-4-hydroxy-cyclo-hexylamino)-9H-purin-6-yl-amino]-phenyl}-3-phenylpropargylic acid amide | | | 6.62[e] | 496.3 |
| 91 | N-{3-[9-Ethyl-2-(trans-4-hydroxy-cyclo-hexylamino)-9H-purin-6-yl-amino]-phenyl}-4,4-dimethyl-2-pentynylic acid amide | 199 | 0.36[c] | 9.54[e] | 476.2 |
| 92 | N-{3-[9-Ethyl-2-(trans-4-hydroxy-cyclo-hexylamino)-9H-purin-6-yl-amino]-phenyl}-3-(4-chlorophenyl)-propargylic acid amide | 148–150 | 0.23[b] | 5.09[e] | 529.9 |
| 93 | N-{3-[9-Ethyl-2-(trans-4-hydroxy-cyclo-hexylamino)-9H-purin-6-yl-amino]-phenyl}-3-(4-fluorophenyl)-propargylic acid amide | 144–146 | 0.18[b] | 4.74[e] | 513.9 |

-continued

| Example | Name | M.P. | Rf | HPLC* | MS, ES+ |
|---------|------|------|-----|-------|---------|
| 94 | N-{3-[9-Ethyl-2-(trans-4-hydroxy-cyclo-hexylamino)-9H-purin-6-yl-amino]-phenyl}-3-p-tolylpropargylic acid amide | 146–148 | 0.24[b] | 5.00[e] | 510 |
| 95 | N-{3-[9-Ethyl-2-(trans-4-hydroxy-cyclo-hexylamino)-9H-purin-6-yl-amino]-phenyl}-3-(4-methoxyphenyl)-propargylic acid amide | 142–144 | 0.22 | 4.68 | 525.9 |

*HPLC system h

HPLC system h):

| | | |
|---|---|---|
| Column: | Nucleosil C18 | length: 12,5 cm/diameter. 4,0 mm |
| Flow rate: | 1 ml/min. | |
| Detection: | 215 nm | |
| Oven temperature: | 30° C. | |

1997, H. G. Korth et al). 4-[6-(3-Amino-phenylamino)-9-isopropyl-9H-purin-2-ylamino]-cyclohexanol is prepared analogously to example 77 (stage 1.2), but starting from trans-4-[9-ethyl-6-(3-nitro-phenylamino)-9H-purin-2-ylamino]cyclohexanol. Trans-4-[9-ethyl-6-(3-nitro-phenylamino)-9H-purin-2-ylamino]-cyclohexanol is prepared analogously to example 72 (stage 1.1–stage 1.3), but starting from 2,6-dichloropurine and 3-nitrophenylaniline.

| Ex Nr. | Name | m.p. [° C.] | Rf | HPLC $t_{Ret}$ (min) | APCI $[M + 1]^+$ |
|--------|------|-------------|-----|---------------------|------------------|
| 96 | 3-(4-Chloro-phenyl)-propynoic acid {3-[2-(4-hydroxy-cyclohexylamino)-9-isopropyl-9H-purin-6-ylamino]-phenyl}-amide | 156–158 | 0.32[b] | 5.28 | 543.9[e] |
| 97 | 3-p-Tolyl-propynoic acid {3-[2-(4-hydroxy-cyclohexylamino)-9-isopropyl-9H-purin-6-ylamino]-phenyl}-amide | 152–154 | 0.32[b] | 5.14 | 524.0[e] |
| 98 | 3-(4-Methoxy-phenyl)-propynoic acid {3-[2-(4-hydroxy-cyclohexyl-amino)-9-isopropyl-9H-purin-6-ylamino]-phenyl)-amide | 246–248 | 0.25[b] | 4.88 | 540.0[e] |
| 99 | 3-(4-Fluoro-phenyl)-propynoic acid {3-[2-(4-hydroxy-cyclohexylamino)-9-isopropyl-9H-purin-6-ylamino]-phenyl}-amide | 145–147 | 0.19[b] | 4.93 | 528.0[e] |
| 100 | 3-(Phenyl)-propynoic acid {3-[2-(4-hydroxy-cyclohexylamino)-9-isopropyl-9H-purin-6-ylamino]-phenyl}-amide | 162–164 | 0.24[b] | 4.86 | 509.9[e] |
| 101 | Biphenyl-4-carboxylic acid {3-[2-(4-hydroxy-cyclohexylamino)-9-isopropyl-9H-purin-6-ylamino]-phenyl]-amide | 226–228 | 0.24[b] | 5.41 | 562.0[e] |

-continued

HPLC system h):

| | |
|---|---|
| Gradient: | acetonitrile-water (containing 0,1% trifluoroacetic acid). 5 ® 40% acetonitrile in 3 min. + 6 min. 40% acetonitrile |

EXAMPLES 96–101

Analogously to example 92 but starting from 4-[6-(3-amino-phenylamino)-9-isopropyl-9H-purin-2-ylamino]-cyclohexanol are synthesized examples 96 to 101. The respective propynoic acids are prepared from the corresponding commercially available alkynes, according to literature procedure (J. Chem. Soc. Perkin Trans 2, 1990, p.

EXAMPLES 102–106

Analogously to example 92 are synthesised examples 102–106. The respective propynoic acids are prepared from the corresponding commercially available alkynes, according to literature procedure (J. Chem. Soc. Perkin Trans 2, 1990, p.1997, H. G. Korth et al).

| Ex Nr. | Name | m.p. [° C.] | Rf | HPLC $t_{Ret}$ (min) | APCI $[M + 1]^+$ |
|---|---|---|---|---|---|
| 102 | 3-m-Tolyl-propynoic acid {3-[9-ethyl-2-(4-hydroxy-cyclohexylamino)-9H-purin-6-ylamino]-phenyl}-amide | 164–171 | 0.33<sup>a)</sup> | 4.96<sup>e)</sup> | 510.0 |
| 103 | 3-(3-Trifluoromethyl-phenyl)-propynoic acid {3-[9-ethyl-2-(4-hydroxy-cyclohexylamino)-9H-purin 6-ylamino]-phenyl}-amide | 156–168 | 0.28<sup>a)</sup> | 5.26<sup>e)</sup> | 563.8 |
| 104 | 4,4-Dimethyl-pent-2-ynoic acid {3-[(9-ethyl-2-(4-hydroxy-cyclohexylamino)-9H-purin-6-ylamino]-phenyl}-amide | 199.2 | 0.36<sup>c)</sup> | 9.54<sup>f)</sup> | 476.2 |
| 105 | 3-(6-Methyl-pyridin-2-yl)-propynoic acid {3-[9-ethyl-2-(4-hydroxy-cyclohexylamino)-9H-purin-6-ylamino]-phenyl}-amide | 149–156 | 0.32<sup>b)</sup> | 3.63<sup>e)</sup> | 511.3 |
| 106 | 3-(4-Methyl-pyrimidin-2-yl)-propynoic acid {3-[9-ethyl-2-(4-hydroxy-cyclohexylamino)-9H-purin-6-ylamino]-phenyl}-amide | 167–177 | 5.26<sup>b)</sup> | 5.26<sup>e)</sup> | 512.3 |

EXAMPLE 107

N-{3-[9-Ethyl-2-(trans-4-hydroxy-cyclohexylamino)-9H-purin-6-yl-amino]-phenyl}-3-(2,6-dichlorophenyl)-propargylic acid amide To a solution of 4.3 g (0.02 mol) (2,6-dichlorophenyl)-propargylic acid (M. S. Reich et al., *Bull. Soc. Chim. Fr.* 21, 217–225 (1917)) in 120 ml DMF and 120 ml acetonitrile are added at RT 4.23 ml (0.025 mol) N,N-di-isopropyl-N-ethylamine, followed by a solution of 5.94 g (0.02 mol) TPTU (O-(1,2-dihydro-2-oxo-1-pyridyl)-N,N,N',N'-tetramethyluronium tetrafluoroborate, Fluka, Buchs, Switzerland) in 100 ml DMF. The resulting solution is stirred at RT for 5 minutes and then added dropwise to a solution of 7.36 g (0.02 mol) 4-[6-(3-amino-phenylamino)-9-ethyl-9H-purin-2-ylamino]-cyclohexanol (example 77, stage 1.2) in a 1:1 mixture of DMF and acetonitrile (240 ml). The addition takes 1.25 hrs and stirring at RT is continued for an additional hour. A second portion of preactivated (2,6-dichlorophenyl)-propargylic acid [prepared by adding 2.0 g (0.0066 mol) TPTU in 30 ml DMF to a solution of 1.3 g (0.0066 mol) (2,6-dichlorophenyl)-propargylic acid in 30 ml DMF and 30 ml acetonitrile and stirring for 5 minutes at RT] was then added dropwise over 30 minutes. After stirring for another 1.5 hrs the solvent is evaporated under reduced pressure and the residue taken up in a mixture of ethyl acetate and 10% aqueous citric acid. The aqueous phase is extracted with ethyl acetate and the combined organic layers are washed with water, saturated sodium bicarbonate solution and brine. After drying (anhydrous sodium sulfate) the ethyl acetate solution is concentrated until the product crystallises. It is collected by filtration, re-suspended in a small amount of ethyl acetate, filtered and vacuum dried. N-{3-[9-Ethyl-2-(trans-4-hydroxy-cyclo-hexylamino)-9H-purin-6-yl-amino]-phenyl}-3-(2,6-dichlorophenyl)-propargylic acid amide (7.0 g, 60%), is obtained as a colourless solid.

EXAMPLES 108 TO 112

Analogously to example 107 are synthesized examples 108 to 112.

| Ex Nr. | Name | m.p. [° C.] | Rf | HPLC $t_{Ret}$ (min) | APCI $[M + 1]^+$ |
|---|---|---|---|---|---|
| 107 | N-{3-[9-Ethyl-2-(trans-4-hydroxy-cyclo-hexylamino-9H-purin-6-yl-amino]-phenyl}-3-(2,6-dichloro-phenyl)-propargylic acid amide | 234–236 | 0.35<sup>g)</sup> | 10.38<sup>h)</sup> | 564 |
| 108 | N-{3-[9-Ethyl-2-(trans-4-hydroxy-cyclo-hexylamino)-9H-purin-6-yl-amino]-phenyl}-3-(2-thiophenyl)-propargylic acid amide | 158–161 | 0.76<sup>g)</sup> | 9.3<sup>h)</sup> | 502 |
| 109 | N-{3-[9-Ethyl-2-(trans-4-hydroxy-cyclo-hexylamino)-9H-purin-6-yl-amino]-phenyl}-3-(2,5-dimethyl-phenyl)-propargylic acid amide | 231–232 | 0.32<sup>g)</sup> | 10.74<sup>h)</sup> | 524 |

-continued

| Ex Nr. | Name | m.p. [° C.] | Rf | HPLC $t_{Ret}$ (min) | APCI $[M + 1]^+$ |
|---|---|---|---|---|---|
| 110 | N-(3-[9-Ethyl-2-(trans-4-hydroxy-cyclo-hexylamino)-9H-purin-6-yl-amino]-phenyl}-3-(3,4-dimethyl-phenyl)-propargylic acid amide | 146–148 | 0.32[g] | 10.73[h] | 524 |
| 111 | 4-Piperidin-1-yl-but-2-ynoic acid {3-[9-ethyl-2-(4-hydroxy-cyclohexyl-amino)-9H-purin-6-ylamino]-phenyl}-amide | foam (dec. > 150° C.) | 0.10[i] | 6.75[h] | 517.3 |
| 112 | 4-(4-Methyl-piperazin-1-yl)-but-2-ynoic acid {3-[9-ethyl-2-(4-hydroxy-cyclohexylamino)-9H-purin-6-ylamino]-phenyl)-amide | 115–122 | 0.29[a] | 2.70[e] | 532.2 | g) Dichloromethane/ethanol 95:5 containing 1% conc. $NH_3$.
h) HPLC system:
Column: Nucleosil C18 length: 12.5 cm/diameter: 4.0 mm
Flow rate: 1 ml/min.
Detection: 215 nm
Oven temp.: 30° C.
Gradient: acetonitrile-water (containing 0.1% trifluoroacetic acid). 20→100% acetonitrile in 13 min. + 5 min. 100% acetonitrile
i) Ethyl acetate/methanol 9:1 containing 1% conc. $NH_3$.

EXAMPLE 113

Dry Capsules 5000 capsules, each of which contain 0.25 g of one of the compounds of the formula I mentioned in the preceding Examples as active ingredient, are prepared as follows:

| Composition | |
|---|---|
| Active ingredient | 1250 g |
| Talc | 180 g |
| Wheat starch | 120 g |
| Magnesium stearate | 80 g |
| Lactose | 20 g |

Preparation process: The powdered substances mentioned are pressed through a sieve of mesh width 0.6 mm. Portions of 0.33 g of the mixture are transferred to gelatin capsules with the aid of a capsule-filling machine.

What is claimed is:
1. A compound of the formula I

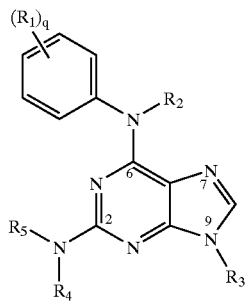

wherein q is 1–5,
$R_1$ is
α) —S(=O)$_k$—NR$_6$R$_7$, in which
k is 1 or 2,
wherein under the proviso that $R_6$ and $R_7$ cannot be simultaneously hydrogen
α1) $R_6$, $R_7$ can be identical or different from one another and represent an aliphatic, carbocyclic, heterocyclic, carbocyclic-aliphatic or heterocyclic-aliphatic radical; hydrogen or lower aliphatic acyl; or
α2) $R_5$ and $R_7$ together are an alkylene or alkenylene radical having from 3 up to and including 9 C atoms, in which 1–3 C atoms can be replaced by oxygen, sulfur or nitrogen, wherein said alkylene or alkenylene radical can be unsubstituted or substituted by halogen, hydroxy, lower alkoxy, amino, lower alkylamino, di-lower alkylamino, carbamoyl, lower alkylcarbamoyl or a radical —(CH$_2$)$_y$—R$_{10}$, in which y is 0 to 3, preferably 0 to 2, and R$_{10}$ is hydrogen or phenyl, which is unsubstituted or substituted by halogen, halogen lower alkyl, lower alkoxy, hydroxy, lower alkoxycarbonyl, amino, lower alkylamino, di-lower alkylamino, carbamoyl, lower alkylcarbamoyl, carboxyl, methylenedioxy or cyano, or
β) N-(aryl lower alkyl)carbamoyl, or
γ) a radical at the formula —NH—S(=O)$_i$—R$_8$, in which
i is 1 or 2,
R$_8$, an aliphatic, carbocyclic or heterocyclic radical; or
δ) a radical of the formula —NH—C(=O)—R$_9$, in which
R$_9$ is alkoxy, aryloxy, alkenyl, alkynyl, heterocyclyl alkynyl, aryl alkynyl, heteroaryl alkynyl, alkynyloxy or aryl alkynyloxy, which in each case is unsubstituted or substituted, the substituents being selected from the group consisting of halogen, hydroxy, phenyl, lower alkyl, lower alkoxy, lower alkoxycarbonyl, amino, lower alkylamino, di-lower alkylamino, carbamoyl, lower alkylcarbamoyl, carboxyl, methylenedioxy, tri-lower alkyl silyl, cyano or lower alkyl which is substituted by halogen, wherein such an unsubstituted or substituted R$_9$ radical has not more than 20 C atoms:

where, if more than one radical $R_1$ is present in the molecule, these can be identical or different from one another, $R_2$ is hydrogen, carbamoyl or N-lower alkyl-carbamoyl, $R_3$ is lower alkyl, which is unsubstituted or substituted by hydroxy, lower alkoxy, amino, lower alkylamino or N,N-di-lower alkylamino and a) $R_4$ is hydrogen, amino, phenylamino, lower alkylamino, hydroxyl, phenoxy, lower alkoxy, acyl having 1–30 C atoms, a carbocyclic or carbocyclic-aliphatic radical having not more than 29 C atoms, a heterocyclic or heterocyclic-aliphatic radical having not more than 20 C atoms and not more than 9 heteroatoms, or a substituted hydrocarbon radical having not more than 29 C atoms wherein the substituents are selected from halogen, amino, lower alkylamino, ω-amino-lower alkylamino, lower alkanoylamino, benzoylamino, hydroxylamino, hydroxylimino, lower alkoxy-amino, phenyloxyamino, amino-cyclohexyl-amino-, amino-phenyl-amino-, carbamoyl-amino, (N-lower alkyl-carbamoyl)-amino, (N-[ω-amino-lower alkyl]-carbamoyl)-amino, (N-phenyl-carbamoyl)-amino, lower alkylthio, thiocarbamoyl, thioureido, N-lower alkyl-thioureido, N-phenyl-thioureido, guanidino, N-lower alkyl-guanidino, carboxyl, lower alkoxycarbonyl, phenyloxycarbonyl, benzyloxycarbonyl, hydroxylaminocarbonyl, carbamoyl, amidino, cyano, lower alkoxy, phenyloxy, aminocarbonyl-oxy, oxo, aminosulfonyl, lower alkylsulfonyl-amino, glycylamino, alanylamino, phenylalanylamino, prolylamino, valylamino, leucylamino, isoleucylamino, serylamino, threonylamino, cysteinylamino, methionylamino, tyrosylamino, tryptophanylamino, arginylamino, histidylamino, lysylamino, glutamylamino, glutaminylamino, asparagylamino, asparaginylamino and phenylglycylamino; and $R_5$, independently of $R_4$, is as defined above for $R_4$, with the exception of hydrogen, or b) $R_4$ and $R_5$ together are 1,2-ethylene, propane-1,3-diyl, butane-1,4-diyl, pentane-1,5-diyl, 3-(3-amino-propionyl)-3-aza-pentane-1,5-diyl, 2-amino-butane-1,4-diyl, 1-aminomethyl-butane-1,4-diyl, 1-hydroxymethyl-butane-1,4-diyl, 3-hydroxy-pentane-1,5-diyl, 1-hydroxy-hexane-1,5-diyl, 3-(2-amino-ethyl)-pentane-1,5-diyl, 3-aza-pentane-1,5-diyl ($-CH_2-CH_2-NH-CH_2-CH_2-$), 3-aza-2,4-dimethyl-pentane-1,5-diyl ($-CH_2-CH[CH_3]-NH-CH[CH_3]-CH_2-$), 3-amino-3-aza-pentane-1,5-diyl ($-CH_2-CH_2-N[NH_2]-CH_2-CH_2-$), 1-aza-pentane-1,5-diyl, 1-aza-1-toluylaminocarbonyl-pentane-1,5-diyl, 1-aza-1-(methylamino-thiocarbonyl)-pentane-1,5-diyl, 1-aza-1-(tert-butylamino-carbonyl)-pentane-1,5-diyl, 1aza-1-(cyclohexylamino-carbonyl)-pentane-1,5-diyl, 3-aza-1-hydroxy-heptane-3,7-diyl, 3-aza-1-cyano-heptane-3,7-diyl, 1-amino-3-aza-heptane-3,7-diyl, 3-(2-amino-ethyl)-3-aza-pentane-1,5-diyl ($-CH_2-CH_2-N[-CH_2-CH_2-NH_2]-CH_2-CH_2-$), 1-carbamoyl-butane-1,4-diyl, 2-formylamino-pentane-1,4-diyl, 2-aza-butadiene-1,4-diyl ($-CH=CH-N=CH-$), 2-aza-3-hydroxymethyl-butadiene-1,4-diyl ($-CH=C[CH_2OH]-N=CH-$) or a radical of the formula

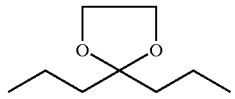

in which the two terminal bonds of the alkylene chain are free valencies, wherein in the above definitions an aliphatic radical is an unsubstituted or substituted alkyl, alkenyl or alkynyl radical having not more than 20 C atoms which alkenyl or alkynyl radicals are mono- or polyunsaturated and a substituted aliphatic radical carries one or more identical or different radicals selected from halogen, amino, lower alkylamino, di-lower alkylamino, ω-amino-lower alkylamino, lower alkanoylamino, aroylamino, hydroxylamino, hydroxylimino, lower alkoxy-amino, aryloxyamino, amino-cyclohexyl-amino-, amino-phenyl-amino-, carbamoyl-amino, (N-lower alkyl-carbamoyl)-amino, (N-[ω-amino-lower alkyl]-carbamoyl)-amino, (N-phenyl-carbamoyl)-amino, thio, lower alkylthio, thiocarbamoyl, thioureido, N-lower alkyl-thioureido, N-phenyl-thioureido, guanidino, N-lower alkyl-guanidino, carboxyl, lower alkoxycarbonyl, aryloxycarbonyl, benzyloxycarbonyl, hydroxylaminocarbonyl, aminoacyl-amino, carbamoyl, amidino, cyano, hydroxy, lower alkoxy, aryloxy, aminocarbonyl-oxy, oxo, aminosulfonyl and lower alkylsulfonyl-amino; or a salt thereof wherein hydrocarbon is either: 1) an acyclic, carbocyclic, or carbocyclic-acyclic radical having no more than 29 carbon atoms, or 2) an acyclic, carbocyclic, or carbocyclic-acyclic radical interrupted by one or more identical or different heteroatoms selected from oxygen, sulfur, and nitrogen having a total of no more than 29 C, O, S, and N atoms.

2. A compound of claim 1 formula I, wherein q is 1–5, $R_1$ is

α) $-S(=O)_k-NR_6R_7$, in which
  k is 1 or 2,
  wherein under the proviso that $R_6$ and $R_7$ cannot be simultaneously hydrogen
    α1) $R_8$, $R_7$ can be identical or different from one another and represent an aliphatic, carbocyclic, heterocyclic, carbocyclic-aliphatic or heterocyclic-aliphatic radical; hydrogen or lower aliphatic acyl; or
    α2) $R_6$ and $R_7$ together are an alkylene or alkenylene radical having from 3 up to and including 9 C atoms, in which 1–3 C atoms can be replaced by oxygen, sulfur or nitrogen, wherein said alkylene or alkenylene radical can be unsubstituted or substituted by halogen, hydroxy, lower alkoxy, amino, lower alkylamino, di-lower alkylamino, carbamoyl, lower alkylcarbamoyl or a radical $-(CH_2)_y-R_{10}$, in which y is 0 to 3, preferably 0 to 2, and $R_{10}$ is hydrogen or phenyl, which is unsubstituted or substituted by halogen, halogen lower alkyl, lower alkoxy, hydroxy, lower alkoxycarbonyl, amino, lower alkylamino, di-lower alkylamino, carbamoyl, lower alkylcarbamoyl, carboxyl, methylenedioxy or cyano, or β) N-(aryl lower alkyl)carbamoyl, or γ) a radical of the formula $-NH-S(=O)_i-R_8$, in which
  i is 1 or 2, R₈ is an aliphatic, carbocyclic or heterocyclic radical; or δ) a radical of the formula —NH—C(=O)—R₉, in which
R₉ is alkoxy, aryloxy, alkenyl, alkynyl, aryl alkynyl, alkynyloxy or aryl alkynyloxy, which in each case is unsubstituted or substituted, the substituents being selected from the group consisting of halogen, hydroxy, phenyl, lower alkyl, lower alkoxy, lower alkoxycarbonyl, amino, lower alkylamino, di-lower alkylamino, carbamoyl, lower alkylcarbamoyl, carboxyl, methylenedioxy, tri-lower alkyl silyl, cyano or lower alkyl which is substituted by halogen, wherein such an unsubstituted or substituted R₉ radical has not more than 20 C atoms;

where, if more than one radical R₁ is present in the molecule, these can be identical or different from one another, R₂ is hydrogen, carbamoyl or N-lower alkyl-carbamoyl, R₃ is lower alkyl, which is unsubstituted or substituted by hydroxy, lower alkoxy, amino, lower alkylamino or N,N-di-lower alkylamino and a) R₄ is hydrogen, amino, phenylamino, lower alkylamino, hydroxyl, phenoxy, lower alkoxy, acyl having 1–30 C atoms, a carbocyclic or carbocyclic-aliphatic radical having not more than 29 C atoms, a heterocyclic or heterocyclic-aliphatic radical having not more than 20 C atoms and not more than 9 heteroatoms, or a substituted hydrocarbon radical having not more than 29 C atoms wherein the substituents are selected from halogen, amino, lower alkylamino, ω-amino-lower alkylamino, lower alkanoylamino, benzoylamino, hydroxylamino, hydroxylimino, lower alkoxy-amino, phenyloxyamino, amino-cyclohexyl-amino-, amino-phenyl-amino-, carbamoyl-amino, (N-lower alkyl-carbamoyl)-amino, (N-[ω-amino-lower alkyl]-carbamoyl)-amino, (N-phenyl-carbamoyl)-amino, lower alkylthio, thiocarbamoyl, thioureido, N-lower alkyl-thioureido, N-phenyl-thioureido, guanidino, N-lower alkyl-guanidino, carboxyl, lower alkoxycarbonyl, phenyloxycarbonyl, benzyloxycarbonyl, hydroxylaminocarbonyl, carbamoyl, amidino, cyano, lower alkoxy, phenyloxy, aminocarbonyl-oxy, oxo, aminosulfonyl, lower alkylsulfonyl-amino, glycylamino, alanylamino, phenylalanylamino, prolylamino, valylamino, leucylamino, isoleucylamino, serylamino, threonylamino, cysteinylamino, methionylamino, tyrosylamino, tryptophanylamino, arginylamino, histidylamino, lysylamino, glutamylamino, glutaminylamino, asparagylamino, asparaginylamino and phenylglycylamino; and R₅, independently of R₄, is as defined above for R₄, with the exception of hydrogen, or b) R₄ and R₅ together are 1,2-ethylene, propane-1,3-diyl, butane-1,4-diyl, pentane-1,5-diyl, 3-(3amino-propionyl)-3-aza-pentane-1,5-diyl, 2-amino-butane-1,4-diyl, 1-aminomethyl-butane-1,4-diyl, 1-hydroxymethyl-butane-1,4-diyl, 3-hydroxy-pentane-1,5-diyl, 1-hydroxy-hexane-1,5-diyl, 3-(2-amino-ethyl)-pentane-1,5-diyl, 3-aza-pentane-1,5-diyl (—CH₂—CH₂—NH—CH₂—CH₂—), 3-aza-2,4-dimethyl-pentane-1,5-diyl (—CH—CH[CH₃]—NH—CH[CH₃]—CH₂—), 3-amino-3-aza-pentane-1,5-diyl (—CH₂—CH₂—N[NH₂]—CH₂—CH₂—), 1-aza-pentane-1,5-diyl, 1-aza-1-toluylaminocarbonyl-pentane-1,5-diyl, 1-aza-1-(methylamino-thiocarbonyl)-pentane-1,5diyl, 1-aza-1-(tert-butylamino-carbonyl)-pentane-1,5-diyl, 1-aza-1-(cyclohexylamino-carbonyl)-pentane-1,5-diyl, 3-aza-1-hydroxy-heptane-3,7-diyl, 3-aza-1-cyano-heptan-3,7-diyl, 1-amino-3-aza-heptane-3,7-diyl, 3-(2-amino-ethyl)-3-aza-pentane-1,5-diyl (—CH₂—CH₂—N[—CH₂—CH₂—NH₂]—CH₂—CH₂—), 1-carbamoyl-butane-1,4-diyl, 2-formylamino-pentene-1,4-diyl, 2-aza-butadiene-1,4-diyl (—CH=CH—N=CH—), 2-aza-3-hydroxymethyl-butadiene-1,4-diyl (—CH=C[CH₂OH]—N=CH—) or a radical of the formula

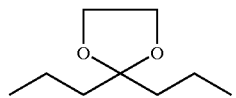

in which the two terminal bonds of the alkylene chain are free valencies, or a salt thereof.

3. A compound of claim 1 of formula I, wherein q is 1–3,

R₁ is

α) —S(=O)ₖ—NR₆R₇, in which
k is 2,
wherein under the proviso that R₈ and R₇ cannot be simultaneously hydrogen
α1) R₆, R₇ can be identical or different from one another and represent an aliphatic, carbocyclic, heterocyclic, carbocyclic-aliphatic or heterocyclic-aliphatic radical; or hydrogen; or
α2) R₆ and R₇ together are an alkylene or alkenylene radical having from 3 up to and including 9 C atoms, in which 1–3 C atoms can be replaced by oxygen, sulfur or nitrogen, wherein said alkylene or alkenylene radical can be unsubstituted or substituted having in each case including the substituents not more than 20 C atoms, the substituents being selected from halogen, hydroxy, lower alkoxy, amino, lower alkylamino, di-lower alkylamino, carbamoyl, lower alkylcarbamoyl or a radical —(CH₂)ᵧ—R₁₀, in which y is 0 to 3, preferably 0 to 2, and R₁₀ is hydrogen or phenyl, which is unsubstituted or substituted by halogen, halogen lower alkyl, lower alkoxy, hydroxy, lower alkoxycarbonyl, amino, lower alkylamino, di-lower alkylamino, carbamoyl, lower alkylcarbamoyl, carboxyl, methylene-dioxy or cyano, or β) N-(aryl lower alkyl)carbamoyl, or γ) a radical of the formula —NH—S(=O)ᵢ—R₆, in which
i is 2, and
R₅ is an aliphatic, carbocyclic or heterocyclic radical; or δ) a radical of the formula —NH—C(=O)—R₉, in which
R₉ is alkoxy, aryloxy, alkynyl, heterocyclyl alkynyl, aryl alkynyl, heteroaryl alkynyl, alkynyloxy or aryl alkynyloxy, which in each case is unsubstituted or substituted, the substituents being selected from the group consisting of halogen, hydroxy, phenyl, lower alkyl, lower alkoxy, lower alkoxycarbonyl, amino, lower alkylamino, di-lower alkylamino, carbamoyl, lower alkylcarbamoyl, carboxyl, methylenedioxy, tri-lower alkyl silyl, cyano or lower alkyl which is substituted by halogen, wherein such an unsubstituted or substituted $R_9$ radical has not more than 20 C atoms;

where, if more than one radical $R_1$ is present in the molecule, these can be identical or different from one another, $R_2$ is hydrogen, $R_3$ is lower alkyl, $R_4$ is hydrogen, amino, phenylamino, lower alkylamino, hydroxyl, phenoxy or lower alkoxy; an acyl radical of the part formula Z—C(=W)— in which W is oxygen, sulfur or imino and Z is hydrogen, hydrocarbyl $R^6$, hydrocarbyloxy $R^6$—O— or an amino group of the formula $R_{11}(R_{12})N$—, in which $R^6$ in each case is $C_1$–$C_4$alkyl, hydroxy-$C_2$–$C_{14}$alkyl, cyano-$C_1$–$C_4$alkyl, carboxy-$C_1$–$C_4$alkyl, $C_1$—$C_4$alkoxycarbonyl-$C_1$–$C_4$alkyl, $C_3$–$C_7$alkenyl or phenyl and $R_{11}$ and $R_{12}$ independently of one another are each hydrogen, lower alkyl, □-amino-lower alkyl, lower alkylsulfonyl or phenyl;

a substituted hydrocarbon radical having not more than 29 C atoms wherein the substituents are selected from halogen, amino, lower alkylamino, ω-amino-lower alkylamino, lower alkanoylamino, benzoylamino, hydroxylamino, hydroxylamino, lower alkoxy-amino, phenyloxyamino, amino-cyclohexyl-amino-, amino-phenyl-amino-, carbamoyl-amino, (N-lower alkyl-carbamoyl)-amino, (N-[ω-amino-lower alkyl]-carbamoyl)-amino, (N-phenyl-carbamoyl)-amino, lower alkylthio, thiocarbamoyl, thioureido, N-lower alkyl-thioureido, N-phenyl-thioureido, guanidino, N-lower alkyl-guanidino, carboxyl, lower alkoxycarbonyl, phenyloxycarbonyl, benzyloxycarbonyl, hydroxylaminocarbonyl, carbamoyl, amidino, cyano, hydroxyl, lower alkoxy, phenyloxy, aminocarbonyl-oxy, oxo, aminosulfonyl, lower alkylsulfonyl-amino, glycylamino, alanylamino, phenylalanylamino, prolylamino, valylamino, leucylamino, isoleucylamino, serylamino, threonylamino, cysteinylamino, methionylamino, tyrosylamino, tryptophanylamino, arginylamino, histidylamino, lysylamino, glutamylamino, glutaminylamino, asparagylamino, asparaginylamino and phenylglycylamino;

benzyl, 2-phenyl-ethyl, 3-aminomethyl-benzyl, (1-hydroxy-cyclohex-1-yl)-methyl, (2-amino-3,5,5,-trimethyl-cyclopentyl)-methyl, 1-[N-(1-carboxy-2-phenyl-ethyl)-carbamoyl]-2-carbamoyl-eth-1-yl, 1-carbamoyl-1-phenyl-methyl, 1-carbamoyl-2-(4-hydroxy-phenyl)-eth-1-yl, 1-carbamoyl-2-phenyl-eth-1-yl, 2-amino-1,2-diphenyl-eth-1-yl, 2-benzyloxycarbonyl-1-carbamoyl-eth-1-yl, 3-benzyloxycarbonyl-1-carbamoyl-prop-1-yl, 1-adamantyl-2-amino-prop-1-yl, 1-adamantyl-1-amino-prop-2-yl, (2-furyl)-methyl, (2-tetrahydrofuryl)-methyl, 2-pyrid-2-yl-ethyl, 2-piperidino-ethyl, 2-(morpholin-4-yl)-ethyl, 2-(3-indolyl)-ethyl, 2-(4-imidazolyl)-ethyl, 1-carbamoyl-2-(β-indolyl)-eth-1-yl, 1-carbamoyl-2-imidazol-4-yl-eth-1-yl, 1-carbamoyl-2-indol-3-yl-eth-1-yl, 3-aminomethyl-oxetan-3-yl-methyl, 1-(acetoxy-imino)-1-(4-amino-2-oxa-1,3-diazol-5-yl)-methyl, $C_4$–$C_5$cycloalkyl, which is substituted by carboxy, thiocarboxy, lower alkoxycarbonyl, hydrazinocarbonyl, hydroxaminocarbonyl, amidino, sulfamoyl, sulfanyl, halogen, cyano, formyl, amino, hydroxy, lower alkoxy, lower aliphatic acyl, lower alkylamino, di-lower alkylamino, carbamoyl, lower alkylcarbamoyl, aminocarbonyloxy or ureido; 2-aminomethyl-3,3,5-trimethyl-cyclopent-1-yl, 3-amino-adamantan-1-yl, 2-carbamoyl-bicyclo[2.2.]hept-5-en-3-yl, 9-amino-spiro[4.4]non-1-yl, 5-amino-2-oxa-1,3-diazol-4-yl, 4-amino-thien-3-yl, 3-carbamoyl-5-(3-[2,4-dichloro-phenyl]-1-oxo-prop-2-en-1-yl)-1,2-thiazol-4-yl, 3-carbamoyl-5-(3-[4-trifluoro-phenyl]-1-oxo-prop-2-en-1-yl)-1,2-thiazol-4-yl, 4-amino-2-(4-carboxy-butyl)-tetrahydrothiophen-3-yl or 3-amino-2-(4-carboxy-butyl)-tetrahydrothiophen-4-yl, and $R_5$, independently of $R_4$, is as defined above for $R_4$, with the exception of hydrogen, or $R_4$ and $R_5$ together are 1,2-ethylene, propane-1,3-diyl, butane-1,4-diyl, pentane-1,5-diyl, 3-(3-amino-propionyl)-3-aza-pentane-1,5-diyl, 1-aminomethyl-butane-1,4-diyl, 1-hydroxy-methyl-butane-1,4-diyl, 3-(2-amino-ethyl)-pentane-1,5-diyl, 3-aza-pentane-1,5-diyl or 3-(2-amino-ethyl)-3-aza-pentane-1,5-diyl, or a salt thereof, with the exception of 6-(4-benzyloxycarbonylamino-phenyl-amino)-9-ethyl-2-(2-hydroxy-ethyl-amino)-9H-purine or a salt thereof wherein in the above definitions hydrocarbyl is either: 1) an acyclic, carbocyclic, or carbocyclic-acyclic radical having no more than 29 carbon atoms, or 2) an acyclic, carbocyclic, or carbocyclic-acyclic radical interrupted by one or more identical or different heteroatoms selected from oxygen, sulfur, and nitrogen having a total of no more than 29 C, O, S, and N atoms.

4. A compound of claim 1 of formula I, wherein q is 1–3, $R_1$ is

α) —S(=O)$_k$—NR$_6$R$_7$, in which k is 2, wherein under the proviso that $R_6$ and $R_7$ cannot be simultaneously hydrogen α1) $R_6$, $R_7$ can be identical or different from one another and represent an aliphatic, carbocyclic, heterocyclic, carbocyclic-aliphatic or heterocyclic-aliphatic radical; or hydrogen; or α2) $R_6$ and $R_7$ together are an alkylene or alkenylene radical having from 3 up to and including 9 C atoms, in which 1–3 C atoms can be replaced by oxygen, sulfur or nitrogen, wherein said alkylene or alkenylene radical can be unsubstituted or substituted having in each case including the substituents not more than 20 C atoms, the substituents being selected from halogen, hydroxy, lower alkoxy, amino, lower alkylamino, di-lower alkylamino, carbamoyl, lower alkylcarbamoyl or a radical —(CH$_2$)$_y$—R$_{10}$, in which y is 0 to 3, preferably 0 to 2, and $R_{10}$ is hydrogen or phenyl, which is unsubstituted or substituted by halogen, halogen lower alkyl, lower alkoxy, hydroxy, lower alkoxycarbonyl, amino, lower alkylamino, di-lower alkylamino, carbamoyl, lower alkylcarbamoyl, carboxyl, methylenedioxy or cyano, or β) N-(aryl lower alkyl)carbamoyl, or γ) a radical of the formula —NH—S(=O)$_t$—R$_6$, in which i is 2, $R_8$ is an aliphatic, carbocyclic or heterocyclic radical; or δ) a radical of the formula —NH—C(=O)—$R_9$, in which
$R_9$ is alkoxy, phenoxy, alkynyl or aryl alkynyl which in each case is unsubstituted or substituted, the substituents being selected from the group consisting of halogen, hydroxy, phenyl, lower alkyl, lower alkoxy, lower alkoxycarbonyl, amino, lower alkylamino, di-lower alkylamino, carbamoyl, lower alkylcarbamoyl, carboxyl, methylenedioxy, tri-lower alkyl silyl, cyano or lower alkyl which is substituted by halogen, wherein such an unsubstituted or substituted $R_9$ radical has not more than 20 C atoms;

where, if more than one radical $R_1$ is present in the molecule, these can be identical or different from one another, $R_2$ is hydrogen, $R_3$ lower alkyl, $R_4$ is hydrogen or $C_5$–$C_7$ cycloalkyl, which is substituted by amino, hydroxy, lower alkoxy, lower alkylamino, di-lower alkylamino, carbamoyl, lower alkylcarbamoyl, aminocarbonyloxy or ureido;

$R_5$ independently of $R_4$, is as defined above for $R_4$, with the exception of hydrogen, or a salt thereof.

5. A compound of claim 1 of formula I, wherein q is 1–2, $R_1$ is —S(=O)$_k$—N$R_6R_7$, in which k is 2, wherein under the proviso that $R_6$ and $R_7$ cannot be simultaneously hydrogen α1) $R_8$, $R_7$ can be identical or different from one another and represent hydrogen;
$C_1$–$C_{12}$ alkyl which is unsubstituted or substituted by hydroxy, lower alkoxy, halogen, amino, lower alkylamino, di-lower alkylamino, unsubstituted heteroaryl having not more than 10 carbon atoms and not more than 3 heteroatoms or aryl having not more than 14 carbon atoms which is unsubstituted or substituted by halogen, lower alkyl, lower alkoxy, phenoxy, lower alkoxycarbonyl, imidazolyl, morpholinyl, pyrrolidinyl, piperidinyl, piperazinyl, amino, lower alkylamino, di-lower alkylamino, carbamoyl or lower alkyl which substituted by halogen;
$C_3$–$C_{10}$ cycloalkyl which is unsubstituted or substituted by hydroxy, amino, lower alkylamino, di-lower alkylamino, carbamoyl or lower alkylcarbamoyl;
unsubstituted heteroaryl having not more than 20 carbon atoms and not more than 3 heteroatoms;
aryl having not more than 20 carbon atoms unsubstituted or substituted by halogen, lower alkyl, lower alkoxy, phenoxy, lower alkoxycarbonyl, imidazolyl, morpholinyl, pyrrolidinyl, piperidinyl, piperazinyl, amino, lower alkylamino, di-lower alkylamino, carbamoyl or lower alkyl which is substituted by halogen; or α2) $R_6$ and $R_7$ together are an alkylene or alkenylene radical having from 3 up to and including 9 C atoms, in which 1–3 C atoms can be replaced by oxygen or nitrogen, wherein said alkylene or alkenylene radical can be unsubstituted or substituted having in each case including the substituents not more than 20 C atoms, the substituents being selected from halogen, hydroxy, lower alkoxy, amino, lower alkylamino, di-lower alkylamino, carbamoyl, lower alkylcarbamoyl or a radical —(CH$_2$)$_y$—$R_{10}$, in which y is 0 to 3, preferably 0 to 2, and $R_{10}$ is hydrogen or phenyl, which is unsubstituted or substituted by halogen, halogen lower alkyl, lower alkoxy, hydroxy, lower alkoxycarbonyl, amino, lower alkylamino, di-lower alkylamino, carbamoyl, lower alkylcarbamoyl, carboxyl, methylenedioxy or cyano;

where, if more than one radical $R_1$ is present in the molecule, these can be identical or different from one another, $R_2$ is hydrogen, $R_3$ is lower alkyl, $R_4$ is hydrogen or $C_5$–$C_7$ cycloalkyl, which is substituted by amino, hydroxy, lower alkoxy, lower alkylamino, di-lower alkylamino, carbamoyl, lower alkylcarbamoyl, aminocarbonyloxy or ureido;

$R_5$, independently of $R_4$, is as defined above for $R_4$, with the exception of hydrogen, or a salt thereof.

6. A compound of claim 1 of formula I, wherein

β) $R_1$ is N-(phenyl lower alkyl)carbamoyl, wherein phenyl is unsubstituted or substituted by halogen, lower alkyl, hydroxy, lower alkoxy, phenoxy, amino, lower alkylamino, di-lower alkylamino or lower alkyl which is substituted by halogen; or γ) $R_1$ is a radical of the formula —NH—S(=O)$_i$—$R_8$, in which i is 2, $R_8$ is
lower alkyl, lower alkyl which is substituted by halogen;
$C_3$–$C_8$ a cycloalkyl, which is unsubstituted or substituted by halogen, hydroxy, lower alkoxy, amino, lower alkylamino, di-lower alkylamino or carbamoyl;
unsubstituted heteroaryl having not more than 20 carbon atoms and not more than 3 heteroatoms;
phenyl which is unsubstituted or substituted by halogen, lower alkyl, hydroxy, lower alkoxy, amino, lower alkylamino, di-lower alkylamino or lower alkyl which is substituted by halogen; or γ) $R_1$ is a radical of the formula —NH—C(=O)—$R_9$,
$R_9$ is
alkoxy, phenoxy, alkynyl, which is unsubstituted or substituted by tri(lower alkyl)silyl; heteroaryl alkynyl, wherein the heteroaryl moiety comprises one or two heteroatoms selected from the group consisting of nitrogen, sulfur and oxygen, and which radical is unsubstituted or substituted by halogen, hydroxy, lower alkyl, lower alkoxy, phenyl, amino, lower alkylamino, di-lower alkylamino or lower alkyl which is substituted by halogen; heterocyclyl alkynyl, wherein the heterocyclyl moiety comprises one or two heteroatoms selected from the group consisting of nitrogen, sulfur and oxygen, and which radical is unsubstituted or substituted by halogen, hydroxy, lower alkyl, lower alkoxy, phenyl, amino, lower alkylamino, di-lower alkylamino or lower alkyl which is substituted by halogen; or phenyl alkynyl, which is unsubstituted or substituted by halogen, hydroxy, lower alkyl, lower alkoxy, phenyl, amino, lower alkylamino, di-lower alkylamino or lower alkyl which is substituted by halogen;

where, if more than one radical $R_1$ is present in the molecule, these can be identical or different from one another, R$_2$ is hydrogen.

R$_3$ is lower alkyl,

R$_4$ is hydrogen or C$_5$–C$_7$ cycloalkyl, which is substituted by amino, hydroxy, lower alkoxy, lower alkylamino, di-lower alkylamino, carbamoyl, lower alkylcarbamoyl, aminocarbonyloxy or ureido;

R$_5$, independently of R$_4$, is as defined above for R$_4$, with the exception of hydrogen, or a salt thereof.

7. A compound of claim 1 of formula I, wherein q is 1,

R$_1$ is

α) —S(=O)$_k$—NR$_6$R$_7$, in which k is 2, wherein under the proviso that R$_6$ and R$_7$ cannot be simultaneously hydrogen α1) R$_6$, R$_7$ can be identical or different from one another and represent hydrogen, C$_1$–C$_6$ alkyl, hydroxy lower alkyl, phenyl unsubstituted or substituted by phenoxy, lower alkoxy, imidazolyl, lower alkyl, halogen, halogen lower alkyl, lower alkyloxycarbonyl or morpholinyl; lower alkyl substituted by phenyl, halogenphenyl, naphthyl, furanyl or pyridyl; C$_3$–C$_8$ cycloalkyl unsubstituted or substituted by hydroxy; tetrahydronaphthyl or quinolinyl; or α2) R$_6$ and R$_7$ together are an alkylene radical α2.1) having from 4 up to and including 6 C atoms, in which 1 C atom can be replaced by oxygen; or α2.2) a radical of the formula (II),

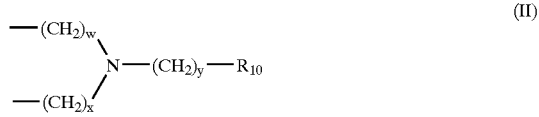

(II)

in which w is 2, x is 2, y is 0 or 1 and R$_{10}$ is hydrogen or phenyl, which is unsubstituted or substituted by halogen, trifluoromethyl or lower alkoxy, β) unsubstituted or substituted phenyl lower alkylcarbamoyl, in which case phenyl can be substituted by halogen, lower alkyl, lower alkoxy or trifluoromethyl; or γ) a radical of the formula —NH—S(=O)$_i$—R$_8$, in which i is 2, and R$_8$ is lower alkyl or phenyl substituted by lower alkyl or lower alkoxy; or δ) a radical of the formula —NH—C(=O)—R$_9$, in which R$_9$ is lower alkoxy, phenoxy, phenyl lower alkynyl, in which phenyl is unsubstituted or substituted by halogen, lower alkyl or lower alkoxy; lower alkynyl or tri(lower alkyl) silyl lower alkynyl, where, if more than one radical R$_1$ is present in the molecule, these can be identical or different from one another, R$_2$ is hydrogen, R$_3$ is lower alkyl, R$_4$ is hydrogen, and R$_5$ is cyclohexyl, which is substituted by amino, hydroxy or carbamoyl, or a salt thereof.

8. A compound of claim 1 formula I, wherein q is 1–3,

R$_1$ is a radical of the formula —NH—C(=O)—R$_9$, in which R$_9$ is alkoxy, phenoxy, alkynyl, which is unsubstituted or substituted by tri(lower alkyl)silyl; heteroaryl alkynyl, wherein the heteroaryl moiety is selected from the group consisting of pyridyl, pyrimidyl, thienyl, furyl, oxazolyl and thiazolyl and which radical is unsubstituted or substituted by halogen, hydroxy, lower alkyl, lower alkoxy, phenyl, amino, lower alkylamino, di-lower alkylamino or lower alkyl which is substituted by halogen; heterocyclyl alkynyl, wherein the heterocyclyl moiety is selected from the group consisting of piperidinyl, pyrrolidinyl, piperazinyl, lower alkyl piperazinyl, morpholinyl and thiamorpholinyl, and which radical is unsubstituted or substituted by halogen, hydroxy, lower alkyl, lower alkoxy, phenyl, amino, lower alkylamino, di-lower alkylamino or lower alkyl which is substituted by halogen; or phenyl alkynyl, which is unsubstituted or substituted by halogen, hydroxy, lower alkyl, lower alkoxy, phenyl, amino, lower alkylamino, di-lower alkylamino or lower alkyl which is substituted by halogen;

where, if more than one radical R$_1$ is present in the molecule, these can be identical or different from one another, R$_2$ is hydrogen, R$_3$ is lower alkyl, R$_4$ is hydrogen or C$_5$–C$_7$ cycloalkyl, which is substituted by amino, hydroxy, lower alkoxy, lower alkylamino, di-lower alkylamino, carbamoyl, lower alkylcarbamoyl, aminocarbonyloxy or ureido;

R$_5$, independently of R$_4$ is as defined above for R$_4$, with the exception of hydrogen or a pharmaceutically acceptable salt thereof.

9. A compound of claim 1 of formula I, wherein q is 1–2,

R$_1$ is a radical of the formula —NH—C(=O)—R$_9$, in which R$_9$ is alkoxy, phenoxy, alkynyl, which is unsubstituted or substituted by tri(lower alkyl)silyl; heteroaryl alkynyl, wherein the heteroaryl moiety is selected from the group consisting of pyridyl, pyrimidyl and thienyl, and which radical is unsubstituted or substituted by lower alkyl; heterocyclyl alkynyl, wherein the heterocyclyl moiety is selected from the group consisting of piperidinyl and piperazinyl, and which radical is unsubstituted or substituted by lower alkyl; or phenyl alkynyl, which is unsubstituted or substituted by halogen, hydroxy, lower alkyl, lower alkoxy, phenyl, amino, lower alkylamino, di-lower alkylamino or lower alkyl which is substituted by halogen;

where, if more than one radical R$_1$ is present in the molecule, these can be identical or different from one another, R$_2$ is hydrogen, R$_3$ is lower alkyl, R$_4$ is hydrogen or C$_5$–C$_7$ cycloalkyl, which is substituted by amino, hydroxy, lower alkoxy, lower alkylamino, di-lower alkylamino, carbamoyl, lower alkylcarbamoyl, aminocarbonyloxy or ureido;

R$_5$, independently of R$_4$, is as defined above for R$_4$, with the exception of hydrogen or a pharmaceutically acceptable salt thereof.

10. A compound of claim 1 of formula I selected from the group consisting of cis-2-[6-(4-Butyl-aminosulfonyl-phenylamino)-9-ethyl-9H-purin-2-yl-amino]-cyclohexanecarboxylic acid amide cis-2-{9-Ethyl-6-[4-(3-methylbutyl)-aminosulfonyl-phenylamino]-9H-purin-2-yl-amino}-cyclohexanecarboxylic acid amide cis-2-[9-Ethyl-6-(4-isobutyl-amino-sulfonyl-phenylamino)-9H-purin-2-yl-amino]-cyclohexanecarboxylic acid amide cis-2-{9-Ethyl-6-[4-(4-phenyl-piperazin-1-yl-sulfonyl)-phenylamino]-9H-purin-2-yl-amino}-cyclohexanecarboxylic acid amide 4-[2-(trans-4-Amino-cyclohexylamino)-9-ethyl-9H-purin-6-yl-amino]-phenyl-N-(3-methyl-butyl)-sulfonamide 4-[2-(trans-4-Amino-cyclohexylamino)-9-ethyl-9H-purin-6-yl-amino]-phenyl-N-butyl-sulfonamide 4-[2-(trans-4-Amino-cyclohexylamino)-9-ethyl-9H-purin-6-yl-amino]-phenyl-N-isobutyl-sulfonamide 4-[2-(trans-4-Amino-cyclohexylamino)-9-ethyl-9H-purin-6-yl-amino]-phenyl-N-cyclohexyl-sulfonamide cis-2-[8-(4-Cyclohexyl-aminosulfonyl-phenylamino)-9-ethyl-9H-purin-2-yl-amino]-cyclohexanecarboxylic acid amide N-2-(trans-4-Amino-cyclohexyl)-9-ethyl-N-6-[4-(piperidine-1-sulfonyl)-phenyl]-9H-purine-2,6-diamine cis-2-{9-Ethyl-6-[4-(piperidine-1-sulfonyl)-phenyl amino]-9H-purin-2-yl-amino}-cyclohexanecarboxylic acid amide cis-2-{6-[4-(N-Butyl-N-methyl-amino-sulfonyl)-phenylamino]-9-ethyl-9H-purin-2-yl-amino}-cyclohexanecarboxylic acid amide 4-[2-(trans-4-Amino-cyclohexylamino)-9-ethyl-9H-purin-6-yl-amino]-phenyl-N-butyl-N-methyl-sulfonamide cis-2-{9-Ethyl-6-[4-(N-methyl-N-phenyl-aminosulfonyl)-phenylamino]-9H-purin-2-yl-amino}-cyclohexanecarboxylic acid amide 4-[2-(trans-4-Amino-cyclohexylamino)-9-ethyl-9H-purin-6-yl-amino]-phenyl-N-methyl-N-phenyl-sulfonamide N-2-(trans-4-Amino-cyclohexyl)-9-ethyl-N-6-[4-(4-phenyl-piperazine-1-sulfonyl)-phenyl]-9H-purine-2,6-diamine 4-[9-Ethyl-2-(trans-4-hydroxy-cyclohexylamino)-9H-purin-6-yl-amino]-phenyl-N-isobutyl-N-methyl-sulfonamide trans-4-(9-Ethyl-6-{4-[4-(4-fluoro-phenyl)-piperazine-1-sulfonyl]-phenylamino}-9H-purin-2-yl-amino)-cyclohexanol trans-4-(9-Ethyl-6-{4-[4-(3trifluoromethyl-phenyl)-piperazine-1-sulfonyl]-phenylamino}-9H-purin-2-yl-amino)-cyclohexanol trans-4-(9-Ethyl-6-{4-[4-(2-methoxy-phenyl)-piperazine-1-sulfonyl]-phenylamino}-9H-purin-2yl-amino)-cyclohexanol N-Cyclohexyl-{4-[9-ethyl-2-(trans-4-hydroxy-cyclohexylamino)-9H-purin-6-yl-amino]-phenyl}-N-methyl-sulfonamide trans-4-{9-Ethyl-6-[4-(pyrrolidine-1-sulfonyl)-phenylamino]-9H-purin-2-yl-amino}-cyclohexanol trans-4-{6-[4-(Azepane-1-sulfonyl)-phenylamino]-9-ethyl-9H-purin-2-yl-amino}-cyclohexanol 4-[9-Ethyl-2-(trans-4-hydroxy-cyclohexyl-amino)-9H-purin-6-yl-amino]-phenyl-N-(4-methoxy-phenyl)-N-methyl-sulfonamide 4-[9-Ethyl-2-(trans-4-hydroxy-cyclohexyl-amino)-9H-purin-6-yl-amino]-phenyl-N-(2-pyridin-2-yl-ethyl)-sulfonamide trans-4-{6-[4-(4-Benzyl-piperazine-1-sulfonyl)-phenylamino]-9-ethyl-9H-purin-2-yl-amino}-cyclohexanol 4-[9-Ethyl-2-(trans-4-hydroxy-cyclohexyl-amino)-9H-purin-6-yl-amino]-phenyl-N-(trans-4-hydroxy-cyclohexyl)-sulfonamide 4-[9-Ethyl-2-(trans-4-hydroxy-cyclohexyl-amino)-9H-purin-6-yl-amino]-phenyl-N-naphthalen-1-yl-methyl-sulfonamide 4-[9-Ethyl-2-(trans-4-hydroxy-cyclohexyl-amino)-9H-purin-6-yl-amino]-phenyl-N-heptyl-N-methyl-sulfonamide N-(3,3-Diphenyl-propyl)-4-[9-ethyl-2-(trans-4-hydroxy-cyclohexylamino)-9H-purin-6yl-amino]-phenyl-sulfonamide 4-[9-Ethyl-2-(trans-4-hydroxy-cyclohexyl-amino)-9H-purin-6-yl-amino]-phenyl-N-(1-methyl-3-phenyl-propyl)-sulfonamide 4-[9-Ethyl-2-(trans-4-hydroxy-cyclohexyl-amino)-9H-purin-6-yl-amino]-phenyl-N-(3-methyl-butyl)-sulfonamide trans-4-{9-Ethyl-6-[4-(piperidine-1-sulfonyl)-phenylamino]-9H-purin-2-yl-amino}-cyclohexanol N-(3-Chloro-benzyl)-4-[9-ethyl-2-(trans-4-hydroxy-cyclohexylamino)-9H-purin-6-yl-amino]-phenyl-sulfonamide 4-[9-Ethyl-2-(trans-4-hydroxy-cyclohexyl-amino)-9H-purin-6yl-amino]-phenyl-N-(3-imidazol-1-yl-phenyl)-sulfonamide)

N-(3,4-Dimethoxy-phenyl)-4-[9-ethyl-2-(trans-4-hydroxy-cyclohexylamino)-9H-purin-6-yl-amino]-phenyl-sulfonamide 4-[9-Ethyl-2-(trans-4-hydroxy-cyclohexyl-amino)-9H-purin-6-yl-amino]-phenyl-N-(5-fluoro-2-methyl-phenyl)-sulfonamide N-(3,5-Dimethoxy-phenyl)-4-[9-ethyl-2-(trans-4-hydroxy-cyclohexylamino)-phenyl-9H-purin-6-yl-amino]-phenyl-sulfonamide 4-[9-Ethyl-2-(trans-4-hydroxy-cyclohexyl-amino)-9H-purin-6-yl-amino]-phenyl-N-methyl-N-phenyl-sulfonamide 4-[9-Ethyl-2-(trans-4-hydroxy-cyclohexyl-amino)-9H-purin-6-yl-amino]-phenyl-N-(5,6,7,8-tetrahydro-1-naphthyl)-sulfonamide N-Benzyl-4-[9-ethyl-2-(trans-4-hydroxy-cyclohexylamino)-9H-purin-6-yl-amino]-phenyl-N-phenyl-sulfonamide 4-{4-[9-Ethyl-2-(trans-4-hydroxy-cyclohexylamino)-9H-purin-6-yl-amino]-phenyl-sulfonylamino}-benzoic acid propyl ester 4-[9-Ethyl-2-(trans-4-hydroxy-cyclohexyl-amino)-9H-purin-6-yl-amino]-phenyl-N-(4-morpholin-4-yl-phenyl)-sulfonamide 4-[9-Ethyl-2-(trans-4-hydroxy-cyclohexyl-amino)-9H-purin-6-yl-amino]-phenyl-N-quinolin-3-yl-sulfonamide 4-[9-Ethyl-2-(trans-4-hydroxy-cyclohexyl-amino)-9H-purin-6-yl-amino]-phenyl-N-(4-phenoxy-phenyl)-sulfonamide N-(2,4-Eimethyl-phenyl)-4-[9-ethyl-2-(trans-4-hydroxy-cyclohexylamino)-9H-purin-6-yl-amino]-phenyl-sulfonamide 4-[9-Ethyl-2-(trans-4-hydroxy-cyclohexyl-amino)-9H-purin-6-yl-amino]-phenyl-N-m-tolyl-sulfonamide)

4-[9-Ethyl-2-(trans-4-hydroxy-cyclohexyl-amino)-9H-purin-6-yl-amino]-phenyl-N-o-tolyl-sulfonamide 4-[9-Ethyl-2-(trans-4-hydroxy-cyclohexyl-amino)-9H-purin-6-yl-amino]-phenyl-N-(3-trifluoromethyl-phenyl)-sulfonamide N-(3,4-Dichloro-phenyl)-4-[9-ethyl-2-(trans-4-hydroxy-cyclohexylamino)-9H-purin-6yl-amino]-phenyl-sulfonamide N-(3-Chloro-phenyl)-4-[9-ethyl-2-(trans-4-hydroxy-cyclohexylamino)-9H-purin-6-yl-amino]-phenyl-sulfonamide 4-[9-Ethyl-2-(trans-4-hydroxy-cyclohexyl-amino)-9H-purin-6-yl-amino]-phenyl-N-phenyl-sulfonamide 4-[9-Ethyl-2-(trans-4-hydroxy-cyclohexyl-amino)-9H-purin-6-yl-amino]-phenyl-N-propyl-sulfonamide N-Butyl-4-[9-ethyl-2-(trans-4-hydroxy-cyclohexyl-amino)-9H-purin-6-yl-amino]-phenyl-N-methyl-sulfonamide trans-4-{9-Ethyl-6-[4-(4-phenyl-piperazine-1-sulfonyl)-phenylamino]-9H-purin-2-yl-amino}-cyclohexanol 4-[9-Ethyl-2-(trans-4-hydroxy-cyclohexyl-amino)-9H-purin-6-yl-amino]-phenyl-N-3-pyridylmethyl-sulfonamide 4-[9-Ethyl-2-(trans-4-hydroxy-cyclohexyl-amino)-9H-purin-6-yl-amino]-phenyl-N-2-furanylmethyl-sulfonamide N-Benzyl-N-ethyl-4-[9-ethyl-2-(trans-4-hydroxy-cyclohexylamino)-9H-purin-6-yl-amino]-phenyl-sulfonamide N-Cyclohexyl-4-[9-ethyl-2-(trans-4-hydroxy-cyclohexylamino)-9H-purin-6-yl-amino]-phenyl-sulfonamide N-Cyclopropyl-4-[9-ethyl-2-(trans-4-hydroxy-cyclohexylamino)-9H-purin-6-yl-amino]-phenyl-sulfonamide 4-[9-Ethyl-2-(trans-4-hydroxy-cyclohexyl-amino)-9H-purin-6-yl-amino]-phenyl-N-(3-hydroxy-propyl)-sulfonamide 4-[9-Ethyl-2-(trans-4-hydroxy-cyclohexyl-amino)-9H-purin-6-yl-amino]-phenyl-N-isobutyl-sulfonamide N,N-Dibutyl-4-[9-ethyl-2-(trans-4-hydroxy-cyclohexylamino)-9H-purin-6-yl-amino]-phenyl-sulfonamide 4-[9-Ethyl-2-(trans-4-hydroxy-cyclohexyl-amino)-9H-purin-6-yl-amino]-phenyl-N-octyl-sulfonamide trans-4-{9-Ethyl-6-[4-(morpholine-4-sulfonyl)-phenyl-amino]-9H-purin-2-yl-amino}-cyclohexanol trans-4-{9-Ethyl-6-[4-methyl-piperazine-1-sulfonyl)-phenyl-amino]-9H-purin-2-yl-amino}-cyclohexanol N-Butyl-4-[9-ethyl-2-(trans-4-hydroxy-cyclohexyl-amino)-9H-purin-6-yl-amino]-phenyl-sulfonamide 4-[9-Ethyl-2-(trans-4-hydroxy-cyclohexyl-amino)-9H-purin-6-yl-amino]-phenyl-N-isopropyl-sulfonamide N-Benzyl-4-[9-ethyl-2-(trans-4-hydroxy-cyclohexyl-amino)-9H-purin-6yl-amino]-phenyl-sulfonamide 4-[9-Ethyl-2-(trans-4-hydroxy-cyclohexyl-amino)-9H-purin-6-yl-amino]-phenyl-N-methyl-sulfonamide 4-[9-Ethyl-2-(trans-4-hydroxy-cyclohexyl-amino)-9H-purin-6-yl-amino]-phenyl-N,N-dimethyl-sulfonamide N-Benzyl-3-[9-ethyl-2-(trans-4-hydroxy-cyclohexylamino)-9H-purin-6yl-amino]-benzamide 3-[9-Ethyl-2-(trans-4-hydroxy-cyclohexylamino)-9H-purin-6-yl-amino]-N-(4-fluoro-benzyl)-benzamide 3-[9-Ethyl-2-(trans-4-hydroxy-cyclohexylamino)-9H-purin-6-yl-amino]-N-(4-methyl-benzyl)-benzamide 3-[9-Ethyl-2-(trans-4-hydroxy-cyclohexylamino)-9H-purin-6-yl-amino]-N-(4-methoxy-benzyl)-benzamide 3-[9-Ethyl-2-(trans-4-hydroxy-cyclohexylamino)-9H-purin-6-yl-amino]-N-(4-trifluoromethyl-benzyl)-benzamide N-{4-[9-Ethyl-2-(trans-4-hydroxy-cyclohexylamino)-9H-purin-6-yl-amino]-phenyl}-methane-sulfonamide N-{4-[9-Ethyl-2-(trans-4-hydroxy-cyclo-hexylamino)-9H-purin-6-yl-amino]-phenyl}-4-methyl-benzenesulfonamide N-{4-[9-Ethyl-2-(trans-4-hydroxy-cyclo-hexylamino)-9H-purin-6-yl-amino]-phenyl}-4-methoxy-benzenesulfonamide N-{3-[9-Ethyl-2-(trans-4-hydroxy-cyclo-hexylamino)-9H-purin-6-yl-amino]-phenyl}-methanesulfonamide N-{3-[9-Ethyl-2-(trans-4-hydroxy-cyclo-hexylamino)-9-H-purin-6-yl-amino]-phenyl}-4-methyl-benzenesulfonamide N-{3-[9-Ethyl-2-(trans-4-hydroxy-cyclo-hexylamino)-9H-purin-6-yl-amino]-phenyl}-4-methoxy-benzenesulfonamide {4-[9-Ethyl-2-(trans-4-hydroxy-cyclo-hexylamino)-9H-purin-6-yl-amino]-phenyl}-carbamic acid methyl ester {4-[9-Ethyl-2-(trans-4-hydroxy-cyclo-hexylamino)-9H-purin-6-yl-amino]-phenyl}-carbamic acid isobutyl ester {4-[9-Ethyl-2-(trans-4-hydroxy-cyclo-hexylamino)-9H-purin-6-yl-amino]-phenyl}-carbamic acid phenyl ester {3-[9-Ethyl-2-(trans-4-hydroxy-cyclo-hexylamino)-9H-purin-6-yl-amino]-phenyl}-carbamic acid methyl ester {3-[9-Ethyl-2-(trans-4-hydroxy-cyclo-hexylamino)-9H-purin-6-yl-amino]-phenyl}-carbamic acid isobutyl ester {3-[9-Ethyl-2-(trans-4-hydroxy-cyclo-hexylamino)-9H-purin-6-yl-amino]-phenyl}-carbamic acid phenyl ester N-{3-[9-Ethyl-2-(trans-4-hydroxy-cyclo-hexylamino)-9H-purin-6-yl-amino]-phenyl}-3-trimethylsilylpropargylic acid amide N-{3-[9-Ethyl-2-(trans-4-hydroxy-cyclo-hexylamino)-9H-purin-6-yl-amino]-phenyl}-3-phenylpropargylic acid amide)

N-{3-[9-Ethyl-2-(trans-4-hydroxy-cyclo-hexylamino)-9H-purin-6-yl-amino]-phenyl}-4,4-dimethyl-2-pentynylic acid amide N-{3-[9-Ethyl-2-(trans-4-hydroxy-cyclo-hexylamino)-9H-purin-6-yl-amino]-phenyl}-3-(4-chlorophenyl)-propargylic acid amide N-{3-[9-Ethyl-2-(trans-4-hydroxy-cyclo-hexylamino)-9H-purin-6-yl-amino]-phenyl}-3-(4-fluorophenyl)-propargylic acid amide N-{3-[9-Ethyl-2-(trans-4-hydroxy-cyclo-hexylamino)-9H-purin-6-yl-amino]-phenyl}-3-p-tolylpropargylic acid amide N-{3-[9-Ethyl-2-(trans-4-hydroxy-cyclo-hexylamino)-9H-purin-6-yl-amino]-phenyl}-3-(4-methoxyphenyl)-propargylic acid amide 3-(4-Chloro-phenyl)-propynoic acid-N-{3-[2-(4-hydroxy-cyclohexylamino)-9-isopropyl-9H-purin-6-ylamino]-phenyl}-amide 3-p-Tolyl-propynoic acid-N-{3-[2-(4-hydroxy-cyclohexylamino)-9-isopropyl-9H-purin-6-ylamino]-phenyl}-amide 3-(4-Methoxy-phenyl)-propynoic acid-N-{3-[2-(4-hydroxy-cyclohexyl-amino)-9-isopropyl-9H-purin-6-ylamino]-phenyl}-amide 3-(4-Fluoro-phenyl)-propynoic acid-N-{3-[2-(4-hydroxy-cyclohexylamino)-9-isopropyl-9H-purin-6-ylamino]-phenyl}-amide 3-(Phenyl)-propynoic acid-N-{3-[2-(4-hydroxy-cyclohexylamino)-9-isopropyl-9H-purin-6-ylamino]-phenyl}-amide Biphenyl-4-carboxylic acid-N-{3-[2-(4-hydroxy-cyclohexylamino)-9-isopropyl-9H-purin-6-ylamino]-phenyl}-amide 3-m-Tolyl-propynoic acid-N-{3-[9-ethyl-2-(4-hydroxy-cyclohexylamino)-9H-purin-6-ylamino]-phenyl}-amide 3-(3-Trifluoromethyl-phenyl)-propynoic acid-N-{3-[9-ethyl-2-(4-hydroxy-cyclohexylamino)-9H-purin-6-ylamino]-phenyl}-amide 4,4-Dimethyl-pent-2-ynoic acid-N-{3-[9-ethyl-2-(4-hydroxy-cyclohexylamino)-9H-purin-6-ylamino]-phenyl}-amide 3-(6-Methyl-pyridin-2-yl)-propynoic acid-N-{3-[9-ethyl-2-(4-hydroxy-cyclohexylamino)-9H-purin-6-ylamino]-phenyl}-amide 3-(4-Methyl-pyrimidin-2-yl)-propynoic acid-N-{3-[9-ethyl-2-(4-hydroxy-cyclohexylamino)-9H-purin-6-ylamino]-phenyl}-amide N-{3-[9-Ethyl-2-(trans-4-hydroxy-cyclo-hexylamino)-9H-purin-6-ylamino]-phenyl}-3-(2,6-dichlorophenyl)-propargylic acid amide N-{3-[9-Ethyl-2-(trans-4-hydroxy-cyclo-hexylamino)-9H-purin-6-ylamino]-phenyl}-3-(2-thiophenyl)-propargylic acid amide N-{3-[9-Ethyl-2-(trans-4-hydroxy-cyclo-hexylamino)-9-H-purin-6-ylamino]-phenyl}-3-(2,5-dimethyl-phenyl)-propargylic amide N-{3-[9-Ethyl-2-(trans-4-hydroxy-cyclo-hexylamino)-9H-purin-6-yl-amino]-phenyl}-3-(3,4-dimethyl-phenyl)-propargylic acid amide 4-Piperidin-1-yl-but-2-ynoic acid-N-{3-[9-ethyl-2-(4-hydroxy-cyclohexyl-amino)-9H-purin-6-ylamino]-phenyl}-amide 4-(4-Methyl-piperazin-1-yl)-but-2-ynoic acid-N-{3-[9-ethyl-2-(4-hydroxy-cyclohexylamino)-9H-purin-6-ylamino]-phenyl}-amide and the pharmaceutical acceptable salts thereof.

11. A method of treating osteoporosis in warm-blooded animals, including humans, in which a dose which is effective against osteoporosis of a compound of claim 1 of formula I or of a pharmaceutically acceptable salt of such a compound is administered to such a warm-blooded animal suffering from osteoporosis.

12. A process for the preparation of a compound of the formula I

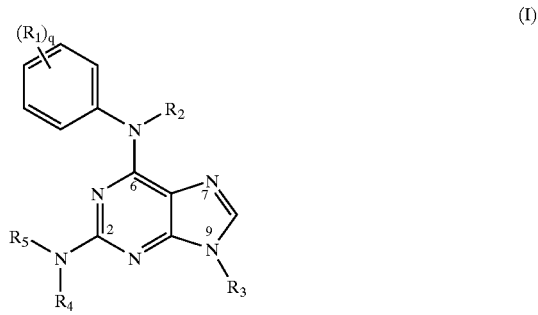

in which q is 1–5, $R_1$ is

α) —(=O)$_k$—NR$_6$R$_7$, in which
  k is 1 or 2,
  wherein under the proviso that $R_6$ and $R_7$ cannot be simultaneously hydrogen
    α1) $R_6$, $R_7$ can be identical or different form one another and represent an aliphatic, carbocyclic, heterocyclic, carbocyclic-aliphatic or heterocyclic-aliphatic radical; hydrogen or lower aliphatic acyl; or
    α2) $R_6$ and $R_7$ together are an alkylene or alkenylene radical having from 3 up to and including 9 C atoms, in which 1–3 C atoms can be replaced by oxygen, sulfur or nitrogen, wherein said alkylene or alkenylene radical can be unsubstituted or substituted by halogen, hydroxy, lower alkoxy, amino, lower alkylamino, di-lower alkylamino, carbamoyl, lower alkylcarbamoyl or a radical —(CH$_2$)$_y$—$R_{10}$, in which y is 0 to 3, preferably 0 to 2, and $R_{10}$ is hydrogen or phenyl, which is unsubstituted or substituted by halogen, halogen lower alkyl, lower alkoxy, hydroxy, lower alkoxycarbonyl, amino, lower alkylamino, di-lower alkylamino, carbamoyl, lower alkylcarbamoyl, carboxyl, methylenedioxy or cyano, or β) N-(aryl lower alkyl)carbamoyl, or γ) a radical of the formula —NH—S(=O)$_i$R$_8$, in which i is 1 or 2,
  $R_8$ is an aliphatic, carbocyclic or heterocyclic radical; or δ) a radical of the formula —NH—C(=O)—R$_8$, in which
  $R_9$ is alkoxy, aryloxy, alkenyl, alkynyl, heterocyclyl alkynyl, aryl alkynyl, heteroaryl alkynyl, alkynyloxy or aryl alkynyloxy, which in each case is unsubstituted or substituted, the substituents being selected from the group consisting of halogen, hydroxy, phenyl, lower alkyl, lower alkoxy, lower alkoxycarbonyl, amino, lower alkylamino, di-lower alkylamino, carbamoyl, lower alkylcarbamoyl, carboxyl, methylenedioxy, tri-lower alkyl silyl, cyano or lower alkyl which is substituted by halogen, wherein such an unsubstituted or substituted $R_9$ radical has not more than 20 atoms;

where, if more than one radical $R_1$ is present in th molecule, these can be identical or different from one another, $R_2$ is hydrogen, carbamoyl or N-lower alkyl-carbamoyl, $R_3$ is lower alkyl, which is unsubstituted or substituted by hydroxy, lower alkoxy, amino, lower alkylamino or N,N-di-lower alkylamino and a) $R_4$ is hydrogen, amino, phenylamino, lower alkylamino, hydroxyl, phenoxy, lower alkoxy, acyl having 1–30 C atoms, a carbocyclic or carbocyclic-aliphatic radical having not more than 29 C atoms, a heterocyclic or heterocyclic-aliphatic radical having not more than 20 C atoms and not more than 9 heteroatoms, or a substituted hydrocarbon radical having not more that 29 C atoms wherein the substituents are selected from halogen, amino, lower alkylamino, ω-amino-lower alkylamino, lower alkanoylamino, benzoylamino, hydroxylamino, hydroxylimino, lower alkoxy-amino, phenyloxyamino, amino-cyclohexyl-amino-, amino-phenyl-amino-, carbamoyl-amino, (N-lower alkyl-carbamoyl)-amino, (N-[ω-amino-lower alkyl]-carbamoyl)-carbamoyl)-amino, (N-phenyl-carbamoyl)-amino, lower alkylthio, thiocarbamoyl, thioureido, N-lower alkyl-thioureido, N-phenyl-thioureido, guanidino, N-lower alkyl-guanidino, carboxyl, lower alkoxycarbonyl, phenyloxycarbonyl, benzyloxycarbonyl, hydroxylaminocarbonyl, carbamoyl, amidino, cyano, hydroxyl, lower alkoxy, phenyloxy, aminocarbonyl-oxy, oxo, aminosulfonyl, lower alkylsulfonyl-amino, glycylamino, alanylamino, phenylalanylamino, prolylamino, valylamino, leucylamino, isoleucylamino, serylamino, threonylamino, cysteinylamino, methionylamino, tyrosylamino, tryptophanylamino, arginylamino, histidylamino, lysylamino, glutamylamino, glutaminylamino, asparagylamino, asparaginylamino and phenylglycylamino; and $R_5$, independently of $R_4$, is as defined above for $R_4$, with the exception of hydrogen, or b) $R_4$ and $R_5$ together are 1,2-ethylene, propane-1,3-diyl, butane-1,4-diyl, pentane-1,5-diyl, 3(3-amino-propionyl)-3-aza-pentane-1,5-diyl, 2-amino-butane-1,4-diyl, 1-aminomethyl-butane-1,4-diyl, 1-hydroxymethyl-butane-1,4-diyl, 3-hydroxy-pentane-1,5-diyl, 1-hydroxy-hexane-1,5-diyl, 3-(2-amino-ethyl)-pentane-1,5-diyl, 3-aza-pentane-1,5-diyl (—CH$_2$—CH$_2$—NH—CH$_2$—CH$_2$—), 3-aza-2,4-dimethyl-pentane-1,5-diyl (—CH$_2$—CH[CH$_3$]—NH—CH[CH$_3$]—CH$_2$—), 3amino-3-aza-pentane-1,5-diyl (—CH$_2$—CH$_2$—N[NH$_2$]—CH$_2$—CH$_2$—), 1-aza-pentane-1,5-diyl, 1-aza-1-toluylaminocarbonyl-pentane-1,5-diyl, 1-aza-1-(methylamino-thiocarbonyl)-pentane-1,5-diyl, 1-aza-1-(tert-butylamino-carbonyl)-pentane-1,5-diyl, 1-aza-1-(cyclohexylamino-carbonyl)-pentane-1,5-diyl, 3-aza-1-hydroxy-heptane-3,7-diyl, 3-aza-1-cyano-heptane-3,7-diyl, 1amino-3-aza-heptane-3,7-diyl, 3-(2-amino-ethyl)-3-aza-pentane-1,5-diyl (—CH$_2$—CH$_2$—N[—CH$_2$—CH$_2$—NH$_2$]—CH$_2$—Ch$_2$—), 1-carbamoyl-butane-1,4-diyl, 2-formylamino-pentane-1,4-diyl, 2-aza-butadiene-1,4-diyl —(CH=CH—N=CH—), 2-aza-3-hydroxymethyl-butadiene-1,4-diyl (—CH=C[CH$_2$OH]—N=CH—), 2-Aza-1-hydroxy-1-(4-methoxy-phenyl-amino)-heptane-2,7-diyl {—(CH$_2$)$_4$—N[—CH(OH)—NH—C$_5$H$_4$—OCH$_3$]—} or a radical of the formula

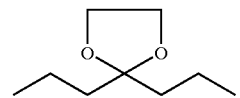

in which the two terminal bonds of the alkylene chain are free valencies, or a salt thereof, with the exception of 6-(4-benzyloxycarbonylamino-phenyl-amino)-9-ethyl-2-(2-hydroxy-ethyl-amino)-9H-purine or a salt thereof, which comprises a) for the manufacture of a compound of formula I, wherein $R_1$ is —SO$_k$NR$_6$R$_7$, reacting a compound of the formula III

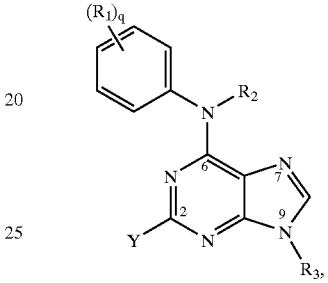

(III)

in which Y is a suitable leaving group, $R_1$ is —SO$_k$NR$_6$R$_7$ and the other substituents and symbols are as defined above for compounds of the formula I, free functional groups present in this compound, if necessary, being protected by easily detachable protective groups, with an amine of the formula IV

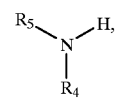

(IV)

in which the substituents are as defined above for compounds of the formula I, free functional groups present in this compound, if necessary, being protected by easily detachable protective groups, and detaching the protective groups present and, if necessary, converting functional groups into the final from according to formula I, or b) for the manufacture of a compound of formula I, wherein $R_1$ is N-(aryl lower alkyl) carbamoyl, reacting a compound of the formula V

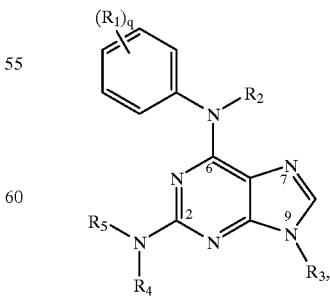

(V)

in which $R_1$ is —CO$_2$H and the other substituents and symbols are as defined above for compounds of the formula I, free functional groups present in this compound, if necessary, being protected by easily detachable protective groups, with an aryl lower alkyl amine, free functional groups present in the aryl moiety, if necessary, being protected by easily detachable protective groups, and detaching the protective groups present, or c) for the manufacture of a compound of formula I, wherein $R_1$ is a radical of the formula —NH—S(=O)$_i$—$R_5$ or of the formula —NH—C(=O)—$R_9$, reacting a compound of the formula V in which $R_1$ is —NH$_2$ and the other substituents and symbols are as defined above for compounds of the formula I, free functional groups present in this compound, if necessary, being protected by easily detachable protective groups, with a compound of the formula VI or VII, $$R_8SO_iY(VI) \text{ or } R_9COY \quad (VII),$$

in which Y is a suitable leaving group and $R_8$ and $R_9$ are as defined above for compounds of the formula I, free functional groups present in $R_8$ and $R_9$, if necessary, being protected by easily detachable protective groups, and detaching the protective groups present, and, after carrying out process a), b) or c), if necessary for the preparation of a salt, converting a resulting free compound of the formula I into a salt or, if necessary for preparation of a free compound, converting a resulting salt of a compound of the formula I into the free compound;

wherein in the above definitions an aliphatic radical is an unsubstituted or substituted alkyl, alkenyl or alkynyl radical having not more than 20 C atoms which alkenyl or alkynyl radicals are mono- or polyunsaturated and a substituted aliphatic radical carries one or more identical or different radicals selected from halogen, amino, lower alkylamino, di-lower alkylamino, ω-amino-lower alkylamino, lower alkanoylamino, aroylamino, hydroxylamino, hydroxylimino, lower alkoxy-amino, aryloxyamino, amino-cyclohexyl-amino-, amino-phenyl-amino-, carbamoyl-amino, (N-lower alkyl-carbamoyl)-amino, (N-[ω-amino-lower alkyl]-carbamoyl)-amino, (N-phenyl-carbamoyl)-amino, thio, lower alkylthio, thiocarbamoyl, thioureido, N-lower alkyl-thioureido, N-phenyl-thioureido, guanidino, N-lower alkyl-guanidino, carboxyl, lower alkoxycarbonyl, aryloxycarbonyl, benzyloxycarbonyl, hydroxylaminocarbonyl, aminoacyl-amino, carbamoyl, amidino, cyano, hydroxy, lower alkoxy, aryloxy, aminocarbonyl-oxy, oxo, aminosulfonyl and lower alkylsulfonyl-amino.

wherein hydrocarbon is either: 1) an acyclic, carbocyclic, or carbocyclic-acyclic radical having no more that 28 carbon atoms, or 2) an acyclic, carbocyclic, or carbocyclic-acyclic radical interrupted by one or more identical or different heteroatoms selected from oxygen, sulfur, and nitrogen having a total of no more than 29 C, O, S, and N atoms.

13. A compound of the formula III

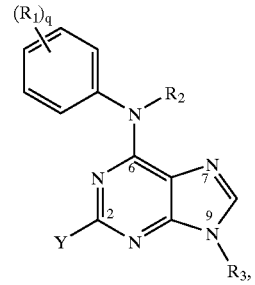

in which q is 1–5

Y is a suitable leaving group, $R_1$ is —SO$_2$NR$_6$R$_7$ $R_2$ is hydrogen, carbamoyl or N-lower alkyl-carbamoyl, $R_3$ is lower alkyl, which is unsubstituted or substituted by hydroxy, lower alkoxy, amino, lower alkylamino or N,N-di-lower alkylamino;

$R_6$, $R_7$ can be identical or different from one another and represent an aliphatic, carbocyclic, heterocyclic, carbocyclic-aliphatic or heterocyclic-aliphatic radical; hydrogen or lower aliphatic acyl; or $R_6$ and $R_7$ together are an alkylene or alkenylene radical having from 3 up to and including 9 C atoms, in which 1–3 C atoms can be replaced by oxygen, sulfur or nitrogen, wherein said alkylene or alkenylene radical can be unsubstituted or substituted by halogen, hydroxy, lower alkoxy, amino, lower alkylamino, di-lower alkylamino, carbamoyl, lower alkylcarbamoyl or a radical —(CH$_2$)$_y$—$R_{10}$, in which y is 0 to 3, preferably 0 to 2, and $R_{10}$ is hydrogen or phenyl, which is unsubstituted or substituted by halogen, halogen lower alkyl, lower alkoxy, hydroxy, lower alkoxycarbonyl, amino, lower alkylamino, di-lower alkylamino, carbamoyl, lower alkylcarbamoyl, carboxyl, methylenedioxy or cyano, it being possible for free functional groups present therein to be protected by easily detachable protective groups, or a salt thereof;

wherein in the above definitions an aliphatic radical is an unsubstituted or substituted alkyl, alkenyl or alkynyl radical having not more than 20 C atoms which alkenyl or alkynyl radicals are mono- or polyunsaturated and a substituted aliphatic radical carries one or more identical or different radicals selected from halogen, amino, lower alkylamino, di-lower alkylamino, ω-amino-lower alkylamino, lower alkanoylamino, aroylamino, hydroxylamino, hydroxylimino, lower alkoxy-amino, aryloxyamino, amino-cyclohexyl-amino-, amino-phenyl-amino-, carbamoyl-amino, (N-lower alkyl-carbamoyl)-amino, (N-[ω-amino-lower alkyl]-carbamoyl)-amino, (N-phenyl-carbamoyl)-amino, thio, lower alkylthio, thiocarbamoyl, thioureido, N-lower alkyl-thioureido, N-phenyl-thioureido, guanidino, N-lower alkyl-guanidino, carboxyl lower alkoxycarbonyl, aryloxycarbonyl, benzyloxycarbonyl, hydroxylaminocarbonyl, aminoacyl-amino, carbamoyl, amidino, cyano hydroxy, lower alkoxy, aryloxy, aminocarbonyl-oxy, oxo, aminosulfonyl and lower alkylsulfonyl-amino.

14. A compound of the formula I

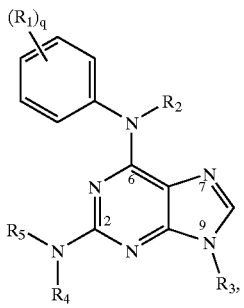

wherein
q is 1–5,
$R_1$ is
  α) —S(=O)$_k$—NR$_6$R$_7$, in which
    k is 1 or 2,
    wherein under the proviso that $R_8$ and $R_7$ cannot be simultaneously hydrogen
      α1) $R_6$, $R_7$ can be identical or different from one another and represent an aliphatic, carbocyclic, heterocyclic, carbocyclic-aliphatic or heterocyclic-aliphatic radical; hydrogen or lower aliphatic acyl; or
      α2) $R_6$ and $R_7$ together are an alkylene or alkenylene radical having from 3 up to and including 9 C atoms, in which 1–3 C atoms can be replaced by oxygen, sulfur or nitrogen, wherein said alkylene or alkenylene radical can be unsubstituted or substituted by halogen, hydroxy, lower alkoxy, amino, lower alkylamino, di-lower alkylamino, carbamoyl, lower alkylcarbamoyl or a radical —(CH$_2$)$_y$—$R_{10}$, in which y is 0 to 3, preferably 0 to 2, and $R_{10}$ is hydrogen or phenyl, which is unsubstituted or substituted by halogen, halogen lower alkyl, lower alkoxy, hydroxy, lower alkoxycarbonyl, amino, lower alkylamino, di-lower alkylamino, carbamoyl, lower alkylcarbamoyl, carboxyl, methylenedioxy or cyano, or
  β) N-(aryl lower alkyl)carbamoyl, or
  γ) a radical of the formula —NH—S(=O)$_i$—R$_8$, in which
    i is 1 or 2,
    $R_8$ is an aliphatic, carbocyclic or heterocyclic radical; or
  δ) a radical or the formula —NH—C(=O)—R$_9$, in which
    $R_9$ is alkoxy, aryloxy, alkenyl, alkynyl, heterocyclyl alkynyl, aryl alkynyl, heteroaryl alkynyl, alkynyloxy or aryl alkynyloxy, which in each case is unsubstituted or substituted, the substituents being selected from the group consisting of halogen, hydroxy, lower alkyl, lower alkoxy, lower alkoxycarbonyl, amino, lower alkylamino, di-lower alkylamino, carbamoyl, lower alkylcarbamoyl, carboxyl, methylenedioxy, tri-lower alkyl silyl, cyano or lower alkyl which is substituted by halogen, wherein such an unsubstituted or substituted $R_9$ radical has not more than 20 C atoms;
  where, if more than one radical $R_1$ is present in the molecule, these can be identical or different from one another, $R_2$ is hydrogen, carbamoyl or N-lower alkyl-carbamoyl, $R_3$ is lower alkyl, which is unsubstituted or substituted by hydroxy, lower alkoxy, amino, lower alkylamino or N,N-di-lower alkylamino and a) $R_4$ is hydrogen, amino, phenylamino, lower alkylamino, hydroxyl, phenoxy, lower alkoxy, acyl having 1–30 C atoms, a carbocyclic or carbocyclic-aliphatic radical having not more than 29 C atoms, a heterocyclic or heterocyclic-aliphatic radical having not more than 20 C atoms and not more than 9 heteroatoms, or a substituted hydrocarbon radical having not more than 29 C atoms wherein the substituents are selected from halogen, amino, lower alkylamino, ω-amino-lower alkylamino, lower alkanoylamino, benzoylamino, hydroxylamino, hydroxylimino, lower alkoxy-amino, phenyloxyamino, amino-cyclohexyl-amino-, amino-phenyl-amino-, carbamoyl-amino, (N-lower alkyl-carbamoyl)-amino, (N-[ω-amino-lower alkyl]-carbamoyl)-amino, (N-phenyl-carbamoyl)-amino, lower alkylthio, thiocarbamoyl, thioureido, N-lower alkyl-thioureido, N-phenyl-thioureido, guanidino, N-lower alkyl-guanidino, carboxyl, lower alkoxycarbonyl, phenyloxycarbonyl, benzyloxycarbonyl, hydroxylaminocarbonyl, carbamoyl, amidino, cyano, hydroxyl, lower alkoxy, phenyloxy, aminocarbonyl-oxy, oxo, aminosulfonyl, lower alkylsulfonyl-amino, glycylamino, alanylamino, phenylalanylamino, prolylamino, valylamino, leucylamino, isoleucylamino, serylamino, threonylamino, cysteinylamino, methionylamino, tyrosylamino, tryptophanylamino, arginylamino, histidylamino, lysylamino, glutamylamino, glutaminylamino, asparagylamino, asparaginylamino and phenylglycylamino; and $R_6$, independently of $R_4$, is as defined above for $R_4$, with the exception of hydrogen, or b) $R_4$ and $R_5$ together are 1,2-ethylene, propane-1,3-diyl, butane-1,4-diyl, butane-1,5-diyl, 3-(3-amino-propionyl)-3-aza-pentane-1,5-diyl, 2-amino-butane-1,4-diyl, 1-aminomethyl-butane-1,4-diyl, 1-hydroxymethyl-butane-1,4-diyl, 3-hydroxy-pentane-1,5-diyl, 1-hydroxy-hexane-1,5-diyl, 3-(2-amino-ethyl)-pentane-1,5-diyl, 3-aza-pentane-1,5-diyl (—CH$_2$—CH$_2$—NH—CH$_2$—CH$_2$—), 3-aza-2,4-dimethyl-pentane-1,5-diyl (—CH$_2$—CH[CH$_3$]—NH—CH[CH$_3$]—CH$_2$—), 3-amino-3-aza-pentane-1,5-diyl (—CH$_2$—CH$_2$—N[NH$_2$]—CH$_2$—CH$_2$—), 1-aza-pentane-1,5-diyl, 1-aza-1-toluylaminocarbonyl-pentane-1,5-diyl, 1-aza-1-(methylamino-thiocarbonyl)-pentane-1,5-diyl, 1-aza-1-(tert-butylamino-carbonyl)-pentane-1,5-diyl, 1aza-1-(cyclohexylamino-carbonyl)-pentane-1,5-diyl, 3-aza-1-hydroxy-heptane-3,7-diyl, 3-aza-1-cyano-heptane-3,7-diyl, 1-amino-3aza-heptane-3,7-diyl, 3-(2-amino-ethyl)-3-aza-pentane-1,5-diyl (—CH$_2$—CH$_2$—N[—CH$_2$—CH$_2$—NH$_2$]—CH$_2$—CH$_2$—), 1-carbamoyl-butane-1,4-diyl, 2-formylamino-pentane-1,4-diyl, 2-aza-butadiene-1,4-diyl (—CH=CH—N=CH—), 2-aza-3-hydroxymethyl-butadiene-1,4-diyl (—CH=C[CH$_2$OH]—N=CH—) or a radical of the formula

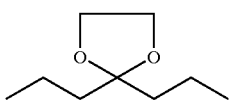

in which the two terminal bonds of the alkylene chain are free valencies,
or a salt thereof;
wherein the above definitions
an aliphatic radical is an unsubstituted or substituted alkyl, alkenyl or alkynyl radical having not more than 20 C atoms which alkenyl or alkynyl radicals are mono- or polyunsaturated and a substituted aliphatic radical carries one or more identical or different radicals selected from halogen, amino, lower alkylamino, di-lower alkylamino, ω-amino-lower alkylamino, lower alkanoylamino, aroylamino, hydroxylamino, hydroxylamino, hydroxylimino, lower alkoxy-amino, aryloxyamino, amino-cyclohexyl-amino-, amino-phenyl-amino-, carbamoyl-amino, (N-lower alkyl-carbamoyl)-amino, (N-[ω-amino-lower alkyl]-carbamoyl)-amino, (N-phenyl-carbamoyl)-amino, thio lower alkylthio, thiocarbamoyl, thioureido, N-lower alkyl-thioureido, N-phenyl-thioureido, guanidino, N-lower alkyl-guanidino, carboxyl, lower alkoxycarbonyl, aryloxycarbonyl, benzyloxycarbonyl, hydroxylaminocarbonyl, aminoacyl-amino, carbamoyl, amidino, cyano, hydroxy, lower alkoxy, aryloxy, aminocarbonyl-oxy, oxo, aminosulfonyl and lower alkylsulfonyl-amino
wherein hydrocarbon is either: 1) an acyclic, carbocyclic, or carbocyclic-acyclic radical having no more than 29 carbon atoms, or 2) an acyclic, carbocyclic, or carbocyclic-acyclic radical interrupted by one or more identical or different heteroatoms selected from oxygen, sulfur, and nitrogen having a total of no more than 29 C, O, S, and N atoms.

15. A pharmaceutical composition for treatment of tumors in a human which comprises an antitumorally effective amount of a compound of claim 14, or a pharmaceutically acceptable salt thereof, together with a pharmaceutically acceptable carrier.

* * * * *